US012617859B2

(12) United States Patent
Lugovskoy

(10) Patent No.: US 12,617,859 B2
(45) Date of Patent: May 5, 2026

(54) THERAPEUTIC ANTI-CD40 LIGAND ANTIBODIES

(71) Applicant: ALS Therapy Development Institute, Watertown, MA (US)

(72) Inventor: Alexey Lugovskoy, Belmont, MA (US)

(73) Assignee: ALS THERAPY DEVELOPMENT INSTITUTE, Watertown, MA (US)

( * ) Notice: Subject to any disclaimer, the term of this patent is extended or adjusted under 35 U.S.C. 154(b) by 902 days.

(21) Appl. No.: 17/811,642

(22) Filed: Jul. 11, 2022

(65) Prior Publication Data

US 2023/0048260 A1     Feb. 16, 2023

Related U.S. Application Data

(63) Continuation of application No. 16/615,757, filed as application No. PCT/US2018/034172 on May 23, 2018, now Pat. No. 11,384,152.

(60) Provisional application No. 62/510,471, filed on May 24, 2017.

(51) Int. Cl.
    *A61K 39/395* (2006.01)
    *C07K 16/28* (2006.01)

(52) U.S. Cl.
    CPC ........ *C07K 16/2875* (2013.01); *A61K 39/395* (2013.01); *C07K 2317/24* (2013.01); *C07K 2317/52* (2013.01); *C07K 2317/565* (2013.01)

(58) Field of Classification Search
    None
    See application file for complete search history.

(56) References Cited

U.S. PATENT DOCUMENTS

| | | |
|---|---|---|
| 5,474,771 A | 12/1995 | Lederman et al. |
| 5,637,481 A | 6/1997 | Ledbetter et al. |
| 5,851,795 A | 12/1998 | Linsley et al. |
| 5,961,974 A | 10/1999 | Armitage et al. |
| 5,962,406 A | 10/1999 | Armitage et al. |
| 6,001,358 A | 12/1999 | Black et al. |
| 6,328,964 B1 | 12/2001 | Noelle et al. |
| 6,340,459 B1 | 1/2002 | Yellin et al. |
| 6,376,459 B1 | 4/2002 | Aruffo et al. |
| 6,451,310 B1 | 9/2002 | Lederman et al. |
| 6,838,261 B1 | 1/2005 | Siegall et al. |
| 7,070,777 B1 | 7/2006 | Lederman et al. |
| 7,169,389 B2 | 1/2007 | Di Padova et al. |
| 7,173,046 B2 | 2/2007 | Zheng et al. |
| 7,547,438 B2 | 6/2009 | Thomas et al. |
| 7,563,443 B2 | 7/2009 | Grant et al. |
| 7,647,438 B1 | 1/2010 | Norrie et al. |
| 7,863,419 B2 | 1/2011 | Taylor et al. |
| 8,293,237 B2 | 10/2012 | Burkly et al. |
| 8,435,514 B2 | 5/2013 | Perrin et al. |
| 8,647,625 B2 | 2/2014 | Van Vlijmen et al. |
| 8,784,823 B2 | 7/2014 | Burkly et al. |
| 8,895,010 B2 | 11/2014 | Nadler et al. |
| 8,981,072 B2 | 3/2015 | Nadler et al. |
| 9,028,826 B2 | 5/2015 | Noelle |
| 9,044,459 B2 | 6/2015 | Perrin et al. |
| 9,228,018 B2 | 1/2016 | Nadler et al. |
| 10,106,618 B2 | 10/2018 | Lincecum |
| 10,683,356 B2 | 6/2020 | Lincecum |
| 11,014,990 B2 | 5/2021 | Lincecum et al. |
| 11,384,152 B2 | 7/2022 | Lugovskoy |
| 11,692,040 B2 | 7/2023 | Lincecum et al. |
| 2001/0018041 A1 | 8/2001 | Hanna et al. |
| 2004/0006208 A1 | 1/2004 | Karpusas et al. |
| 2004/0110226 A1 | 6/2004 | Lazar |
| 2007/0048300 A1 | 3/2007 | Taylor et al. |
| 2007/0190053 A1 | 8/2007 | Kalled et al. |
| 2008/0138349 A1 | 6/2008 | Stavenhagen et al. |
| 2011/0172400 A1 | 7/2011 | Grant et al. |
| 2012/0251531 A1 | 10/2012 | Baehner et al. |
| 2013/0045219 A1 | 2/2013 | Burkly |
| 2013/0095109 A1 | 4/2013 | Nadler et al. |
| 2014/0099317 A1 | 4/2014 | Suri et al. |
| 2014/0220031 A1 | 8/2014 | Van Vlijmen et al. |
| 2014/0302016 A1 | 10/2014 | Burkly et al. |
| 2014/0363428 A1 | 12/2014 | Igawa |
| 2015/0104450 A1 | 4/2015 | Minter et al. |
| 2016/0075790 A1 | 3/2016 | Nadler et al. |
| 2017/0166655 A1 | 6/2017 | Lazar et al. |

FOREIGN PATENT DOCUMENTS

| | | |
|---|---|---|
| CN | 1441675 | 9/2003 |
| CN | 102119174 | 7/2011 |
| CN | 103154037 | 6/2013 |
| WO | WO 95/006481 | 3/1995 |
| WO | WO 96/040246 | 12/1996 |
| WO | WO 98/052606 | 11/1998 |

(Continued)

OTHER PUBLICATIONS

Crepeau et al., Aug. 2017, Challenges and opportunities in targeting the CD28/CTLA-4 pathway in transplantation and autoimmunity, Expert Opin Biol Ther., 17(8):10011012.
Hargreaves, Mar. 31, 2004, Selective depletion of activated T cells: the CD40L-specific antibody experience, Trends in Molecular Medicine, 10(3):130-135.
Needleman et al., 1970, A general method applicable to the search for similarities in the amino acid sequence of two proteins, J. Mol. Biol. 48:444-453.
Zhang et al., May 2008, Effects of anti-CD40L monoclonal antibodies on rejection of rat pancreatic islet xenografts, Chinese J Bases Clin General Surg, 15(5):329-332.
Abcam, "Anti-GAL4 antibody [5C8]," 2012, 2 pages.

(Continued)

*Primary Examiner* — Christine J Saoud
*Assistant Examiner* — Jon M Lockard
(74) *Attorney, Agent, or Firm* — Sterne, Kessler, Goldstein & Fox P.L.L.C.

(57) ABSTRACT

Anti-CD40L antibodies and antigen binding fragments thereof, compositions comprising the antibodies or antigen binding fragments, Anti-CD40L antibodies with reduced effector function, and method of using same for treatment of CD40L-related diseases or disorders.

21 Claims, 23 Drawing Sheets

Specification includes a Sequence Listing.

(56)                References Cited

FOREIGN PATENT DOCUMENTS

| WO | WO 99/051258 | 10/1999 |
| WO | WO 01/083755 | 11/2001 |
| WO | WO 02/004021 | 1/2002 |
| WO | WO 02/018445 | 3/2002 |
| WO | WO 04/037204 | 5/2004 |
| WO | WO 05/003174 | 1/2005 |
| WO | WO 05/003175 | 1/2005 |
| WO | WO 05/011376 | 2/2005 |
| WO | WO 06/029879 | 3/2006 |
| WO | WO 06/138316 | 12/2006 |
| WO | WO 07/059332 | 5/2007 |
| WO | WO 07/076354 | 7/2007 |
| WO | WO 08/118356 | 10/2008 |
| WO | WO 08/143954 | 11/2008 |
| WO | WO 10/023482 | 3/2010 |
| WO | WO 10/065819 | 6/2010 |
| WO | WO 10/085682 | 7/2010 |
| WO | WO 12/103218 | 8/2012 |
| WO | WO 12/138768 | 10/2012 |
| WO | WO 13/033008 | 3/2013 |
| WO | WO 13/046704 | 4/2013 |
| WO | WO 13/056068 | 4/2013 |
| WO | WO 14/163101 | 10/2014 |
| WO | WO 15/143209 | 9/2015 |
| WO | WO 14/132101 | 10/2015 |
| WO | WO 15/164595 | 10/2015 |
| WO | WO 16/028810 | 2/2016 |
| WO | WO 16/126702 | 8/2016 |

OTHER PUBLICATIONS

Baker et al, 2007, Identification and Removal of Immunogenicity in Therapeutic Proteins, Current Opinion in Drug Discovery & Development, 10(2):219-227.

Bosco et al., "Wild-type and mutant SOD1 share an aberrant Conformation and a common pathogenic pathway in ALS", Nat. Neurosci., 2010, vol. 13, No. 11, pp. 1396-1403.

Building a Better Mouse, MDA/ALS Newsmagazine, Sep. 1, 2010.

Chen et al., "Enhancement and Destruction of Antibody Function by Somatic Mutation: Unequal Occurrence is Controlled by V Gene Combinatorial Associations," EMBO J., 1995; vol. 14, pp. 2784-2794.

Cicchetti et al., 2009, Environmental toxins and Parkinson's disease: what have we learned from pesticide-induced animal models, Trends in Pharmacological Sciences 30:475-483.

Colman, 1994, Effects of amino acid sequence chagnes on antibody-antigen interactions, Research in Immunology 145: 33-36.

Daley et al., "Fc-Disabled Anti-Mouse CD40L Antibodies Retain Efficacy in Promoting Transplantation Tolerance," Am J Transplantation, 2008, vol. 8, pp. 2265-2271.

D'Angelo et al., "Many Routes to an Antibody Heavy-Chain CDR3: Necessary, Yet Insufficient, for Specific Binding, Frontiers in Immunology," Frontiers in Immunology, Original Research, Mar. 2018, vol. 9, Article 395 doi:10.3389/immu.2018.00395.

Davis et al., "Abatacept binds to the Fc receptor CD64 but does not mediate complement-dependent cytotoxicity or antibody-dependent cellular cytotoxicity," J. Rheumatol., 2007, vol. 34, No. 11, pp. 2204-2210.

Drachman et al., 1994, Trail of immunosuppression in amyotrophic lateral sclerosis neuro—using total lymphoid irradiation, Annals of Neurology, 35(2).

Dumont et al., "IDEC-131. IDEC/Eisai," Curr Opin Inventing Drugs, 2002, pp. 725-734, vol. 3, No. 5.

Gilliland "Rapid and Reliable Cloning of Antibody Variable Regions and Generation of Recombinant Single Chain Antibody Fragments", Tissue Antigens, 1996, vol. 47, pp. 1-20.

Gruzman et al., "Common Molecular Signature in SOD1 for both Sporadic and Familial Amyotrophic Lateral Sclerosis", PNAS, 2007, vol. 104, No. 30, pp. 12524-12529.

Holgate et al., "Circumventing Immunogenicity in the Development of Therapeutic Antibodies," Idrugs, 2009, vol. 12, No. 4, pp. 233-237.

Imgenex, Monoclonal Antibody to IGF-1R (Clone 24-31), accessed Sep. 21, 2012, 2 pgs.

Jefferis, Mar. 2009, IgG-Fc-mediated effector functions: molecular definition of interaction sites for effector ligands and the role of glycosylation, Nature Reviews/Drug Discovery, 8:226-234.

Karpusas et al., "Structure of CD40 Ligand in Complex with the Fab Fragment of a Neutralizing Humanized Antibody," Structure, 2001, vol. 9, No. 4, pp. 321-329.

Ke et al, "CD40-CD40L interactions promote neuronal death in a model of neurodegeneration due to mild impairment of oxidative metabolism", Neurochemistry International, 2005, pp. 204-215, vol. 47, No. 3.

Kiaei et al., "Celastrol blocks neuronal cell death and extends life in transgenic mouse model of amyotrophic lateral sclerosis," Neurodegenerative Diseases, 2005, pp. 246-254, vol. 2, No. 5.

Kirk et al., "CTLA4-Ig and anti-CD40 Ligand Prevent Renal Allograft Rejection in Primates", Proc Natl Acad Sci Neuro—USA, 1997, vol. 94, pp. 8789-8794.

Kiyoshi et al., 2018, Assessing the heterogeneity of the Fc-Glycan of a therapeutic antibody using an engineered FcγReceptor IIIa-immobilized column, Scientific Reports, 8:3955 pp. 1-11.

Knosalla et al., "Initial experience with the human anti-human CD154 monoclonal antibody, ANI793, in pig-to-baboon xenotransplantation", Xenotransplantation, 2004, pp. 353-360, vol. 11, No. 4.

Kussie et al., "a Single Engineered Amino Acid Substitution Changes Antibody Fine Specificity," 1994, J. Immunol., vol. 152, pp. 146-152.

Law et al., "Preclinical Antilymphoma Activity of a Human Anti-CD40 Monoclonal Antibody, SGN-40", Cancer Res, 2005, vol. 65, No. 18, pp. 8331-88338.

Lederman et al., "Identification of a Novel Surface Protein on Activated CD4+ T Cells That Induces Contact-dependent B Cell Differentiation (Help)," J. Exp. Med., 1992, vol. 175, No. 4, pp. 1901-1101.

Leitner et al., Working with ALS Mice:, The Jackson Laboratory, Oct. 14, 2009.

Lincecum et al., "From Transcriptome Analysis to Therapeutic anti-CD40L Treatment in the SOD1 Model of Amyotrophic Lateral Sclerosis", Nature Genetics, 2010, pp. 1-10.

Linsley et al., "CTLA-4 is a Second Receptor for the B Cell Activation Antigen B7," J. Exp. Med., 1991, vol. 174, No. 3, pp. 561-569.

Ludolph et al., "Guidelines for Preclinical Animal Research in ALS/MND: A Consensus Meeting," Amyotrophic Lateral Sclerosis, 2010, vol. 11, pp. 38-45.

Madsen A., Building a Better Mouse: How Animal Models Help Fight ALS, MDA/ALS Newsmagazine, Sep. 1, 2010, vol. 15, No. 5, 4 pages.

National Institute of Neurological Disorders and Stroke (NINDS), "Amyotrophic Lateral Sclerosis (ALS) Fact Sheet", NIH Internet Publication relating to ALS accessed Nov. 19, 2012, 8 pp.

Okuno et al., "Induction of cyclooxygenase-2 in reactive glial cells by the CD40 pathway: relevance to amyotrophic lateral sclerosis," Journal of Neurochemistry, 2004, vol. 91, No. 2, pp. 404-412.

Piche-Nicholas et al., "Changes in complementarity-determining regions significantly alter IgG binding to the neonatal Fc receptor (FcRN) and pharmacokinetics," MABS, 2018, vol. 10, No. 1, pp. 81-94, oi.org/10.1080/19420862.2017.1389355.

Rudikoff et al., "Single Amino Acid Substitution Altering Antigen-binding Specificity," Proc Natl Acad Sci USA, Mar. 1982, vol. 79, pp. 1979-1983.

Sakoda, Saburou, "Study on a breakthrough technique to diagnosis or treat amyotrophic lateral sclerosis—Analysis of CD40 in amyotrophic lateral sclerosis"—Report of 2006 Houkatsu Kenkyuu, 2007, pp. 51-53 (English translation).

Santa Cruz Biotechnology Inc., accessed Sep. 21, 2012, 1 pg.

Saunders et al., 2019, Conceptual approaches to modulating antibody effector functions and circulating half-life, Frontiers in Immunology, 10:1-20.

(56) References Cited

OTHER PUBLICATIONS

Seattle Genetics Receives Key U.S. Patents for SGN-40 Program, Jan. 19, 2005, http://www.seattlegenetics.com/, Posted by MMSupport. net, http://www.mmsupport.net/seattle-genetics-receives-key-Neuro - US-patents-for-sgn-40-program/, 3 pages.

Starzl et al., "Refinements in the Surgical Technique of Liver Transplantation," Semin Liver Dis., 1985, vol. 5, No. 4, pp. 349-356.

Tai et al., "Mechanisms by Which SGN-40, a Humanized Anti-CD40 Antibody, Induces Cytotoxicity in Human Multiple Myeloma Cells: Clinical Implications", Cancer Research, 2004, vol. 64, pp. 2846-2852.

Traynor et al., "Neuroprotective agents for clinical trials in ALS: A systematic assessment," Neurology, 2006, vol. 67, pp. 20-27.

Vainzof et al., "Animal Models for Genetic Neuromuscular Diseases," J. Mol. Neurosci., 2008, pp. 241-248, vol. 34.

Van Blitterswijk et al., "Anti-superoxide Dismutase Antibodies are Associated with Survival in Patients with Sporadic Amyotrophic Lateral Sclerosis", Amyotroph Lateral Scler, 2011, vol. 12, No. 6, pp. 430-438.

Viglietta et al., "CTLA4Ig treatment in patients with multiple sclerosis", Neurology, 2008, pp. 917-924, vol. 71, No. 12.

Wang et al., 2018, IgG Fc engineering to modulate antibody effector functions, Protein Cell, 9:63-73.

Xie et al., "Engineering of a Novel Anti-CD40L Domain Antibody for Treatment of Autoimmune Diseases," J. Immunol., 2014, vol. vol. 192, No. 9, pp. 4083-4092.

International Search Report and Written Opinion dated Dec. 17, 2018 in PCT/US2018/034172.

Kallmeier, R.C., et al., "Improvements to the GS System for Easier Re-Expression of Human Antibodies," webpage <http://bio.lonza. com/uploads/tx_mwaxmarketingmaterial/Lonza_Posters_Easier_Expression_of_Antibodies_using_GS.pdf>, 1 page, Dec. 10, 2015, retrieved from Internet Archive Wayback Machine <https://web. archive.org/web/20150615000000*/http://bio.lonza.com/uploads/tx_mwaxmarketingmaterial/Lonza_Posters_Easier_Expression_of_Antibodies_using_GS.pdf> on Nov. 25, 2025.

Ranked Relative Potency of 16 Clones vs. 5c8

Ranked Relative Potency of 16 Clones vs. AT-1501

FcγRI Set 1

FcγRI Set 2

FcγRIIa Set 1

Legend:
- 5C8
- AT-1501
- Abatacept
- 4-4
- 5-3
- 6-6
- 7-5
- 8-3
- 8-4
- 10-1
- 10-4

FcγRIIa Set 2

Legend:
- 5C8
- AT-1501
- Abatacept
- 11-5
- 12-4
- 13-2
- 15-1
- 15-4
- 16-3
- 17-1
- 18-2

FcγRIIIa Set 1

FcγRIIIa Set 2

C1q Set 1

C1q Set 2

SEQUENCE LISTING

```
Sequence total quantity: 57
SEQ ID NO: 1          moltype = AA  length = 118
FEATURE               Location/Qualifiers
REGION                1..118
                      note = Synthetic
source                1..118
                      mol_type = protein
                      organism = synthetic construct
SEQUENCE: 1
EVQLVQSGAE VKKPGASVKV SCKASGYTFT SYYMYWVRQA PGQGLEWMGE INPSNGDTNY  60
AQKFQGRVTM TVDTSTSTVY MELSSLRSED TAVYYCARSD GRNDMDSWGQ GTLVTVSS   118

SEQ ID NO: 2          moltype = AA  length = 118
FEATURE               Location/Qualifiers
```

-continued

```
REGION                    1..118
                          note = Synthetic
source                    1..118
                          mol_type = protein
                          organism = synthetic construct
SEQUENCE: 2
EVQLVQSGAE VKKPGASVKV SCKASGYIFT SYYMYWVRQA PGQGLEWMGE INPSNGDTNY  60
AEKFKGRVTM TVDTSTSTVY MELSSLRSED TAVYYCTRSD GRNDMDSWGQ GTLVTVSS    118

SEQ ID NO: 3              moltype = AA   length = 118
FEATURE                   Location/Qualifiers
REGION                    1..118
                          note = Synthetic
source                    1..118
                          mol_type = protein
                          organism = synthetic construct
SEQUENCE: 3
EVQLVQSGAE VKKPGASVKV SCKASGYIFT SYYMYWVRQA PGQGLEWIGE INPSNGDTNY  60
AEKFKGRATL TVDTSTSTVY MELSSLRSED TAVYYCTRSD GRNDMDSWGQ GTLVTVSS    118

SEQ ID NO: 4              moltype = AA   length = 118
FEATURE                   Location/Qualifiers
REGION                    1..118
                          note = Synthetic
source                    1..118
                          mol_type = protein
                          organism = synthetic construct
SEQUENCE: 4
QVQLVQSGAE VKKPGASVKV SCKASGYIFT SYYMYWVRQA PGQGLEWIGE INPSNGDTNF  60
AEKFKGRATL TVDTSTSTVY MELSSLRSED TAVYYCTRSD GRNDMDSWGQ GTLVTVSS    118

SEQ ID NO: 5              moltype = AA   length = 111
FEATURE                   Location/Qualifiers
REGION                    1..111
                          note = Synthetic
source                    1..111
                          mol_type = protein
                          organism = synthetic construct
SEQUENCE: 5
EIVLTQSPAT LSLSPGERAT LSCRASQRVS SSTYSYMHWY QQKPGQAPRL LIYDASNRAT  60
GIPARFSGSG SGTDFTLTIS SLEPEDFAVY YCQHSWEIPP TFGQGTKLEI K           111

SEQ ID NO: 6              moltype = AA   length = 111
FEATURE                   Location/Qualifiers
REGION                    1..111
                          note = Synthetic
source                    1..111
                          mol_type = protein
                          organism = synthetic construct
SEQUENCE: 6
EIVLTQSPAT LSLSPGERAT LSCRADERVS SSTYSYMHWY QQKPGQAPRL LIYDASNRAT  60
GIPARFSGSG SGTDFTLTIS SLEPEDFAVY YCQHSWEIPP TFGQGTKLEI K           111

SEQ ID NO: 7              moltype = AA   length = 111
FEATURE                   Location/Qualifiers
REGION                    1..111
                          note = Synthetic
source                    1..111
                          mol_type = protein
                          organism = synthetic construct
SEQUENCE: 7
EIVLTQSPAT LSLSPGERAT LSCRASQRVS SSTYSYMHWY QQKPGQAPRL LIKYASNRET  60
GIPARFSGSG SGTDFTLTIS SLEPEDFAVY YCQHSWEIPP TFGQGTKLEI K           111

SEQ ID NO: 8              moltype = AA   length = 111
FEATURE                   Location/Qualifiers
REGION                    1..111
                          note = Synthetic
source                    1..111
                          mol_type = protein
                          organism = synthetic construct
SEQUENCE: 8
EIVLTQSPAT LSLSPGERAT LSCRADERVS SSTYSYMHWY QQKPGQAPRL LIKYASNRET  60
GIPARFSGSG SGTDFTLTIS SLEPEDFAVY YCQHSWEIPP TFGQGTKLEI K           111

SEQ ID NO: 9              moltype = AA   length = 5
FEATURE                   Location/Qualifiers
REGION                    1..5
                          note = Synthetic
```

-continued

```
source                    1..5
                          mol_type = protein
                          organism = synthetic construct
SEQUENCE: 9
SYYMY                                                                      5

SEQ ID NO: 10             moltype = AA  length = 17
FEATURE                   Location/Qualifiers
REGION                    1..17
                          note = Synthetic
source                    1..17
                          mol_type = protein
                          organism = synthetic construct
SEQUENCE: 10
EINPSNGDTN YAQKFQG                                                         17

SEQ ID NO: 11             moltype = AA  length = 19
FEATURE                   Location/Qualifiers
REGION                    1..19
                          note = Synthetic
source                    1..19
                          mol_type = protein
                          organism = synthetic construct
SEQUENCE: 11
EINPSNGDTN YAEKFKGRV                                                       19

SEQ ID NO: 12             moltype = AA  length = 19
FEATURE                   Location/Qualifiers
REGION                    1..19
                          note = Synthetic
source                    1..19
                          mol_type = protein
                          organism = synthetic construct
SEQUENCE: 12
EINPSNGDTN YAEKFKGRA                                                       19

SEQ ID NO: 13             moltype = AA  length = 17
FEATURE                   Location/Qualifiers
REGION                    1..17
                          note = Synthetic
source                    1..17
                          mol_type = protein
                          organism = synthetic construct
SEQUENCE: 13
EINPSNGDTN FAEKFKG                                                         17

SEQ ID NO: 14             moltype = AA  length = 17
FEATURE                   Location/Qualifiers
REGION                    1..17
                          note = Synthetic
source                    1..17
                          mol_type = protein
                          organism = synthetic construct
SEQUENCE: 14
EINPSNGDTN YAEKFKG                                                         17

SEQ ID NO: 15             moltype = AA  length = 9
FEATURE                   Location/Qualifiers
REGION                    1..9
                          note = Synthetic
source                    1..9
                          mol_type = protein
                          organism = synthetic construct
SEQUENCE: 15
SDGRNDMDS                                                                  9

SEQ ID NO: 16             moltype = AA  length = 15
FEATURE                   Location/Qualifiers
REGION                    1..15
                          note = Synthetic
source                    1..15
                          mol_type = protein
                          organism = synthetic construct
SEQUENCE: 16
RASQRVSSST YSYMH                                                           15

SEQ ID NO: 17             moltype = AA  length = 15
FEATURE                   Location/Qualifiers
REGION                    1..15
```

-continued

```
                           note = Synthetic
source                     1..15
                           mol_type = protein
                           organism = synthetic construct
SEQUENCE: 17
RADERVSSST YSYMH                                                      15

SEQ ID NO: 18              moltype = AA   length = 7
FEATURE                    Location/Qualifiers
REGION                     1..7
                           note = Synthetic
source                     1..7
                           mol_type = protein
                           organism = synthetic construct
SEQUENCE: 18
DASNRAT                                                               7

SEQ ID NO: 19              moltype = AA   length = 7
FEATURE                    Location/Qualifiers
REGION                     1..7
                           note = Synthetic
source                     1..7
                           mol_type = protein
                           organism = synthetic construct
SEQUENCE: 19
YASNRET                                                               7

SEQ ID NO: 20              moltype = AA   length = 9
FEATURE                    Location/Qualifiers
REGION                     1..9
                           note = Synthetic
source                     1..9
                           mol_type = protein
                           organism = synthetic construct
SEQUENCE: 20
QHSWEIPPT                                                             9

SEQ ID NO: 21              moltype = AA   length = 232
FEATURE                    Location/Qualifiers
REGION                     1..232
                           note = Synthetic
source                     1..232
                           mol_type = protein
                           organism = synthetic construct
SEQUENCE: 21
EPKSCDKTHT CPPCPAPELL GGSSVFLFPP KPKDTLMISR TPEVTCVVVD VSHEDPEVKF     60
NWYVDGVEVH NAKTKPREEQ YGSTYRVVSV LTVLHQDWLN GKEYKCKVSN KALPAPIEKT    120
ISKAKGQPRE PQVYTLPPSR DELTKNQVSL TCLVKGFYPS DIAVEWESNG QPENNYKTTP    180
PVLDSDGSFF LYSKLTVDKS RWQQGNVFSC SVMHEALHNH YTQKSLSLSP GK            232

SEQ ID NO: 22              moltype = AA   length = 329
FEATURE                    Location/Qualifiers
REGION                     1..329
                           note = Synthetic
source                     1..329
                           mol_type = protein
                           organism = synthetic construct
SEQUENCE: 22
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPELLGG    120
PSVFLFPPKP KDTLMISRTP EVTCVVVAVS HEDPEVKFNW YVDGVEVHNA KTKPREEQYA    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSM HEALHNHYT QKSLSLSPG                                       329

SEQ ID NO: 23              moltype = AA   length = 329
FEATURE                    Location/Qualifiers
REGION                     1..329
                           note = Synthetic
source                     1..329
                           mol_type = protein
                           organism = synthetic construct
SEQUENCE: 23
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP SCPAPEFLGG    120
PSVFLFPPKP KDTLMISRTP EVTCVVVDVS QEDPEVQFNW YVDGVEVHNA KTKPREEQFN    180
SKYRVVSVLT VLHQDWLNGK EYKCKVSNKG LPSSIEKTIS KAKGQPREPQ VYTLPPSREE    240
MTKNQVSLSC AVKGFYPSDI AVEWESNGQP ENNYKTTPPV LDSDGSFFLV SKLTVDKSRW    300
QQGNVFSCSV MHEALHNHYT QKSLSLSPG                                      329
```

```
SEQ ID NO: 24           moltype = AA   length = 326
FEATURE                 Location/Qualifiers
REGION                  1..326
                        note = Synthetic
source                  1..326
                        mol_type = protein
                        organism = synthetic construct
SEQUENCE: 24
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APEFLGGPSV   120
FLFPPKPKDT LMISRTPEVT CVVVDVSQED PEVQFNWYVD GVEVHNAKTK PREEQFNSKY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLG                                       326

SEQ ID NO: 25           moltype = AA   length = 107
FEATURE                 Location/Qualifiers
REGION                  1..107
                        note = Synthetic
source                  1..107
                        mol_type = protein
                        organism = synthetic construct
SEQUENCE: 25
RTVAAPSVFI FPPSDEQLKS GTASVVCLLN NFYPREAKVQ WKVDNALQSG NSQESVTEQD   60
SKDSTYSLSS TLTLSKADYE KHKVYACEVT HQGLSSPVTK SFNRGEC                 107

SEQ ID NO: 26           moltype = DNA   length = 354
FEATURE                 Location/Qualifiers
misc_feature            1..354
                        note = Synthetic
source                  1..354
                        mol_type = other DNA
                        organism = synthetic construct
SEQUENCE: 26
gaggtgcagc tggtgcagtc cggcgccgag gtgaagaagc ccggcgcctc cgtgaaggtg   60
tcctgcaagg cctccggcta caccttcacc tcctactaca tgtactgggt gaggcaggcc   120
cccggccagg gcctggagtg gatgggcgag atcaacccct ccaacggcga caccaactac   180
gcacagaagt tccagggtag ggtcaccatg accgtggaca cgtccacctc caccgtctac   240
atggagctgt cctccctgag gtccgaggac accgccgtgt actactcgcg caggtccgac   300
ggcaggaacg acatggactc ctggggccag ggcaccctgg tgaccgtgtc ctcc         354

SEQ ID NO: 27           moltype = DNA   length = 354
FEATURE                 Location/Qualifiers
misc_feature            1..354
                        note = Synthetic
source                  1..354
                        mol_type = other DNA
                        organism = synthetic construct
SEQUENCE: 27
gaggtgcagc tggtgcagtc cggcgccgag gtgaagaagc ccggcgcctc cgtgaaggtg   60
tcctgcaagg cctccggcta catcttcacc tcctactaca tgtactgggt gaggcaggcc   120
cccggccagg gcctggagtg gatgggcgag atcaacccct ccaacggcga caccaactac   180
gcagagaagt tcaaggggtag ggtcaccatg accgtggaca cgtccacctc caccgtctac   240
atggagctgt cctccctgag gtccgaggac accgccgtgt actactcgcac caggtccgac   300
ggcaggaacg acatggactc ctggggccag ggcaccctgg tgaccgtgtc ctcc         354

SEQ ID NO: 28           moltype = DNA   length = 354
FEATURE                 Location/Qualifiers
misc_feature            1..354
                        note = Synthetic
source                  1..354
                        mol_type = other DNA
                        organism = synthetic construct
SEQUENCE: 28
gaggtgcagc tggtgcagtc cggcgccgag gtgaagaagc ccggcgcctc cgtgaaggtg   60
tcctgcaagg cctccggcta catcttcacc tcctactaca tgtactgggt gaggcaggcc   120
cccggccagg gcctggagtg gatcggcgag atcaacccct ccaacggcga caccaactac   180
gcagagaagt tcaaggggtag ggccaccctg accgtggaca cgtccacctc caccgtctac   240
atggagctgt cctccctgag gtccgaggac accgccgtgt actactcgcac caggtccgac   300
ggcaggaacg acatggactc ctggggccag ggcaccctgg tgaccgtgtc ctcc         354

SEQ ID NO: 29           moltype = DNA   length = 354
FEATURE                 Location/Qualifiers
misc_feature            1..354
                        note = Synthetic
source                  1..354
                        mol_type = other DNA
                        organism = synthetic construct
```

```
SEQUENCE: 29
caggtgcagc tggtgcagtc cggcgccgag gtgaagaagc ccggcgcctc cgtgaaggtg    60
tcctgcaagg cctccggcta catcttcacc tcctactaca tgtactgggt gaggcaggcc   120
cccggccagg gctggagtg gatcggcgag atcaacccct ccaacggcga caccaacttc    180
gcagagaagt tcaagggtag ggccaccctg accgtgaca cgtccaccctc caccgtctac   240
atggagctgt cctccctgag gtccgaggac accgccgtgt actactgcac caggtccgac   300
ggcaggaacg acatggactc ctggggccag ggcaccctgg tgaccgtgtc ctcc         354

SEQ ID NO: 30            moltype = DNA   length = 333
FEATURE                  Location/Qualifiers
misc_feature            1..333
                         note = Synthetic
source                   1..333
                         mol_type = other DNA
                         organism = synthetic construct SEQUENCE: 30
gagatcgtgc tgacccagtc acctgccacc ctgtccctgt cacctggaga gagagccacc    60
ctctcctgca gagcctccca gagggtgtcc tcctccacct actcctacat gcactggtac   120
cagcagaagc ctggacaggc acctaggctg ctgatctacg acgcctccaa cagggcgacc    180
ggtataccag ccaggttctc aggctcaggc tcaggcaccg acttcaccct gaccatctcc    240
tccctggagc cagaggactt cgccgtctac tactgccagc actcctggga gatcccacct    300
accttcggac aaggcaccaa gctggaaatc aaa                               333

SEQ ID NO: 31            moltype = DNA   length = 333
FEATURE                  Location/Qualifiers
misc_feature            1..333
                         note = Synthetic
source                   1..333
                         mol_type = other DNA
                         organism = synthetic construct SEQUENCE: 31
gagatcgtgc tgacccagtc acctgccacc ctgtccctgt cacctggaga gagagccacc    60
ctctcctgca gagccgatga gagggtgtcc tcctccacct actcctacat gcactggtac   120
cagcagaagc ctggacaggc acctaggctg ctgatctacg acgcctccaa cagggcgacc    180
ggtataccag ccaggttctc aggctcaggc tcaggcaccg acttcaccct gaccatctcc    240
tccctggagc cagaggactt cgccgtctac tactgccagc actcctggga gatcccacct    300
accttcggac aaggcaccaa gctggaaatc aaa                               333

SEQ ID NO: 32            moltype = DNA   length = 333
FEATURE                  Location/Qualifiers
misc_feature            1..333
                         note = Synthetic
source                   1..333
                         mol_type = other DNA
                         organism = synthetic construct SEQUENCE: 32
gagatcgtgc tgacccagtc acctgccacc ctgtccctgt cacctggaga gagagccacc    60
ctctcctgca gagcctccca gagggtgtcc tcctccacct actcctacat gcactggtac   120
cagcagaagc ctggacaggc acctaggctg ctgatcaagt acgcctccaa cagggagacc    180
ggtataccag ccaggttctc aggctcaggc tcaggcaccg acttcaccct gaccatctcc    240
tccctggagc cagaggactt cgccgtctac tactgccagc actcctggga gatcccacct    300
accttcggac aaggcaccaa gctggaaatc aaa                               333

SEQ ID NO: 33            moltype = DNA   length = 333
FEATURE                  Location/Qualifiers
misc_feature            1..333
                         note = Synthetic
source                   1..333
                         mol_type = other DNA
                         organism = synthetic construct SEQUENCE: 33
gagatcgtgc tgacccagtc acctgccacc ctgtccctgt cacctggaga gagagccacc    60
ctctcctgca gagccgatga gagggtgtcc tcctccacct actcctacat gcactggtac   120
cagcagaagc ctggacaggc acctaggctg ctgatcaagt acgcctccaa cagggagacc    180
ggtataccag ccaggttctc aggctcaggc tcaggcaccg acttcaccct gaccatctcc    240
tccctggagc cagaggactt cgccgtctac tactgccagc actcctggga gatcccacct    300
accttcggac aaggcaccaa gctggaaatc aaa                               333

SEQ ID NO: 34            moltype = AA   length = 374
FEATURE                  Location/Qualifiers
REGION                   1..374
                         note = Synthetic
source                   1..374
                         mol_type = protein
                         organism = synthetic construct SEQUENCE: 34
MWFLTTLLLW VPVDGQVDTT KAVITLQPPW VSVFQEETVT LHCEVLHLPG SSSTQWFLNG    60
TATQTSTPSY RITSASVNDS GEYRCQRGLS GRSDPIQLEI HRGWLLLQVS SRVFTEGEPL   120
ALRCHAWKDK LVYNVLYYRN GKAFKFFHWN SNLTILKTNI SHNGTYHCSG MGKHRYTSAG   180
```

-continued

```
ISVTVKELFP APVLNASVTS PLLEGNLVTL SCETKLLLQR PGLQLYFSFY MGSKTLRGRN   240
TSSEYQILTA RREDSGLYWC EAATEDGNVL KRSPELELQV LGLQLPTPVW FHVLFYLAVG   300
IMFLVNTVLW VTIRKELKRK KKWDLEISLD SGHEKKVISS LQEDRHLEEE LKCQEQKEEQ   360
LQEGVHRKEP QGAT                                                    374

SEQ ID NO: 35              moltype = AA   length = 316
FEATURE                    Location/Qualifiers
REGION                     1..316
                           note = Synthetic
source                     1..316
                           mol_type = protein
                           organism = synthetic construct
SEQUENCE: 35
MTMETQMSQN VCPRNLWLLQ PLTVLLLLAS ADSQAAPPKA VLKLEPPWIN VLQEDSVTLT    60
CQGARSPESD SIQWFHNGNL IPTHTQPSYR FKANNNDSGE YTCQTGQTSL SDPVHLTVLS   120
EWLVLQTPHL EFQEGETIML RCHSWKDKPL VKVTFFQNGK SQKFSHLDPT FSIPQANHSH   180
SGDYHCTGNI GYTLFSSKPV TITVQVPSMG SSSPMGVIVA VVIATAVAAI VAAVVALIYC   240
RKKRISANST DPVKAAQFEP PGRQMIAIRK RQLEETNNDY ETADGGYMTL NPRAPTDDDK   300
NIYLTLPPND HVNSNN                                                  316

SEQ ID NO: 36              moltype = AA   length = 290
FEATURE                    Location/Qualifiers
REGION                     1..290
                           note = Synthetic
source                     1..290
                           mol_type = protein
                           organism = synthetic construct
SEQUENCE: 36
MGGGAGERLF TSSCLVGLVP LGLRISLVTC PLQCGIMWQL LLPTALLLLV SAGMRTEDLP    60
KAVVFLEPQW YRVLEKDSVT LKCQGAYSPE DNSTQWFHNE SLISSQASSY FIDAATVDDS   120
GEYRCQTNLS TLSDPVQLEV HIGWLLLQAP RWVFKEEDPI HLRCHSWKNT ALHKVTYLQN   180
GKGRKYFHHN SDFYIPKATL KDSGSYFCRG LVGSKNVSSE TVNITITQGL AVSTISSFFP   240
PGYQVSFCLV MVLLFAVDTG LYFSVKTNIR SSTRDWKDHK FKWRKDPQDK             290

SEQ ID NO: 37              moltype = AA   length = 233
FEATURE                    Location/Qualifiers
REGION                     1..233
                           note = Synthetic
source                     1..233
                           mol_type = protein
                           organism = synthetic construct
SEQUENCE: 37
MWQLLLPTAL LLLVSAGMRT EDLPKAVVFL EPQWYSVLEK DSVTLKCQGA YSPEDNSTQW    60
FHNESLISSQ ASSYFIDAAT VNDSGEYRCQ TNLSTLSDPV QLEVHIGWLL LQAPRWVFKE   120
EDPIHLRCHS WKNTALHKVT YLQNGKDRKY FHHNSDFHIP KATLKDSGSY FCRGLVGSKN   180
VSSETVNITI TQGLAVSTIS SFSPPGYQVS FCLVMVLLFA VDTGLYFSVK TNI         233

SEQ ID NO: 38              moltype = AA   length = 218
FEATURE                    Location/Qualifiers
REGION                     1..218
                           note = Synthetic
source                     1..218
                           mol_type = protein
                           organism = synthetic construct
SEQUENCE: 38
EIVLTQSPAT LSLSPGERAT LSCRASQRVS SSTYSYMHWY QQKPGQAPRL LIYDASNRAT    60
GIPARFSGSG SGTDFTLTIS SLEPEDFAVY YCQHSWEIPP TFGQGTKLEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                          218

SEQ ID NO: 39              moltype = AA   length = 218
FEATURE                    Location/Qualifiers
REGION                     1..218
                           note = Synthetic
source                     1..218
                           mol_type = protein
                           organism = synthetic construct
SEQUENCE: 39
EIVLTQSPAT LSLSPGERAT LSCRADERVS SSTYSYMHWY QQKPGQAPRL LIYDASNRAT    60
GIPARFSGSG SGTDFTLTIS SLEPEDFAVY YCQHSWEIPP TFGQGTKLEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                          218

SEQ ID NO: 40              moltype = AA   length = 218
FEATURE                    Location/Qualifiers
REGION                     1..218
                           note = Synthetic
source                     1..218
                           mol_type = protein
```

-continued

```
                          organism = synthetic construct
SEQUENCE: 40
EIVLTQSPAT LSLSPGERAT LSCRASQRVS SSTYSYMHWY QQKPGQAPRL LIKYASNRET    60
GIPARFSGSG SGTDFTLTIS SLEPEDFAVY YCQHSWEIPP TFGQGTKLEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 41              moltype = AA  length = 218
FEATURE                    Location/Qualifiers
REGION                     1..218
                           note = Synthetic
source                     1..218
                           mol_type = protein
                           organism = synthetic construct
SEQUENCE: 41
EIVLTQSPAT LSLSPGERAT LSCRADERVS SSTYSYMHWY QQKPGQAPRL LIKYASNRET    60
GIPARFSGSG SGTDFTLTIS SLEPEDFAVY YCQHSWEIPP TFGQGTKLEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 42              moltype = AA  length = 232
FEATURE                    Location/Qualifiers
REGION                     1..232
                           note = Synthetic
source                     1..232
                           mol_type = protein
                           organism = synthetic construct
SEQUENCE: 42
EPKSCDKTHT CPPCPAPELL GGSSVFLFPP KPKDTLMISR TPEVTCVVVD VSHEDPEVKF    60
NWYVDGVEVH NAKTKPREEQ YGSTYRVVSV LTVLHQDWLN GKEYKCKVSN KALPAPIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 43              moltype = AA  length = 232
FEATURE                    Location/Qualifiers
REGION                     1..232
                           note = Synthetic
source                     1..232
                           mol_type = protein
                           organism = synthetic construct
SEQUENCE: 43
EPKSCDKTHT CPPCPAPELL GGSSVFLFPP KPKDTLMISR TPEVTCVVVD VSHEDPEVKF    60
NWYVDGVEVH NAKTKPREEQ YGSTYRVVSV LTVLHQDWLN GKEYKCKVSN KALPAPIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 44              moltype = AA  length = 232
FEATURE                    Location/Qualifiers
REGION                     1..232
                           note = Synthetic
source                     1..232
                           mol_type = protein
                           organism = synthetic construct
SEQUENCE: 44
EPKSCDKTHT CPPCPAPELL GGSSVFLFPP KPKDTLMISR TPEVTCVVVD VSHEDPEVKF    60
NWYVDGVEVH NAKTKPREEQ YGSTYRVVSV LTVLHQDWLN GKEYKCKVSN KALPAPIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 45              moltype = AA  length = 232
FEATURE                    Location/Qualifiers
REGION                     1..232
                           note = Synthetic
source                     1..232
                           mol_type = protein
                           organism = synthetic construct
SEQUENCE: 45
EPKSCDKTHT CPPCPAPELL GGSSVFLFPP KPKDTLMISR TPEVTCVVVD VSHEDPEVKF    60
NWYVDGVEVH NAKTKPREEQ YGSTYRVVSV LTVLHQDWLN GKEYKCKVSN KALPAPIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 46              moltype = AA  length = 447
FEATURE                    Location/Qualifiers
REGION                     1..447
                           note = Synthetic
source                     1..447
                           mol_type = protein
                           organism = synthetic construct
```

```
SEQUENCE: 46
EVQLVQSGAE VKKPGASVKV SCKASGYTFT SYYMYWVRQA PGQGLEWMGE INPSNGDTNY  60
AQKFQGRVTM TVDTSTSTVY MELSSLRSED TAVYYCARSD GRNDMDSWGQ GTLVTVSSAS 120
TKGPSVFPLA PSSKSTSGGT AALGCLVKDY FPEPVTVSWN SGALTSGVHT FPAVLQSSGL 180
YSLSSVVTVP SSSLGTQTYI CNVNHKPSNT KVDKKVEPKS CDKTHTCPPC PAPELLGGPS 240
VFLFPPKPKD TLMISRTPEV TCVVVAVSHE DPEVKFNWYV DGVEVHNAKT KPREEQYAST 300
YRVVSVLTVL HQDWLNGKEY KCKVSNKALP APIEKTISKA KGQPREPQVY TLPPSRDELT 360
KNQVSLTCLV KGFYPSDIAV EWESNGQPEN NYKTTPPVLD SDGSFFLYSK LTVDKSRWQQ 420
GNVFSCSVMH EALHNHYTQK SLSLSPG                                    447

SEQ ID NO: 47          moltype = AA  length = 447
FEATURE                Location/Qualifiers
REGION                 1..447
                       note = Synthetic
source                 1..447
                       mol_type = protein
                       organism = synthetic construct
SEQUENCE: 47
EVQLVQSGAE VKKPGASVKV SCKASGYIFT SYYMYWVRQA PGQGLEWMGE INPSNGDTNY  60
AEKFKGRVTM TVDTSTSTVY MELSSLRSED TAVYYCTRSD GRNDMDSWGQ GTLVTVSSAS 120
TKGPSVFPLA PSSKSTSGGT AALGCLVKDY FPEPVTVSWN SGALTSGVHT FPAVLQSSGL 180
YSLSSVVTVP SSSLGTQTYI CNVNHKPSNT KVDKKVEPKS CDKTHTCPPC PAPELLGGPS 240
VFLFPPKPKD TLMISRTPEV TCVVVAVSHE DPEVKFNWYV DGVEVHNAKT KPREEQYAST 300
YRVVSVLTVL HQDWLNGKEY KCKVSNKALP APIEKTISKA KGQPREPQVY TLPPSRDELT 360
KNQVSLTCLV KGFYPSDIAV EWESNGQPEN NYKTTPPVLD SDGSFFLYSK LTVDKSRWQQ 420
GNVFSCSVMH EALHNHYTQK SLSLSPG                                    447

SEQ ID NO: 48          moltype = AA  length = 447
FEATURE                Location/Qualifiers
REGION                 1..447
                       note = Synthetic
source                 1..447
                       mol_type = protein
                       organism = synthetic construct
SEQUENCE: 48
EVQLVQSGAE VKKPGASVKV SCKASGYIFT SYYMYWVRQA PGQGLEWIGE INPSNGDTNY  60
AEKFKGRATL TVDTSTSTVY MELSSLRSED TAVYYCTRSD GRNDMDSWGQ GTLVTVSSAS 120
TKGPSVFPLA PSSKSTSGGT AALGCLVKDY FPEPVTVSWN SGALTSGVHT FPAVLQSSGL 180
YSLSSVVTVP SSSLGTQTYI CNVNHKPSNT KVDKKVEPKS CDKTHTCPPC PAPELLGGPS 240
VFLFPPKPKD TLMISRTPEV TCVVVAVSHE DPEVKFNWYV DGVEVHNAKT KPREEQYAST 300
YRVVSVLTVL HQDWLNGKEY KCKVSNKALP APIEKTISKA KGQPREPQVY TLPPSRDELT 360
KNQVSLTCLV KGFYPSDIAV EWESNGQPEN NYKTTPPVLD SDGSFFLYSK LTVDKSRWQQ 420
GNVFSCSVMH EALHNHYTQK SLSLSPG                                    447

SEQ ID NO: 49          moltype = AA  length = 447
FEATURE                Location/Qualifiers
REGION                 1..447
                       note = Synthetic
source                 1..447
                       mol_type = protein
                       organism = synthetic construct
SEQUENCE: 49
QVQLVQSGAE VKKPGASVKV SCKASGYIFT SYYMYWVRQA PGQGLEWIGE INPSNGDTNF  60
AEKFKGRATL TVDTSTSTVY MELSSLRSED TAVYYCTRSD GRNDMDSWGQ GTLVTVSSAS 120
TKGPSVFPLA PSSKSTSGGT AALGCLVKDY FPEPVTVSWN SGALTSGVHT FPAVLQSSGL 180
YSLSSVVTVP SSSLGTQTYI CNVNHKPSNT KVDKKVEPKS CDKTHTCPPC PAPELLGGPS 240
VFLFPPKPKD TLMISRTPEV TCVVVAVSHE DPEVKFNWYV DGVEVHNAKT KPREEQYAST 300
YRVVSVLTVL HQDWLNGKEY KCKVSNKALP APIEKTISKA KGQPREPQVY TLPPSRDELT 360
KNQVSLTCLV KGFYPSDIAV EWESNGQPEN NYKTTPPVLD SDGSFFLYSK LTVDKSRWQQ 420
GNVFSCSVMH EALHNHYTQK SLSLSPG                                    447

SEQ ID NO: 50          moltype = AA  length = 447
FEATURE                Location/Qualifiers
REGION                 1..447
                       note = Synthetic
source                 1..447
                       mol_type = protein
                       organism = synthetic construct
SEQUENCE: 50
EVQLVQSGAE VKKPGASVKV SCKASGYTFT SYYMYWVRQA PGQGLEWMGE INPSNGDTNY  60
AQKFQGRVTM TVDTSTSTVY MELSSLRSED TAVYYCARSD GRNDMDSWGQ GTLVTVSSAS 120
TKGPSVFPLA PSSKSTSGGT AALGCLVKDY FPEPVTVSWN SGALTSGVHT FPAVLQSSGL 180
YSLSSVVTVP SSSLGTQTYI CNVNHKPSNT KVDKKVEPKS CDKTHTCPSC PAPEFLGGPS 240
VFLFPPKPKD TLMISRTPEV TCVVVDVSQE DPEVQFNWYV DGVEVHNAKT KPREEQFNSK 300
YRVVSVLTVL HQDWLNGKEY KCKVSNKGLP SSIEKTISKA KGQPREPQVY TLPPSREEMT 360
KNQVSLSCAV KGFYPSDIAV EWESNGQPEN NYKTTPPVLD SDGSFFLVSK LTVDKSRWQQ 420
GNVFSCSVMH EALHNHYTQK SLSLSPG                                    447

SEQ ID NO: 51          moltype = AA  length = 447
```

```
FEATURE              Location/Qualifiers
REGION               1..447
                     note = Synthetic
source               1..447
                     mol_type = protein
                     organism = synthetic construct
SEQUENCE: 51
EVQLVQSGAE VKKPGASVKV SCKASGYIFT SYYMYWVRQA PGQGLEWMGE INPSNGDTNY   60
AEKFKGRVTM TVDTSTSTVY MELSSLRSED TAVYYCTRSD GRNDMDSWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPSC PAPEFLGGPS  240
VFLFPPKPKD TLMISRTPEV TCVVVDVSQE DPEVQFNWYV DGVEVHNAKT KPREEQFNSK  300
YRVVSVLTVL HQDWLNGKEY KCKVSNKGLP SSIEKTISKA KGQPREPQVY TLPPSREEMT  360
KNQVSLSCAV KGFYPSDIAV EWESNGQPEN NYKTTPPVLD SDGSFFLVSK LTVDKSRWQQ  420
GNVFSCSVMH EALHNHYTQK SLSLSPG                                      447

SEQ ID NO: 52          moltype = AA  length = 447
FEATURE              Location/Qualifiers
REGION               1..447
                     note = Synthetic
source               1..447
                     mol_type = protein
                     organism = synthetic construct
SEQUENCE: 52
EVQLVQSGAE VKKPGASVKV SCKASGYIFT SYYMYWVRQA PGQGLEWIGE INPSNGDTNY   60
AEKFKGRATL TVDTSTSTVY MELSSLRSED TAVYYCTRSD GRNDMDSWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPSC PAPEFLGGPS  240
VFLFPPKPKD TLMISRTPEV TCVVVDVSQE DPEVQFNWYV DGVEVHNAKT KPREEQFNSK  300
YRVVSVLTVL HQDWLNGKEY KCKVSNKGLP SSIEKTISKA KGQPREPQVY TLPPSREEMT  360
KNQVSLSCAV KGFYPSDIAV EWESNGQPEN NYKTTPPVLD SDGSFFLVSK LTVDKSRWQQ  420
GNVFSCSVMH EALHNHYTQK SLSLSPG                                      447

SEQ ID NO: 53          moltype = AA  length = 447
FEATURE              Location/Qualifiers
REGION               1..447
                     note = Synthetic
source               1..447
                     mol_type = protein
                     organism = synthetic construct
SEQUENCE: 53
QVQLVQSGAE VKKPGASVKV SCKASGYIFT SYYMYWVRQA PGQGLEWIGE INPSNGDTNF   60
AEKFKGRATL TVDTSTSTVY MELSSLRSED TAVYYCTRSD GRNDMDSWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPSC PAPEFLGGPS  240
VFLFPPKPKD TLMISRTPEV TCVVVDVSQE DPEVQFNWYV DGVEVHNAKT KPREEQFNSK  300
YRVVSVLTVL HQDWLNGKEY KCKVSNKGLP SSIEKTISKA KGQPREPQVY TLPPSREEMT  360
KNQVSLSCAV KGFYPSDIAV EWESNGQPEN NYKTTPPVLD SDGSFFLVSK LTVDKSRWQQ  420
GNVFSCSVMH EALHNHYTQK SLSLSPG                                      447

SEQ ID NO: 54          moltype = AA  length = 444
FEATURE              Location/Qualifiers
REGION               1..444
                     note = Synthetic
source               1..444
                     mol_type = protein
                     organism = synthetic construct
SEQUENCE: 54
EVQLVQSGAE VKKPGASVKV SCKASGYTFT SYYMYWVRQA PGQGLEWMGE INPSNGDTNY   60
AQKFQGRVTM TVDTSTSTVY MELSSLRSED TAVYYCARSD GRNDMDSWGQ GTLVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP EFLGGPSVFL  240
FPPKPKDTLM ISRTPEVTCV VVDVSQEDPE VQFNWYVDGV EVHNAKTKPR EEQFNSKYRV  300
VSVLTVLHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSRLTV DKSRWQEGNV  420
FSCSVMHEAL HNHYTQKSLS LSLG                                         444

SEQ ID NO: 55          moltype = AA  length = 444
FEATURE              Location/Qualifiers
REGION               1..444
                     note = Synthetic
source               1..444
                     mol_type = protein
                     organism = synthetic construct
SEQUENCE: 55
EVQLVQSGAE VKKPGASVKV SCKASGYIFT SYYMYWVRQA PGQGLEWMGE INPSNGDTNY   60
AEKFKGRVTM TVDTSTSTVY MELSSLRSED TAVYYCTRSD GRNDMDSWGQ GTLVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP EFLGGPSVFL  240
```

-continued

```
FPPKPKDTLM ISRTPEVTCV VVDVSQEDPE VQFNWYVDGV EVHNAKTKPR EEQFNSKYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVMHEAL HNHYTQKSLS LSLG                                        444

SEQ ID NO: 56           moltype = AA  length = 444
FEATURE                 Location/Qualifiers
REGION                  1..444
                        note = Synthetic
source                  1..444
                        mol_type = protein
                        organism = synthetic construct
SEQUENCE: 56
EVQLVQSGAE VKKPGASVKV SCKASGYIFT SYYMYWVRQA PGQGLEWIGE INPSNGDTNY   60
AEKFKGRATL TVDTSTSTVY MELSSLRSED TAVYYCTRSD GRNDMDSWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFLGGPSVFL   240
FPPKPKDTLM ISRTPEVTCV VVDVSQEDPE VQFNWYVDGV EVHNAKTKPR EEQFNSKYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVMHEAL HNHYTQKSLS LSLG                                        444

SEQ ID NO: 57           moltype = AA  length = 444
FEATURE                 Location/Qualifiers
REGION                  1..444
                        note = Synthetic
source                  1..444
                        mol_type = protein
                        organism = synthetic construct
SEQUENCE: 57
QVQLVQSGAE VKKPGASVKV SCKASGYIFT SYYMYWVRQA PGQGLEWIGE INPSNGDTNF   60
AEKFKGRATL TVDTSTSTVY MELSSLRSED TAVYYCTRSD GRNDMDSWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFLGGPSVFL   240
FPPKPKDTLM ISRTPEVTCV VVDVSQEDPE VQFNWYVDGV EVHNAKTKPR EEQFNSKYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVMHEAL HNHYTQKSLS LSLG                                        444
```

THERAPEUTIC ANTI-CD40 LIGAND ANTIBODIES

CROSS REFERENCE TO RELATED APPLICATIONS

This application is a continuation of U.S. application Ser. No. 16/615,757, filed Nov. 21, 2019, which is a 35 U.S.C. § 371 United States National Phase Application of, and claims priority to PCT Application No. PCT/US2018/034172, filed May 23, 2018, which claims priority to U.S. Provisional Application No. 62/510,471, filed May 24, 2017. The entire contents of the aforementioned disclosures are incorporated by reference.

SEQUENCE LISTING

This application incorporates by reference in its entirety the sequence listing entitled "SeqListing_ELDN008C1.XML" created on Nov. 20, 2019, at 3:15 pm, that is 84,560 bytes in size, and filed electronically herewith.

FIELD

Anti-CD40L antibodies, compositions comprising the antibodies, and method of using same for treatment of CD40L-related diseases or disorders.

BACKGROUND

The interaction of CD40 with its ligand CD40L plays a critical role in regulating immune responses. Binding of CD40L to CD40 triggers activation of the CD40 pathway which up-regulates costimulatory molecules such as CD80 and CD86. Blockade of the interaction between CD40 and CD40L by monoclonal antibodies has been shown to result in protection from autoimmunity and graft rejection in various preclinical models. Recently, in a mouse model of amyotrophic lateral sclerosis, an antibody directed to CD40L was shown to delay disease onset and prolong survival the onset of disease. (U.S. Pat. No. 8,435,514, hereby incorporated by reference). In early clinical studies, the humanized anti-CD40L antibody hu5c8 showed efficacy in patients with lupus and in patients with immune thrombocytopenic purpura. However, incidents of thromboembolism in the patients treated with hu5c8 halted further trials. Further in vitro and preclinical animal studies established that interaction of the Fc with the Fc receptor FcγRIIa caused platelet activation, and aggregation, that resulted in thromboembolic events. In addition, it has been reported that binding of the Fc to complement may reduce or prevent induction of immune tolerance. Various approaches have been taken to reduce or eliminate the interaction of the immunoglobulin Fc region with FcγRIIa, and/or to reduce or eliminate the interaction with complement, including introducing point mutation(s) in the Fc region to make anti-CD40L antibodies which lack Fc effector function. Other approaches use fragments of antibodies lacking the Fc region or antibodies that contain multiple amino acid substitutions in the Fc region. Although the anti-CD40L antibody, hu5c8, showed efficacy in human patients there is no anti-CD40L antibody on the market. Accordingly, there is a need for improved anti-CD40L antibodies for administration to humans that are efficacious and do not cause platelet activation or aggregation or bind to complement yet are stable and bind to CD40L.

SUMMARY

Novel antibody polypeptides and antigen binding fragments thereof, of the present invention provide such improved anti-CD40L antibodies. The following section only summarizes certain aspects of the present disclosure and is not intended to be limiting in nature. These aspects and other aspects and embodiments are described more fully below. All references cited in this specification are hereby incorporated by reference in their entirety. In the event of a discrepancy between the express disclosure of this specification and the references incorporated by reference, the express disclosure of this specification shall control.

The present invention provides isolated, engineered, non-naturally occurring antibodies and antigen binding fragments thereof, that bind human CD40L and block the binding of CD40 to CD40L. The antibody and antigen binding fragments thereof, are engineered to have the desired activity and binding. In some embodiments the antibody or antigen binding fragment thereof, are engineered to have decreased Fc effector function in comparison to some previous anti-CD40L antibodies. The antibodies and antigen binding fragments thereof as disclosed in the present application are useful in the treatment of diseases involving CD40L activation, including neurodegenerative or neuromuscular diseases or disorders, inflammatory or immune diseases or disorders and autoimmune diseases.

In one aspect the present disclosure provides isolated antibodies or antigen-binding fragments thereof that specifically binds to CD40L which comprise: (a) a heavy chain variable region ($V_H$) comprising; i) a CDRH1 domain comprising the sequence set forth in SEQ ID NO: 9; ii) a CDRH2 domain comprising the sequence set forth in SEQ ID NO: 10, 11, 12, 13, or 14; iii) a CDRH3 domain comprising the sequence set forth in SEQ ID NO: 15; and (b) a light chain variable region (VL) comprising: i) a CDRL1 domain comprising the sequence set forth in SEQ ID NO: 16 or 17; ii) a CDRL2 domain comprising the sequence set forth in SEQ ID NO: 18 or 19; and iii) a CDRL3 domain comprising the sequence set forth in SEQ ID NO: 20.

In some embodiments of the above aspect the present disclosure provides isolated antibodies or antigen-binding fragments thereof that specifically binds to CD40L which comprise: (a) a heavy chain variable region ($V_H$) comprising; i) a CDRH1 domain consisting of the sequence set forth in SEQ ID NO: 9; ii) a CDRH2 domain consisting of the sequence set forth in SEQ ID NO: 10, 11, 12, 13, or 14; iii) a CDRH3 domain consisting of the sequence set forth in SEQ ID NO: 15; and (b) a light chain variable region (VL) comprising: i) a CDRL1 domain consisting of the sequence set forth in SEQ ID NO: 16 or 17; ii) a CDRL2 domain consisting of the sequence set forth in SEQ ID NO: 18 or 19; and iii) a CDRL3 domain consisting of the sequence set forth in SEQ ID NO: 20.

The present disclosure also provides for isolated antibodies or antigen-binding fragments thereof that specifically binds to CD40L comprising: (a) a heavy chain variable region ($V_H$) having the amino acid sequence as set forth in SEQ ID NOs: 1, 2, 3, or 4: and (b) a light chain variable region (VL) having the amino acid sequence as set forth in SEQ ID NOs: 5, 6, 7, or 8.

In some embodiments the isolated antibody or antigen binding fragment thereof according to the disclosure comprises an Fc region and the Fc region has been engineered to reduce or eliminate one or more Fc effector function. In some embodiments the isolated antibodies are of the IgG1 isotype, and the heavy chain constant region comprises the amino acid sequence as set forth in SEQ ID NO: 21. In yet other embodiments the antibody comprises a heavy chain constant region wherein the heavy chain constant region comprises the amino acid sequence as set forth in SEQ ID NO: 22. In still other embodiments the antibody comprises a heavy chain constant region wherein the heavy chain constant region comprises the amino acid sequence as set forth in SEQ ID NO: 23. In another embodiment the antibody comprises a heavy chain constant region wherein the heavy chain constant region comprises the amino acid sequence as set forth in SEQ ID NO: 24.

Another aspect of the present disclosure provides for methods for treating a subject with a CD40L-associated disease or disorder comprising administering to the subject a therapeutically effective amount of an antibody or antibody fragment according to the present disclosure. In another aspect the present disclosure provides for methods for inhibiting an immune response in a subject comprising administering to the subject a therapeutically effective amount of an antibody or antibody fragment according to the present disclosure.

BRIEF DESCRIPTION OF THE DRAWING(S)

Figure 6A:
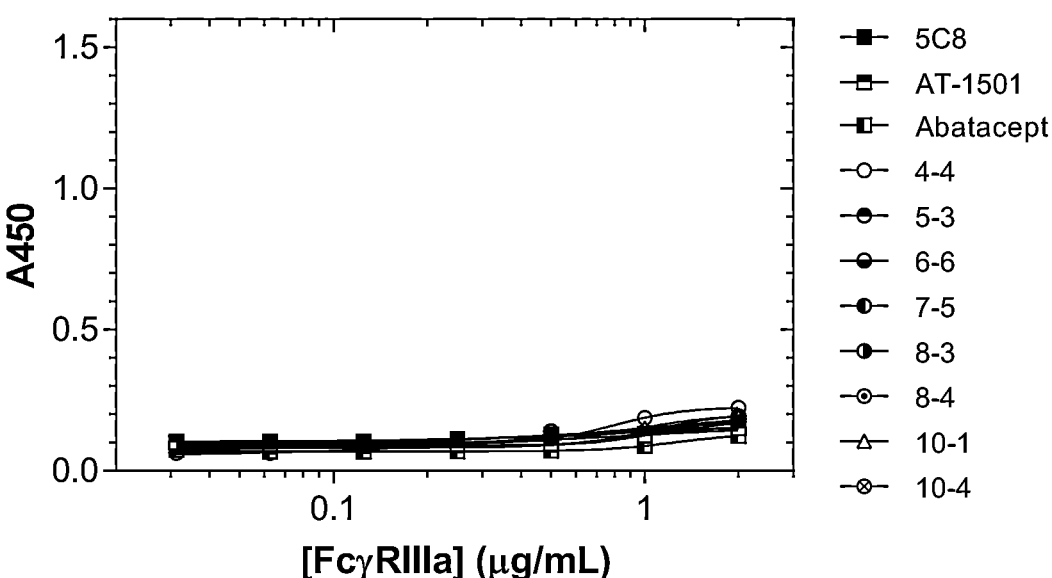
Figure 6B:
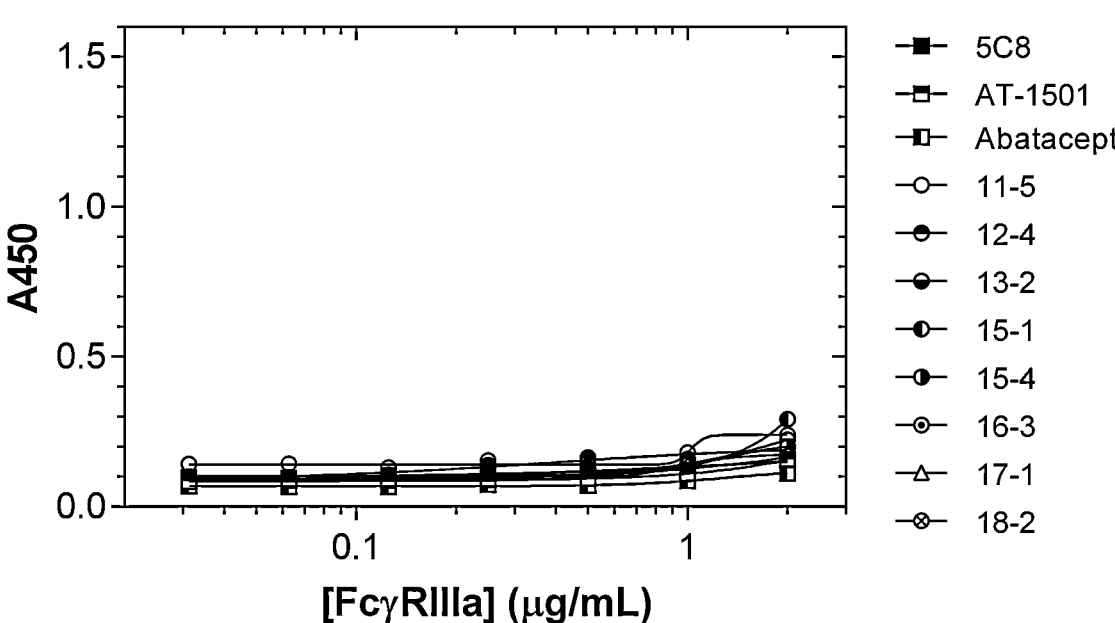
Figure 6C:
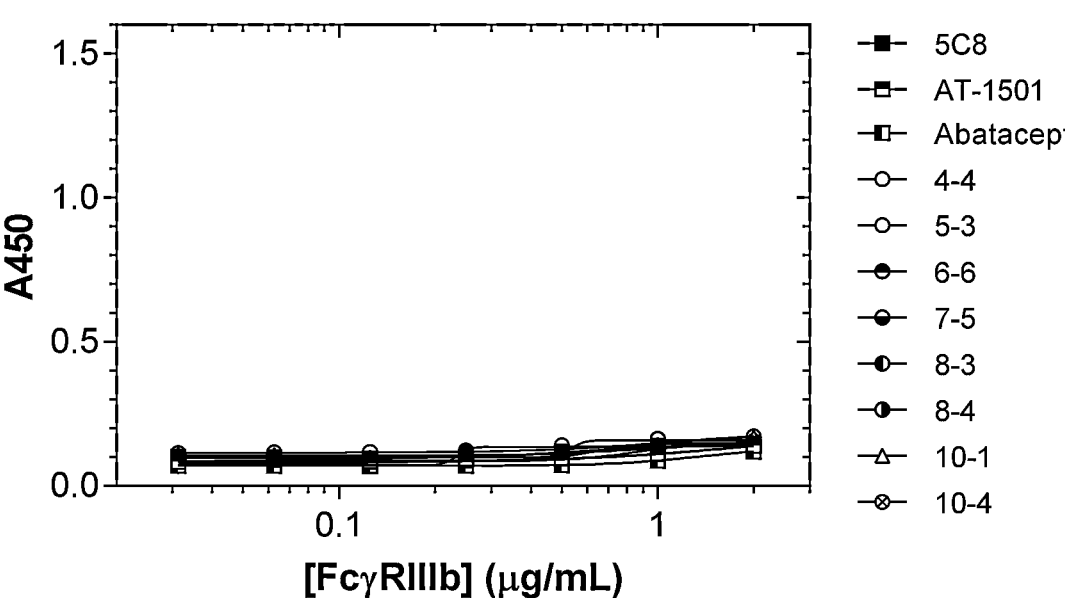
Figure 6D:
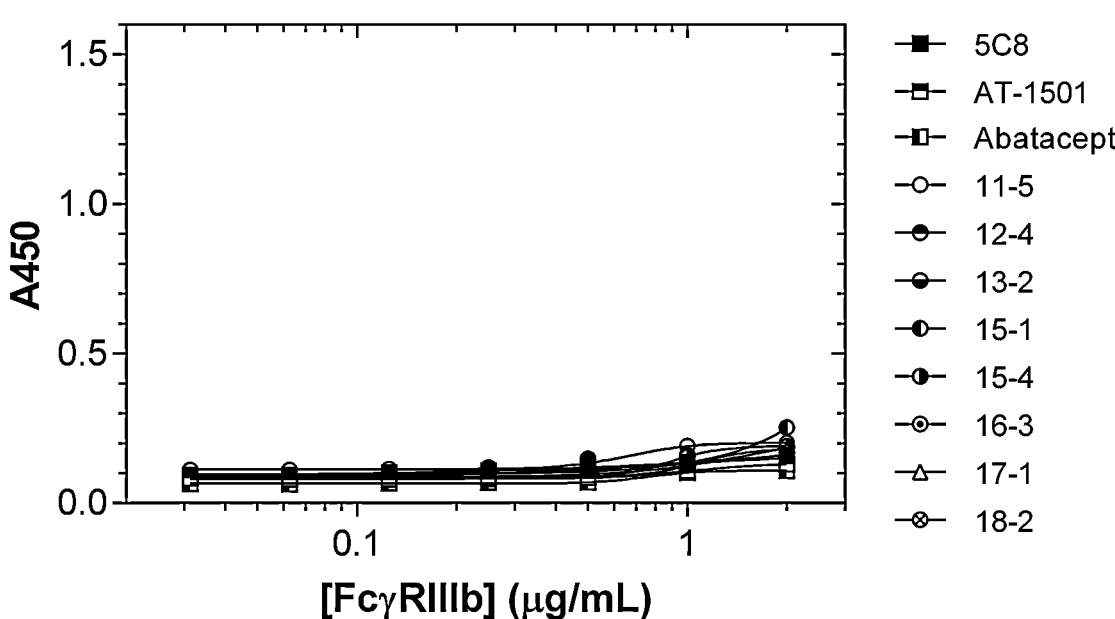

FIGS. 6A and 6B are graphs, each of which shows binding of eight of the antibody clones, 5c8, AT-1501 and abatacept to FcγRIIIa. None of the antibodies showed significant binding to FcγRIIIa. FIGS. 6C and 6D are graphs, each of which shows binding of eight of the antibody clones, 5c8, AT-1501 and abatacept to FcγRIIIb. None of the antibodies showed significant binding to FcγRIIIb.

Figure 7A:
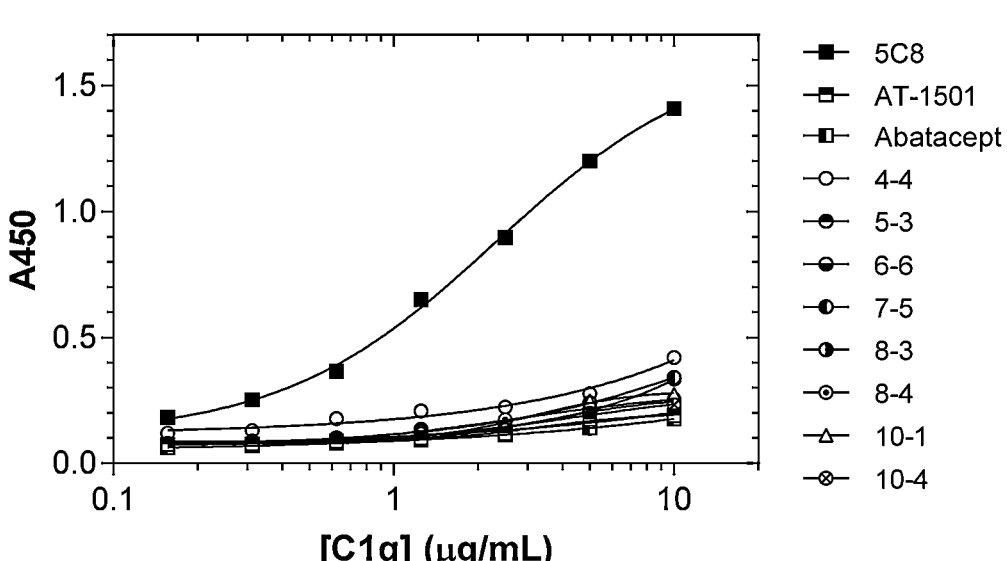
Figure 7B:
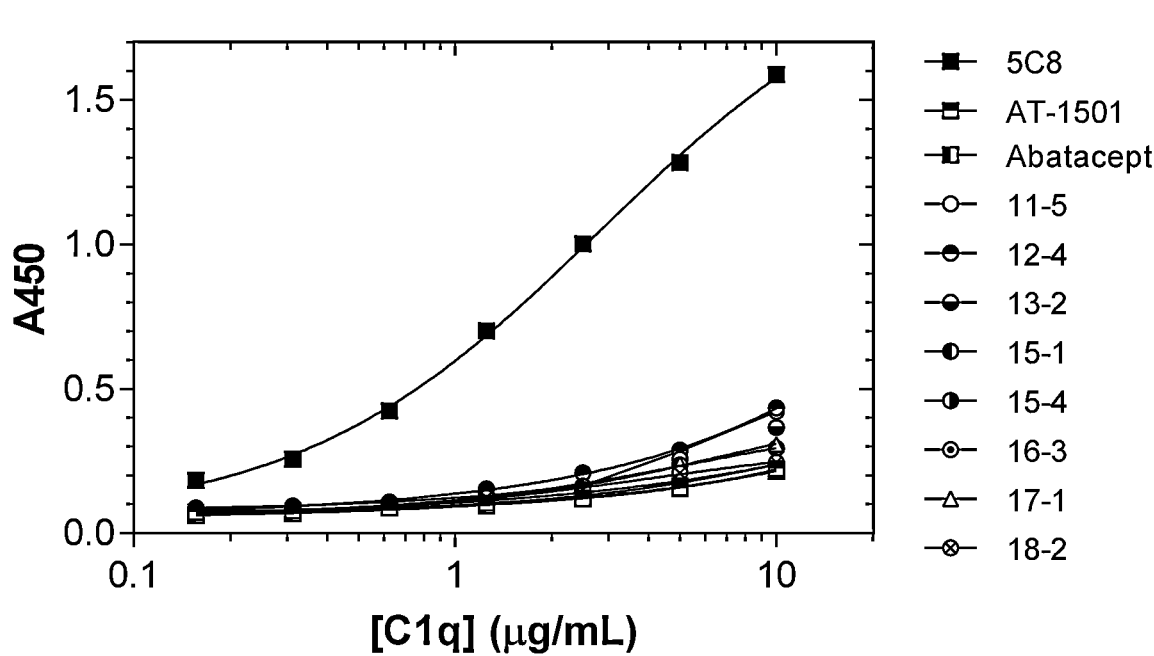

FIGS. 7A and 7B are graphs, each showing the binding of eight of the antibody clones, 5c8, AT-1501 and abatacept to C1q. The only antibody having significant binding to C1q was the 5c8 antibody.

DETAILED DESCRIPTION

Definitions

For convenience, the meaning of certain terms and phrases used in the specification, examples, and appended claims, are provided below.

The terms such as "comprises", "comprised", "comprising", "contains", "containing" and the like have the meaning attributed in United States patent law; these terms are inclusive or open-ended and do not exclude additional, unrecited elements or method steps. Terms such as "consisting essentially of" and "consists essentially of" have the meaning attributed to them in United States patent law; these terms allow for the inclusion of additional ingredients or steps that do not materially affect the basic and novel characteristics of the claim invention. The terms "consists of" and "consisting of" have the meaning ascribed to them in United States patent law; these terms are close ended.

TMB is an abbreviation of 3,3',5,5'-Tetramethylbenzidine.

"CDR domain" as used herein means an antibody complementary determining region with or without flanking sequences.

The invention illustratively described herein suitably may be practiced in the absence of any element or elements, limitation or limitations which is not specifically disclosed herein.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation. One effector function is ability of the Fc or constant region of an antibody to bind proteins including, but not limited to, an Fc receptor (FcR) (e.g., high affinity Fc region of IgG receptor Ia (FCγRIa) (CD64) (SEQ ID NO: 34), low affinity immunoglobulin gamma Fc region acceptor IIa (FCγRIIa) (CD32) (SEQ ID NO: 35), low affinity immunoglobulin gamma Fc region receptor Ma (FCγRIIIA) (CD16a) (SEQ ID NO: 36), low affinity immunoglobulin gamma Fc region receptor Mb (FCγRIIIb) (CD16b)) (SEQ ID NO: 37). In embodiments of the present invention where the antibodies and antigen binding fragments thereof, have an Fc domain, the Fc domain has been engineered to reduce or eliminate one or more Fc effector function. In a preferred embodiment the Fc domain has been engineered to reduce or eliminate platelet activation and/or platelet aggregation and the concomitant risk of thromboembolism.

As used herein, the singular forms "a", "an", and "the" include plural referents unless the context clearly dictates otherwise. The use of "or" or "and" means "and/or" unless stated otherwise. Furthermore, use of the term "including" as well as other forms, such as "include", "includes", and "included", is not limiting.

The use of the conjunction "or" is used interchangeably with at "least one of". For example: where a composition comprises A or B, the method must comprise at least one of A and B but may also comprise both A and B. Likewise a composition comprising "A, B, C or D" must comprise at least one of the group of A, B, C and D, but may also comprise all or any combination of A, B, C and D.

The term "about" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein encompasses variations of up to ±10% from the specified value. Unless otherwise indicated, all numbers expressing quantities of ingredients, properties such as molecular weight, reaction conditions, etc., used herein are to be understood as being modified by the term "about".

CD40L is also known as CD154, gp39, T-BAM, 5c8 antigen, or TNF related activation protein (TRAP).

The terms "treat," "treatment" and the like, include therapeutic treatment and prophylactic treatment. Therapeutic treatment is treatment of a subject that has signs or symptoms of the disease, condition or disorder to be treated. Prophylactic treatments refers to treatment of a subject that is predisposed to the disease, condition or disorder that does not show overt signs of the disease, condition or disorder. Thus, treatment may result in stasis of, partial or total alleviation, or reduction of signs or symptoms of illness, and specifically includes, without limitation, prolongation of survival and cure.

An "effective amount" of an agent, e.g., a pharmaceutical formulation, refers to an amount effective, at dosages and for periods of time necessary, to achieve the desired therapeutic or prophylactic result.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y may generally be represented by the equilibrium dissociation constant (KD), a ratio of koff/kon, between the antibody and its antigen. KD and affinity are inversely related. The KD value relates to the concentration of antibody (the amount of antibody needed for a particular experiment) and so the lower the KD value (lower concentration) and thus the higher the affinity of the antibody. Affinity may be measured by common methods known in the art, including those described herein. Specific, illustrative, and exemplary embodiments for measuring binding affinity may be measured by radioimmunoassays (RIA), Surface Plasmon Resonance (SPR) on a BIAcore® instrument (GE Healthcare Europe GmbH, Glattbrugg, Switzerland) by capturing the antibody on a protein-A coupled CM5 research grade sensor chip (GE Healthcare Europe GmbH, Glattbrugg, Switzerland; BR-1000-14) with a human CD40 ligand polypeptide used as analyte. Other methods may include radioimmunoassays, and the Kinetic Exclusion Assay. The Kinetic Exclusion Assay is a general purpose immunoassay platform that is capable of measuring equilibrium dissociation constants, and association and dissociation rate constants for antigen/anti-body interactions.

Reference in the specification is made to percent identity between polypeptide or amino acid sequences. The percent identity between the two sequences is a function of the number of identical positions shared by the sequences, taking into account the number of gaps, and the length of each gap, which need to be introduced for optimal alignment of the two sequences. Identity can be measured as "local identity" or "global identity". Local identity refers the degree of sequence relatedness between polypeptides as determined by the match between strings of such sequences. Global identity refers to the degree of sequence relatedness of a polypeptide compared to the full-length of a reference polypeptide. Unless specified otherwise, as used herein, identity means global identity. For the purposes of this disclosure and claims, the percentages for global identity are calculated using Needleman and Wunsch ((1970) J. Mol. Biol. 48:444-453) algorithm using a Blossum 62 scoring matrix with a gap penalty of 12, a gap extend penalty of 4, and a frameshift gap penalty of 5. There are many publically available software programs that incorporate the Needleman and Wunsch algorithm, e.g. the GAP program in the GCG software package.

One of ordinary skill in the art will appreciate that starting materials, biological and chemical materials, biological and chemical reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this disclosure.

Amino acid substitutions are denoted by the convention in which the original amino acid, the position of the amino acid in the specified sequence and the replacement amino acid are identified, for example, C11S would indicate that the cysteine at position 11 of the polypeptide sequence is replaced with a serine.

Humanized antibodies are antibodies produced from non-human species whose protein sequences have been modified to increase their similarity to antibody variants produced naturally in humans. The process of "humanization" is usually applied to monoclonal antibodies developed for administration to humans (for example, antibodies developed as anti-cancer drugs).

Currently it is common to humanize a non-human antibody by insertion of relevant CDRs from antibodies created in a non-human animal into a human antibody "scaffold". "Direct" creation of a humanized antibody can be accomplished by inserting the appropriate CDR coding segments (responsible for the desired binding properties) into a human antibody "scaffold". This may be achieved through recombinant DNA methods using an appropriate vector and expression in mammalian cells. That is, after an antibody is developed to have the desired properties in a mouse (or other non-human), the DNA coding for that antibody can be isolated, cloned into a vector and sequenced. The DNA sequence corresponding to the antibody CDRs can then be determined. Once the precise sequence of the desired CDRs are known, a strategy can be devised for inserting these sequences appropriately into a construct containing the DNA for a human antibody variant. The CDRs may also be varied, e.g., to increase specificity, prior to insertion into the scaffold.

The term "human" antibody refers to an antibody which possesses an amino acid sequence which corresponds to that of an antibody produced by a human and/or has been made using any technique for making human antibodies. This definition of a human antibody specifically excludes a humanized antibody comprising non-human antigen binding residues.

An "antigen binding antibody fragment" refers to a molecule other than an intact antibody that comprises a portion of an intact antibody that binds the antigen to which the intact antibody binds. Examples of antibody fragments include but are not limited to Fv, Fab, Fab', Fd fragments, dAb fragments, Fab'-SH, F(ab')2; diabodies; triabodies; linear antibodies; single-chain antibody molecules (e.g., scFv); and multispecific antibodies formed from antibody fragments, minimal recognition units consisting of the amino acid residues that mimic the hypervariable region of an antibody (e.g., an isolated complementarity determining region (CDR) such as a CDR3 peptide). An antigen binding fragment as disclosed in the present application binds to the antigen CD40L.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a VH domain associated with a VL domain, the VH and VL domains may be situated relative to one another in any suitable arrangement. For example, the variable region may be dimeric and contain VH-VH, VH-VL or VL-VL dimers. Alternatively, the antigen-binding fragment of an antibody may contain a monomeric VH or VL domain.

The isolated antibody includes bispecific antibodies in which each arm of the antibody or the antigen binding fragment binds to a different target or epitope.

The terms "full length antibody," "intact antibody," and "whole antibody" are used herein interchangeably to refer to an antibody having a structure substantially similar to a native antibody structure or having heavy chains that contain an Fc region.

"5c8" refers to the mouse anti-human antibody that binds CD40L and is produced by the hybridoma that is available from the ATCC having the accession number HB10916 and is described in U.S. Pat. No. 5,474,771. "hu5c8" refers to a humanized version of 5c8 the sequence of which is disclosed in Karpusas, et al., Structure vol. 9, pp 321-329, (2001).

The terms "subject" and "individual" and "patient" are used interchangeably herein, and refer to a human subject, individual or patient.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "may" and "may comprise" and their variants are intended to be non-limiting, such that recitation that an embodiment may or may comprise certain elements or features does not exclude other embodiments of the present technology that do not contain those elements or features The term "isolated protein" or "isolated polypeptide" (e.g., an isolated antibody or isolated antigen binding fragment) is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "variant" as used herein is defined as a modified or altered form of a wildtype sequence, e.g. where one or more amino acids may be replaced by other amino acid(s) or non-amino acid(s) which do not substantially affect function. In some embodiments, the variant may contain an altered side chain for at least one amino acid residue.

The term "antigen" as used herein is defined as an entity that can stimulate the production of antibodies and specifically combine with them and/or an entity which elicits an immune system response. For example, a cell surface protein or a specific linear or non-linear portion thereof. The term herein may be abbreviated to "Ag."

The term "specifically binds," or the like, means that an antibody or antigen-binding fragment thereof forms a complex with an antigen that is relatively stable under physiological conditions. Specific binding may be characterized by an equilibrium dissociation constant (KD) of about 3000 nM or less (i.e., a smaller KD denotes a tighter binding), about 2000 nM or less, about 1000 nM or less; about 500 nM or less; about 300 nM or less; about 200 nM or less; about 100 nM or less; about 50 nM or less; about 1 nM or less; or about 0.5 nM.

Specific binding for a particular antigen or an epitope may be exhibited, for example, by an antibody having a KD for an antigen or epitope of at least about $1\times10^{-4}$ M, at least about $1\times10^{-5}$ M, at least about $1\times10^{-6}$ M, at least about $1\times10^{-7}$ M, at least about $1\times10^{-8}$ M, at least about $1\times10^{-9}$ M, alternatively at least about $1\times10^{-10}$ M, at least about $1\times10^{-11}$ M, at least about $1\times10^{-12}$ M, or greater, where KD refers to a equilibrium dissociation constant of a particular antibody-antigen interaction. Typically, an antibody that specifically binds an antigen will have a KD that is 20-, 50-, 100-, 500-, 1000-, 5,000-, 10,000- or more times greater for a control molecule relative to the antigen or epitope. Also, specific binding for a particular antigen or an epitope may be exhibited, for example, by an antibody having a Ka for an antigen or epitope of at least 20-, 50-, 100-, 500-, 1000-, 5,000-, 10,000- or more times greater for the epitope relative to a control, where Ka refers to an association rate of a particular antibody-antigen interaction.

The term "neutralizing antibody" includes an antibody that is capable of inhibiting and/or neutralizing the biological activity of CD40L, for example an anti-CD40L antibody or antigen fragment thereof that inhibits or prevents or diminishes the binding of CD40L to CD40, and thus inhibiting or reducing the signaling pathway triggered by CD40L and/or inhibiting or reducing the binding of CD40L to CD40.

The terms "antagonistic antibody" or "antagonist antibody" are used herein equivalently and include an antibody that is capable of inhibiting and/or neutralizing the biological signaling activity of CD40L, as described for a neutralizing antibody supra.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although aspects of the present invention have been specifically disclosed by various embodiments which may include preferred embodiments, exemplary embodiments and optional features, modifications and variations of the concepts herein disclosed may be resorted to by those skilled in the art. Such modifications and variations are considered to be within the scope of embodiments of the invention as described and as may be defined by the appended claims.

Pharmaceutical Compositions and Methods of Administration

Pharmaceutical compositions for use in accordance with the methods of the present disclosure may be formulated in a conventional manner using one or more physiologically acceptable carriers. Pharmaceutically acceptable carriers are determined in part by the particular composition being administered, as well as by the particular method used to administer the composition. Accordingly, there are a wide variety of suitable formulations of the compounds useful in the methods of the present disclosure (see, e.g., Remington: The Science and Practice of Pharmacy, 20th ed., Gennaro et al. Eds., Lippincott Williams and Wilkins, 2000).

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Exemplary injection or infusion excipients may include mannitol, citric acid monohydrate, dibasic sodium phosphate dihydrate, monobasic sodium phosphate dihydrate, polysorbate 80, sodium chloride, sodium citrate and water.

According to the present disclosure the compounds can be administered by any suitable means, which can vary, depending on the type of disorder being treated and on the nature of the compound itself. For example, for the antibodies and antigen binding fragments thereof, of the present invention, administration routes preferably include parenteral, e.g., intramuscular, intravenous, intraarterial, intraperitoneal, intracerebrospinal, intraspinal, epidural, subcutaneous or by sustained release systems or an implant. Preferably, the parenteral dosing is given by injection, most preferably intravenous, intramuscular or subcutaneous injection.

In some embodiments, the anti-CD40L antibodies or antigen-binding fragments thereof of the present disclosure are formulated for and may be lyophilized for storage and reconstituted in a suitable excipient prior to use according to art-known lyophilization and reconstitution techniques.

In one exemplary pharmaceutical composition containing the anti-CD40L antibody or antigen-binding fragment thereof, the composition is formulated as a sterile, preservative-free solution of the anti-CD40L antibody or antigen-binding fragment thereof for intravenous or subcutaneous administration. The formulation may be supplied as either a single-use, prefilled pen, as a single-use, for example containing about 1 mL prefilled glass syringe, or as a single-use institutional use vial. Preferably, the pharmaceutical composition containing the anti-CD40L antibody or antigen-binding fragment thereof is clear and colorless, with a pH of about 5.0 to about 6.9, preferably a pH of about 5.0 to about 6.5, and even more preferably a pH ranging from about 5.0 to about 6.0. In various embodiments, the formulations comprising the pharmaceutical compositions may contain from about 500 mg to about 1 mg, or from about 400 mg to about 10 mg, or from about 300 mg to about 30 mg or from about 200 mg to about 50 mg of the anti-CD40L antibody or antigen-binding fragment thereof per mL of solution when reconstituted and administered to the subject.

Selecting an administration regimen for a therapeutic depends on several factors, including the serum or tissue turnover rate of the entity, the level of symptoms, the immunogenicity of the entity, and the accessibility of the target cells in the biological matrix, general health of the patient, the prior medical history of the patient, and the like. Preferably, an administration regimen maximizes the amount of therapeutic delivered to the patient consistent with an acceptable level of side effects. Accordingly, the amount of biologic delivered depends in part on the particular entity and the severity of the condition being treated. It should be appreciated that determination of proper dosage forms, dosage amounts, and routes of administration is within the level of ordinary skill in the pharmaceutical and medical arts.

Doses

The pharmaceutical formulations of the present disclosure may contain from about 0.001 to about 200 mg/kg of an anti-CD40L antibody or antigen binding fragment thereof, for example, from about 0.001 mg/kg to about 100 mg/kg, or from about 0.001 mg/kg to about 50 mg/kg, or from about 0.001 mg/kg to about 10 mg/kg intravenous injection of the anti-CD40L antibody, or antigen-binding fragment thereof, may be given as a bolus, and the rest of the antibody dose may be administered by intravenous injection. A predetermined dose of the anti-CD40L antibody, or antigen-binding fragment thereof, may be administered, for example, over a period of an hour to two hours to five hours.

In a further embodiment, part of the dose is administered by a subcutaneous injection and/or infusion in the form of a bolus and the rest by infusion of the antibody formulation. In some exemplary doses, the antibody formulation may be administered subcutaneously in a dose ranging from about 0.001 to about 200 mg/kg, for example, from about 0.001 mg/kg to about 100 mg/kg, or from about 0.001 mg/kg to about 50 mg/kg, or from about 0.001 mg/kg to about 10 mg/kg intravenous injection of the anti-CD40L antibody, or antigen-binding fragment thereof. In some embodiments the dose may be given as a bolus, and the rest of the antibody dose may be administered by subcutaneous or intravenous injection. A predetermined dose of the anti-CD40L antibody, or antigen-binding fragment thereof, may be administered, for example, over a period of an hour, or a period of two hours, or a period of three hours, or a period of four hours or a period of five hours or longer.

Combination Therapies

The antibodies or antibody fragments thereof described herein can be administered alone (monotherapy) or in combination, i.e., combined with other agents. For example, in one embodiment the combination therapy may include one or more additional therapeutic agents. In another embodiment the combination therapy includes standard of care treatment that may, or may not, include additional therapeutic agents (consists essentially of the antibody or antibody fragment thereof).

Adjunctive or combined administration (co-administration) includes simultaneous administration of any of the antibodies or antigen binding fragments thereof, described herein and one or more agents in the same or different dosage form, or separate administration of the polypeptide and one or more agents (e.g., sequential administration). Such concurrent or sequential administration preferably results in both the polypeptide and the one or more agents being simultaneously present in treated patients.

Kits and Articles of Manufacture

Further provided are kits containing the antibody or antigen binding fragments thereof described herein and instructions for use. Kits typically include a packaged combination of reagents in predetermined amounts with instructions and a label indicating the intended use of the contents of the kit. The term label or instruction includes any writing, or recorded material supplied on or with the kit, or which otherwise accompanies the kit at any time during its manufacture, transport, sale or use. It can be in the form prescribed by a governmental agency regulating the manufacture, use or sale of pharmaceuticals or biological products, which notice reflects approval by the agency of the manufacture, use or sale for administration to a human or for veterinary use. The label or instruction can also encompass advertising leaflets and brochures, packaging materials, and audio or video instructions.

EMBODIMENTS

All embodiments of the isolated antibodies or antigen binding fragments thereof, bind to CD40L and inhibit or block the binding of CD40L to CD40. As used herein, "block the binding of CD40L and CD40" and "block the interaction between CD40L and CD40" are used inter-changeably. Inhibiting or blocking the binding can be direct or indirect. Generally the antibody or antigen binding fragment thereof, will interfere physically with the binding of CD40L to CD40 via direct specific competition with CD40 for the same binding site on CD40L or via steric hindrance caused by binding of the antibody or antigen binding fragment thereof in proximity to the CD40-binding site of CD40L. In other instances the effect is indirect, for example the antibody or antigen binding fragment thereof cause an allosteric change in the conformation of CD40L which inhibits or eliminates its binding to CD40.

One embodiment is an isolated antibody that binds to CD40L and that comprises a light chain and a heavy chain, wherein the light chain comprises a light chain variable region comprises an amino acid sequence having at least 90%, or at least 91%, or at least 92%, or at least 93%, or at least 94%, or at least 95%, or at least 96% or at least 97%, or at least 98% or at least 99% sequence identity with SEQ ID NO: 5, SEQ ID NO: 6, SEQ ID NO: 7, or SEQ ID NO: 8, and the heavy chain comprises a variable heavy chain region wherein the heavy chain variable region comprises an amino acid sequence having at least 90%, or at least 91%, or at least 92%, or at least 93%, or at least 94%, or at least 95%, or at least 96%, or at least 97%, or at least 98%, or at least 99% sequence identity with SEQ ID NO:1, SEQ ID NO: 2, SEQ ID NO: 3, or SEQ ID NO: 4.

In one embodiment the present disclosure provides an isolated antibody or antigen-binding fragment thereof that specifically binds to CD40L comprising: a) a heavy chain variable region (VH) comprising; i) a CDRH1 domain comprising the sequence set forth in SEQ ID NO: 9; ii) a CDRH2 domain comprising the sequence set forth in SEQ ID NO: 10, 11, 12, 13, or 14; iii) a CDRH3 domain comprising the sequence set forth in SEQ ID NO: 15; and (b) a light chain variable region (VL) comprising: i) a CDRL1 domain comprising the sequence set forth in SEQ ID NO: 16 or 17; ii) a CDRL2 domain comprising the sequence set forth in SEQ ID NO: 18 or 19; iii) a CDRL3 domain comprising the sequence set forth in SEQ ID NO: 20.

In aspect A the present disclosure provides an isolated antibody or antigen-binding fragment thereof that specifically binds to CD40 L comprising: a) a heavy chain variable region (VH) comprising; i) a CDRH1 domain consisting of the sequence set forth in SEQ ID NO: 9; ii) a CDRH2 domain consisting of the sequence set forth in SEQ ID NO: 10, 11, 12, 13, or 14; iii) a CDRH3 domain consisting of the sequence set forth in SEQ ID NO: 15; and (b) a light chain variable region (VL) comprising: i) a CDRL1 domain consisting of the sequence set forth in SEQ ID NO: 16 or 17; ii) a CDRL2 domain consisting of the sequence set forth in SEQ ID NO: 18 or 19; iii) a CDRL3 domain consisting of the sequence set forth in SEQ ID NO: 20.

One embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 10; iii) a CDRH3 domain comprising the sequence set forth in SEQ ID NO: 15; and (b) a light chain variable region (VL) comprising: i) a CDRL1 domain comprising the sequence set forth in SEQ ID NO: 16; ii) a CDRL2 domain comprising the sequence set forth in SEQ ID NO: 18; iii) a CDRL3 domain comprising the sequence set forth in SEQ ID NO: 20. Another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 10; iii) a CDRH3 domain consisting of the sequence set forth in SEQ ID NO: 15; and (b) a light chain variable region (VL) comprising: i) a CDRL1 domain consisting of the sequence set forth in SEQ ID NO: 16; ii) a CDRL2 domain consisting of the sequence set forth in SEQ ID NO: 18; iii) a CDRL3 domain consisting of the sequence set forth in SEQ ID NO: 20.

Yet another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 10; iii) a CDRH3 domain comprising the sequence set forth in SEQ ID NO: 15; and (b) a light chain variable region (VL) comprising: i) a CDRL1 domain comprising the sequence set forth in SEQ ID NO: 17; ii) a CDRL2 domain comprising the sequence set forth in SEQ ID NO: 18; iii) a CDRL3 domain comprising the sequence set forth in SEQ ID NO: 20. Still another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 10; iii) a CDRH3 domain consisting of the sequence set forth in SEQ ID NO: 15; and (b) a light chain variable region (VL) comprising: i) a CDRL1 domain consisting of the sequence set forth in SEQ ID NO: 17; ii) a CDRL2 domain consisting of the sequence set forth in SEQ ID NO: 18; iii) a CDRL3 domain consisting of the sequence set forth in SEQ ID NO: 20.

Still another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 10; iii) a CDRH3 domain comprising the sequence set forth in SEQ ID NO: 15; and (b) a light chain variable region (VL) comprising: i) a CDRL1 domain comprising the sequence set forth in SEQ ID NO: 16; ii) a CDRL2 domain comprising the sequence set forth in SEQ ID NO: 19; iii) a CDRL3 domain comprising the sequence set forth in SEQ ID NO: 20. Yet another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 10; iii) a CDRH3 domain consisting of the sequence set forth in SEQ ID NO: 15; and (b) a light chain variable region (VL) comprising: i) a CDRL1 domain consisting of the sequence set forth in SEQ ID NO: 16; ii) a CDRL2 domain consisting of the sequence set forth in SEQ ID NO: 19; iii) a CDRL3 domain consisting of the sequence set forth in SEQ ID NO: 20.

Another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 10; iii) a CDRH3 domain comprising the sequence set forth in SEQ ID NO: 15; and (b) a light chain variable region (VL) comprising: i) a CDRL1 domain comprising the sequence set forth in SEQ ID NO: 17; ii) a CDRL2 domain comprising the sequence set forth in SEQ ID NO: 19; iii) a CDRL3 domain comprising the sequence set forth in SEQ ID NO: 20. Still another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 10; iii) a CDRH3 domain consisting of the sequence set forth in SEQ ID NO: 15; and (b) a light chain variable region (VL) comprising: i) a CDRL1 domain consisting of the sequence set forth in SEQ ID NO: 17; ii) a CDRL2 domain consisting of the sequence set forth in SEQ ID NO: 19; iii) a CDRL3 domain consisting of the sequence set forth in SEQ ID NO: 20

Yet another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 11; iii) a CDRH3 domain comprising the sequence set forth in SEQ ID NO: 15; and (b) a light chain variable region (VL) comprising: i) a CDRL1 domain comprising the sequence set forth in SEQ ID NO: 16; ii) a CDRL2 domain comprising the sequence set forth in SEQ ID NO: 18; iii) a CDRL3 domain comprising the sequence set forth in SEQ ID NO: 20. Still another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 11; iii) a CDRH3 domain consisting of the sequence set forth in SEQ ID NO: 15; and (b) a light chain variable region (VL) comprising: i) a CDRL1 domain consisting of the sequence set forth in SEQ ID NO: 16; ii) a CDRL2 domain consisting of the sequence set forth in SEQ ID NO: 18; iii) a CDRL3 domain consisting of the sequence set forth in SEQ ID NO: 20.

Yet another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 11; iii) a CDRH3 domain comprising the sequence set forth in SEQ ID NO: 15; and (b) a light chain variable region (VL) comprising: i) a CDRL1 domain comprising the sequence set forth in SEQ ID NO: 17; ii) a CDRL2 domain comprising the sequence set forth in SEQ ID NO: 18; iii) a CDRL3 domain comprising the sequence set forth in SEQ ID NO: 20. Yet another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 11; iii) a CDRH3 domain consisting of the sequence set forth in SEQ ID NO: 15; and (b) a light chain variable region (VL) comprising: i) a CDRL1 domain consisting of the sequence set forth in SEQ ID NO: 17; ii) a CDRL2 domain consisting of the sequence set forth in SEQ ID NO: 18; iii) a CDRL3 domain consisting of the sequence set forth in SEQ ID NO: 20.

Another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 11; iii) a CDRH3 domain comprising the sequence set forth in SEQ ID NO: 15; and (b) a light chain variable region (VL) comprising: i) a CDRL1 domain comprising the sequence set forth in SEQ ID NO: 16; ii) a CDRL2 domain comprising the sequence set forth in SEQ ID NO: 19; iii) a CDRL3 domain comprising the sequence set forth in SEQ ID NO: 20. Yet another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 11; iii) a CDRH3 domain consisting of the sequence set forth in SEQ ID NO: 15; and (b) a light chain variable region (VL) comprising: i) a CDRL1 domain consisting of the sequence set forth in SEQ ID NO: 16; ii) a CDRL2 domain consisting of the sequence set forth in SEQ ID NO: 19; iii) a CDRL3 domain consisting of the sequence set forth in SEQ ID NO: 20.

Yet another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 11; iii) a CDRH3 domain comprising the sequence set forth in SEQ ID NO: 15; and (b) a light chain variable region (VL) comprising: i) a CDRL1 domain comprising the sequence set forth in SEQ ID NO: 17; ii) a CDRL2 domain comprising the sequence set forth in SEQ ID NO: 19; iii) a CDRL3 domain comprising the sequence set forth in SEQ ID NO: 20. Another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 11; iii) a CDRH3 domain consisting of the sequence set forth in SEQ ID NO: 15; and (b) a light chain variable region (VL) comprising: i) a CDRL1 domain consisting of the sequence set forth in SEQ ID NO: 17; ii) a CDRL2 domain consisting of the sequence set forth in SEQ ID NO: 19; iii) a CDRL3 domain consisting of the sequence set forth in SEQ ID NO: 20.

Yet another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 12; iii) a CDRH3 domain comprising the sequence set forth in SEQ ID NO: 15; and (b) a light chain variable region (VL) comprising: i) a CDRL1 domain comprising the sequence set forth in SEQ ID NO: 16; ii) a CDRL2 domain comprising the sequence set forth in SEQ ID NO: 18; iii) a CDRL3 domain comprising the sequence set forth in SEQ ID NO: 20. Still another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 12; iii) a CDRH3 domain consisting of the sequence set forth in SEQ ID NO: 15; and (b) a light chain variable region (VL) comprising: i) a CDRL1 domain consisting of the sequence set forth in SEQ ID NO: 16; ii) a CDRL2 domain consisting of the sequence set forth in SEQ ID NO: 18; iii) a CDRL3 domain consisting of the sequence set forth in SEQ ID NO: 20.

Another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 12; iii) a CDRH3 domain comprising the sequence set forth in SEQ ID NO: 15; and (b) a light chain variable region (VL) comprising: i) a CDRL1 domain comprising the sequence set forth in SEQ ID NO: 17; ii) a CDRL2 domain comprising the sequence set forth in SEQ ID NO: 18; iii) a CDRL3 domain comprising the sequence set forth in SEQ ID NO: 20. Yet another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 12; iii) a CDRH3 domain consisting of the sequence set forth in SEQ ID NO: 15; and (b) a light chain variable region (VL) comprising: i) a CDRL1 domain consisting of the sequence set forth in SEQ ID NO: 17; ii) a CDRL2 domain consisting of the sequence set forth in SEQ ID NO: 18; iii) a CDRL3 domain consisting of the sequence set forth in SEQ ID NO: 20.

Yet another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 12; iii) a CDRH3 domain comprising the sequence set forth in SEQ ID NO: 15; and (b) a light chain variable region (VL) comprising: i) a CDRL1 domain comprising the sequence set forth in SEQ ID NO: 16; ii) a CDRL2 domain comprising the sequence set forth in SEQ ID NO: 19; iii) a CDRL3 domain comprising the sequence set forth in SEQ ID NO: 20. Another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 12; iii) a CDRH3 domain consisting of the sequence set forth in SEQ ID NO: 15; and (b) a light chain variable region (VL) comprising: i) a CDRL1 domain consisting of the sequence set forth in SEQ ID NO: 16; ii) a CDRL2 domain consisting of the sequence set forth in SEQ ID NO: 19; iii) a CDRL3 domain consisting of the sequence set forth in SEQ ID NO: 20.

Still another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 12; iii) a CDRH3 domain comprising the sequence set forth in SEQ ID NO: 15; and (b) a light chain variable region (VL) comprising: i) a CDRL1 domain comprising the sequence set forth in SEQ ID NO: 17; ii) a CDRL2 domain comprising the sequence set forth in SEQ ID NO: 19; iii) a CDRL3 domain comprising the sequence set forth in SEQ ID NO: 20. Yet another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 12; iii) a CDRH3 domain consisting of the sequence set forth in SEQ ID NO: 15; and (b) a light chain variable region (VL) comprising: i) a CDRL1 domain consisting of the sequence set forth in SEQ ID NO: 17; ii) a CDRL2 domain consisting of the sequence set forth in SEQ ID NO: 19; iii) a CDRL3 domain consisting of the sequence set forth in SEQ ID NO: 20.

Another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 13; iii) a CDRH3 domain comprising the sequence set forth in SEQ ID NO: 15; and (b) a light chain variable region (VL) comprising: i) a CDRL1 domain comprising the sequence set forth in SEQ ID NO: 16; ii) a CDRL2 domain comprising the sequence set forth in SEQ ID NO: 18; iii) a CDRL3 domain comprising the sequence set forth in SEQ ID NO: 20. Another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 13; iii) a CDRH3 domain consisting of the sequence set forth in SEQ ID NO: 15; and (b) a light chain variable region (VL) comprising: i) a CDRL1 domain consisting of the sequence set forth in SEQ ID NO: 16; ii) a CDRL2 domain consisting of the sequence set forth in SEQ ID NO: 18; iii) a CDRL3 domain consisting of the sequence set forth in SEQ ID NO: 20.

Another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 13; iii) a CDRH3 domain comprising the sequence set forth in SEQ ID NO: 15; and (b) a light chain variable region (VL) comprising: i) a CDRL1 domain comprising the sequence set forth in SEQ ID NO: 17; ii) a CDRL2 domain comprising the sequence set forth in SEQ ID NO: 18; iii) a CDRL3 domain comprising the sequence set forth in SEQ ID NO: 20. Still another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 13; iii) a CDRH3 domain consisting of the sequence set forth in SEQ ID NO: 15; and (b) a light chain variable region (VL) comprising: i) a CDRL1 domain consisting of the sequence set forth in SEQ ID NO: 17; ii) a CDRL2 domain consisting of the sequence set forth in SEQ ID NO: 18; iii) a CDRL3 domain consisting of the sequence set forth in SEQ ID NO: 20.

Still another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 13; iii) a CDRH3 domain comprising the sequence set forth in SEQ ID NO: 15; and (b) a light chain variable region (VL) comprising: i) a CDRL1 domain comprising the sequence set forth in SEQ ID NO: 17; ii) a CDRL2 domain comprising the sequence set forth in SEQ ID NO: 19; iii) a CDRL3 domain comprising the sequence set forth in SEQ ID NO: 20. Yet another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 13; iii) a CDRH3 domain consisting of the sequence set forth in SEQ ID NO: 15; and (b) a light chain variable region (VL) comprising: i) a CDRL1 domain consisting of the sequence set forth in SEQ ID NO: 17; ii) a CDRL2 domain consisting of the sequence set forth in SEQ ID NO: 19; iii) a CDRL3 domain consisting of the sequence set forth in SEQ ID NO: 20.

Yet another embodiment of aspect A is an isolated antibody or antigen-binding fragment thereof, comprising: (a) a heavy chain variable region (VH) comprising; i) a CDRH1 domain comprising the sequence set forth in SEQ ID NO: 9;

ii) a CDRH2 domain comprising the sequence set forth in SEQ ID NO: 14; iii) a CDRH3 domain comprising the sequence set forth in SEQ ID NO: 15; and (b) a light chain variable region (VL) comprising: i) a CDRL1 domain comprising the sequence set forth in SEQ ID NO: 16; ii) a CDRL2 domain comprising the sequence set forth in SEQ ID NO: 18; iii) a CDRL3 domain comprising the sequence set forth in SEQ ID NO: 20. Yet another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 14; iii) a CDRH3 domain consisting of the sequence set forth in SEQ ID NO: 15; and (b) a light chain variable region (VL) comprising: i) a CDRL1 domain consisting of the sequence set forth in SEQ ID NO: 16; ii) a CDRL2 domain consisting of the sequence set forth in SEQ ID NO: 18; iii) a CDRL3 domain consisting of the sequence set forth in SEQ ID NO: 20.

Another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 14; iii) a CDRH3 domain comprising the sequence set forth in SEQ ID NO: 15; and (b) a light chain variable region (VL) comprising: i) a CDRL1 domain comprising the sequence set forth in SEQ ID NO: 17; ii) a CDRL2 domain comprising the sequence set forth in SEQ ID NO: 18; iii) a CDRL3 domain comprising the sequence set forth in SEQ ID NO: 20. Another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 14; iii) a CDRH3 domain consisting of the sequence set forth in SEQ ID NO: 15; and (b) a light chain variable region (VL) comprising: i) a CDRL1 domain consisting of the sequence set forth in SEQ ID NO: 17; ii) a CDRL2 domain consisting of the sequence set forth in SEQ ID NO: 18; iii) a CDRL3 domain consisting of the sequence set forth in SEQ ID NO: 20.

Yet another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 14; iii) a CDRH3 domain comprising the sequence set forth in SEQ ID NO: 15; and (b) a light chain variable region (VL) comprising: i) a CDRL1 domain comprising the sequence set forth in SEQ ID NO: 17; ii) a CDRL2 domain comprising the sequence set forth in SEQ ID NO: 19; iii) a CDRL3 domain comprising the sequence set forth in SEQ ID NO: 20. Yet another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 14; iii) a CDRH3 domain consisting of the sequence set forth in SEQ ID NO: 15; and (b) a light chain variable region (VL) comprising: i) a CDRL1 domain consisting of the sequence set forth in SEQ ID NO: 17; ii) a CDRL2 domain consisting of the sequence set forth in SEQ ID NO: 19; iii) a CDRL3 domain consisting of the sequence set forth in SEQ ID NO: 20.

In aspect B the present disclosure provides isolated antibodies or an antigen-binding fragment thereof that specifically binds to CD40 L comprising: (a) a heavy chain variable region (VH) having the amino acid sequence as set forth in SEQ ID NOs: 1, 2, 3, or 4: and (b) a light chain variable region (VL) having the amino acid sequence as set forth in SEQ ID NOs: 5, 6, 7, or 8.

An embodiment of aspect B is an isolated antibody or antigen-binding fragment thereof comprising a heavy chain variable region (VH) having the amino acid sequence as set forth in SEQ ID NO: 1 and the light chain variable region (VL) having the amino acid sequence as set forth in SEQ ID NO: 5.

Another embodiment of aspect B is an isolated antibody or antigen-binding fragment thereof, comprising a heavy chain variable region (VH) having the amino acid sequence as set forth in SEQ ID NO: 1 and the light chain variable region (VL) having the amino acid sequence as set forth in SEQ ID NO: 6.

Yet another embodiment of aspect B is an isolated antibody or antigen-binding fragment thereof, comprising a heavy chain variable region (VH) having the amino acid sequence as set forth in SEQ ID NO: 1 and the light chain variable region (VL) having the amino acid sequence as set forth in SEQ ID NO: 7.

Another embodiment of aspect B is an isolated antibody or antigen-binding fragment thereof, comprising a heavy chain variable region (VH) having the amino acid sequence as set forth in SEQ ID NO: 1 and the light chain variable region (VL) having the amino acid sequence as set forth in SEQ ID NO: 8.

Yet another embodiment of aspect B is an isolated antibody or antigen-binding fragment thereof, comprising a heavy chain variable region (VH) having the amino acid sequence as set forth in SEQ ID NO: 1 and the light chain variable region (VL) having the amino acid sequence as set forth in SEQ ID NO: 5.

Still another embodiment of aspect B is an isolated antibody or antigen-binding fragment thereof, comprising a heavy chain variable region (VH) having the amino acid sequence as set forth in SEQ ID NO: 1 and the light chain variable region (VL) having the amino acid sequence as set forth in SEQ ID NO: 6.

Another embodiment of aspect B is an isolated antibody or antigen-binding fragment thereof, comprising a heavy chain variable region (VH) having the amino acid sequence as set forth in SEQ ID NO: 1 and the light chain variable region (VL) having the amino acid sequence as set forth in SEQ ID NO: 7.

Yet another embodiment of aspect B is an isolated antibody or antigen-binding fragment thereof, comprising a heavy chain variable region (VH) having the amino acid sequence as set forth in SEQ ID NO: 1 and the light chain variable region (VL) having the amino acid sequence as set forth in SEQ ID NO: 8.

Another embodiment of aspect B is an isolated antibody or antigen-binding fragment thereof, comprising a heavy chain variable region (VH) having the amino acid sequence as set forth in SEQ ID NO: 3 and the light chain variable region (VL) having the amino acid sequence as set forth in SEQ ID NO: 5.

Yet another embodiment of aspect B is an isolated antibody or antigen-binding fragment thereof, comprising a heavy chain variable region (VH) having the amino acid sequence as set forth in SEQ ID NO: 3 and the light chain variable region (VL) having the amino acid sequence as set forth in SEQ ID NO: 6.

Another embodiment of aspect B is an isolated antibody or antigen-binding fragment thereof, comprising a heavy chain variable region (VH) having the amino acid sequence as set forth in SEQ ID NO: 3 and the light chain variable region (VL) having the amino acid sequence as set forth in SEQ ID NO: 7.

Still another embodiment of aspect B is an isolated antibody or antigen-binding fragment thereof, comprising a heavy chain variable region (VH) having the amino acid sequence as set forth in SEQ ID NO: 3 and the light chain variable region (VL) having the amino acid sequence as set forth in SEQ ID NO: 8.

Yet another embodiment of aspect B is an isolated antibody or antigen-binding fragment thereof, comprising a heavy chain variable region (VH) having the amino acid sequence as set forth in SEQ ID NO: 4 and the light chain variable region (VL) having the amino acid sequence as set forth in SEQ ID NO: 5.

Still another embodiment of aspect B is an isolated antibody or antigen-binding fragment thereof, comprising a heavy chain variable region (VH) having the amino acid sequence as set forth in SEQ ID NO: 4 and the light chain variable region (VL) having the amino acid sequence as set forth in SEQ ID NO: 6.

Another embodiment of aspect B is an isolated antibody or antigen-binding fragment thereof, comprising a heavy chain variable region (VH) having the amino acid sequence as set forth in SEQ ID NO: 4 and the light chain variable region (VL) having the amino acid sequence as set forth in SEQ ID NO: 7.

Yet another embodiment of aspect B is an isolated antibody or antigen-binding fragment thereof, comprising a heavy chain variable region (VH) having the amino acid sequence as set forth in SEQ ID NO: 4 and the light chain variable region (VL) having the amino acid sequence as set forth in SEQ ID NO: 8.

Aspect C provides isolated antibodies of any of the embodiments described in the present application wherein the antibody comprises an Fc region and the Fc region has been engineered to reduce or eliminate one or more Fc effector function.

One embodiment of aspect C is where the Fc region is engineered such that the Fc region has reduced or eliminated binding to an Fc Receptor (FcR) or reduced or eliminated binding to C1q. In a particular embodiment of aspect C the FcR is FCγRIa (CD64), FCγRIIa (CD32), FCγRIIIa (CD16a), or FCγRIIIb (CD16b). In another embodiment of aspect C the FcR is FcγRIIa.

An embodiment of aspect C is an isolated antibody according to any one of the embodiments of the present invention, wherein the antibody is of the IgG1, IgG2, IgG3 or IgG4 isotype or any combination or hybrid version thereof. Another embodiment of aspect C is an isolated antibody according to any one of the embodiments of the present invention, wherein the antibody is of the IgG1 isotype, and wherein the heavy chain constant region comprises the amino acid sequence as set forth in SEQ ID NO: 21. (P238S and N297G) As shown in Experiment 3, none of the antibody clones provided in the present disclosure that were engineered with the Fc of SEQ ID NO: 21, bound to FCγRIa, FCγRIIa, FCγRIIIa, or FCγRIIIb. As shown in Experiment 4, none of the antibody clones provided in the present disclosure that were engineered with the Fc of SEQ ID NO: 21, bound to C1q.

A mutation of the IgG backbone Fc at position 297 (N297A) has been shown to abrogate IgG glycosylation and Fc gamma receptor binding. A mutation of the IgG backbone Fc at position 265 (D265A) has been shown to abrogate Fc gamma receptor binding. Accordingly embodiments of the present invention were prepared that comprised these mutations in the Fc region. One embodiment of aspect C is an isolated antibody according to any one the embodiments of the present disclosure which comprises a heavy chain constant region wherein the heavy chain constant region comprises the amino acid sequence as set forth in SEQ ID NO: 22. (D265A and N297A)

United States Patent Application publication number 2014/0294834 discloses a mutation of the heavy chain constant region. Thus, another embodiment is an isolated antibody according to any one of the embodiments having an Fc region that are disclosed in the present application, comprising a heavy chain constant region wherein the heavy chain constant region comprises the amino acid sequence as set forth in SEQ ID NO: 23. (T299K-MM131)

Another embodiment is an isolated antibody according to any one of the embodiments having an Fc region that are disclosed in the present application, comprising a heavy chain constant region wherein the heavy chain constant region comprises the amino acid sequence as set forth in SEQ ID NO: 24. (N299K)

In a particular embodiment the isolated antibody is the heavy chain variable region connected to the heavy chain constant region. In one embodiment the heavy chain variable region VH1 is connected directly to the heavy chain constant region having the P238S and N297G and the isolated antibody heavy chain consists of the amino acid sequence as provided in SEQ ID NO: 42. In another embodiment the heavy chain variable region VH2 is connected directly to the heavy chain constant region having the P238S and N297G and the isolated antibody heavy chain consists of the amino acid sequence as provided in SEQ ID NO: 43. In yet another embodiment the heavy chain variable region VH3 is connected directly to the heavy chain constant region having the P238S and N297G and the isolated antibody heavy chain consists of the amino acid sequence as provided in SEQ ID NO: 44. In still another embodiment the heavy chain variable region VH4 is connected directly to the heavy chain constant region having the P238S and N297G and the isolated antibody heavy chain consists of the amino acid sequence as provided in SEQ ID NO: 45.

In one embodiment the heavy chain variable region VH1 is connected directly to the heavy chain constant region having the D265A/N297A and the isolated antibody heavy chain consists of the amino acid sequence as provided in SEQ ID NO: 46. In yet another embodiment the heavy chain variable region VH2 is connected directly to the heavy chain constant region having the D265A/N297A and the isolated antibody heavy chain consists of the amino acid sequence as provided in SEQ ID NO: 47. In still another embodiment the heavy chain variable region VH3 is connected directly to the heavy chain constant region having the 265A/N297A and the isolated antibody heavy chain consists of the amino acid sequence as provided in SEQ ID NO: 48. In yet another embodiment the heavy chain variable region V4 is connected directly to the heavy chain constant region having the 265A/N297A and the isolated antibody heavy chain consists of the amino acid sequence as provided in SEQ ID NO: 49.

In still another embodiment the heavy chain variable region VH1 is connected directly to the heavy chain constant region having the IgG1/IgG4 hybrid and the isolated antibody heavy chain consists of the amino acid sequence as provided in SEQ ID NO: 50. In yet another embodiment the heavy chain variable region VH2 is connected directly to the heavy chain constant region having the IgG1/IgG4 hybrid and the isolated antibody heavy chain consists of the amino acid sequence as provided in SEQ ID NO: 51. In yet another embodiment the heavy chain variable region VH3 is connected directly to the heavy chain constant region having the IgG1/IgG4 hybrid and the isolated antibody heavy chain consists of the amino acid sequence as provided in SEQ ID NO: 51. In another embodiment the heavy chain variable region VH4 is connected directly to the heavy chain constant region having the IgG1/IgG4 hybrid and the isolated antibody heavy chain consists of the amino acid sequence as provided in SEQ ID NO: 53.

In another embodiment the heavy chain variable region VH1 is connected directly to the heavy chain constant region having the IgG4 and the isolated antibody heavy chain consists of the amino acid sequence as provided in SEQ ID NO: 54. In still another embodiment the heavy chain variable region VH2 is connected directly to the heavy chain constant region having the IgG4 and the isolated antibody heavy chain consists of the amino acid sequence as provided in SEQ ID NO: 55. In yet another embodiment the heavy chain variable region VH3 is connected directly to the heavy chain constant region having the IgG4 and the isolated antibody heavy chain consists of the amino acid sequence as provided in SEQ ID NO: 56. In another embodiment the heavy chain variable region VH4 is connected directly to the heavy chain constant region having the IgG4 and the isolated antibody heavy chain consists of the amino acid sequence as provided in SEQ ID NO: 57.

Yet another embodiment is an isolated antibody according to any one of the embodiments having a variable light chain and a light chain constant region wherein the light chain constant region comprises the sequence set forth in SEQ ID NO: 25. Another embodiment is a variable light chain 1 with the constant light chain region wherein the amino acid sequence is provided in SEQ ID NO: 38. Yet another embodiment is the variable light chain 2 with the constant light chain region wherein the amino acid sequence is provided in SEQ ID NO: 39. In still another embodiment the variable light chain 3 with the constant light chain region wherein the amino acid sequence is provided in SEQ ID NO: 40. In yet another embodiment the variable light chain 4 with the constant light chain region wherein the amino acid sequence is provided in SEQ ID NO: 41.

Another embodiment is a method for treating a subject with a CD40L-associated disease or disorder comprising administering to the subject a therapeutically effective amount of an antibody or antigen binding fragment thereof, disclosed in the present application.

Another embodiment is an isolated antibody having a heavy chain with the amino acid sequence as provided in SEQ ID NO: 42 and a light chain sequence as provided in SEQ ID NO: 38. Another embodiment is an isolated antibody having a heavy chain with the amino acid sequence as provided in SEQ ID NO: 43 and a light chain sequence as provided in SEQ ID NO: 38. Another embodiment is an isolated antibody having a heavy chain with the amino acid sequence as provided in SEQ ID NO: 44 and a light chain sequence as provided in SEQ ID NO: 38. Another embodiment is an isolated antibody having a heavy chain with the amino acid sequence as provided in SEQ ID NO: 45 and a light chain sequence as provided in SEQ ID NO: 38. Another embodiment is an isolated antibody having a heavy chain with the amino acid sequence as provided in SEQ ID NO: 42 and a light chain sequence as provided in SEQ ID NO:39. Another embodiment is an isolated antibody having a heavy chain with the amino acid sequence as provided in SEQ ID NO: 43 and a light chain sequence as provided in SEQ ID NO: 39. Another embodiment is an isolated antibody having a heavy chain with the amino acid sequence as provided in SEQ ID NO: 44 and a light chain sequence as provided in SEQ ID NO: 39. Another embodiment is an isolated antibody having a heavy chain with the amino acid sequence as provided in SEQ ID NO: 45 and a light chain sequence as provided in SEQ ID NO: 39. Another embodiment is an isolated antibody having a heavy chain with the amino acid sequence as provided in SEQ ID NO: 42 and a light chain sequence as provided in SEQ ID NO: 40. Another embodiment is an isolated antibody having a heavy chain with the amino acid sequence as provided in SEQ ID NO: 43 and a light chain sequence as provided in SEQ ID NO: 40. Another embodiment is an isolated antibody having a heavy chain with the amino acid sequence as provided in SEQ ID NO: 44 and a light chain sequence as provided in SEQ ID NO: 40. Another embodiment is an isolated antibody having a heavy chain with the amino acid sequence as provided in SEQ ID NO: 45 and a light chain sequence as provided in SEQ ID NO: 40. Another embodiment is an isolated antibody having a heavy chain with the amino acid sequence as provided in SEQ ID NO: 42 and a light chain sequence as provided in SEQ ID NO: 41. Another embodiment is an isolated antibody having a heavy chain with the amino acid sequence as provided in SEQ ID NO: 43 and a light chain sequence as provided in SEQ ID NO: 41. Another embodiment is an isolated antibody having a heavy chain with the amino acid sequence as provided in SEQ ID NO: 44 and a light chain sequence as provided in SEQ ID NO: 41. Another embodiment is an isolated antibody having a heavy chain with the amino acid sequence as provided in SEQ ID NO: 45 and a light chain sequence as provided in SEQ ID NO: 41.

Another embodiment is an isolated antibody having a heavy chain with the amino acid sequence as provided in SEQ ID NO: 46 and a light chain with the amino acid sequence as provided in SEQ ID NO: 38. Another embodiment is an isolated antibody having a heavy chain with the amino acid sequence as provided in SEQ ID NO: 47 and a light chain amino acid sequence as provided in SEQ ID NO: 38. Another embodiment is an isolated antibody having a heavy chain with the amino acid sequence as provided in SEQ ID NO: 48 and a light chain amino acid sequence as provided in SEQ ID NO: 38. Another embodiment is an isolated antibody having a heavy chain with the amino acid sequence as provided in SEQ ID NO: 49 and a light chain amino acid sequence as provided in SEQ ID NO: 38. Another embodiment is an isolated antibody having a heavy chain with the amino acid sequence as provided in SEQ ID NO: 46 and a light chain amino acid sequence as provided in SEQ ID NO:39. Another embodiment is an isolated antibody having a heavy chain with the amino acid sequence as provided in SEQ ID NO: 47 and a light chain amino acid sequence as provided in SEQ ID NO: 39. Another embodiment is an isolated antibody having a heavy chain with the amino acid sequence as provided in SEQ ID NO: 48 and a light chain amino acid sequence as provided in SEQ ID NO: 39. Another embodiment is an isolated antibody having a heavy chain with the amino acid sequence as provided in SEQ ID NO: 49 and a light chain amino acid sequence as provided in SEQ ID NO: 39. Another embodiment is an isolated antibody having a heavy chain with the amino acid sequence as provided in SEQ ID NO: 46 and a light chain amino acid sequence as provided in SEQ ID NO: 40. Another embodiment is an isolated antibody having a heavy chain with the amino acid sequence as provided in SEQ ID NO: 47 and a light chain amino acid sequence as provided in SEQ ID NO: 40. Another embodiment is an isolated antibody having a heavy chain with the amino acid sequence as provided in SEQ ID NO: 48 and a light chain amino acid sequence as provided in SEQ ID NO: 40. Another embodiment is an isolated antibody having a heavy chain with the amino acid sequence as provided in SEQ ID NO: 49 and a light chain amino acid sequence as provided in SEQ ID NO: 40. Another embodiment is an isolated antibody having a heavy chain with the amino acid sequence as provided in SEQ ID NO: 46 and a light chain amino acid sequence as provided in SEQ ID NO: 41. Another embodiment is an isolated antibody having a heavy chain with the amino acid sequence as provided in SEQ ID NO: 47 and a light chain amino acid sequence as provided in SEQ ID NO: 41. Another embodiment is an isolated antibody having a heavy chain with the amino acid sequence as provided in SEQ ID NO: 48 and a light chain amino acid sequence as provided in SEQ ID NO: 41. Another embodiment is an isolated antibody having a heavy chain with the amino acid sequence as provided in SEQ ID NO: 49 and a light chain amino acid sequence as provided in SEQ ID NO: 41.

Another embodiment is an isolated antibody having a heavy chain with the amino acid sequence as provided in SEQ ID NO: 50 and a light chain amino acid sequence as provided in SEQ ID NO: 38. Another embodiment is an isolated antibody having a heavy chain with the amino acid sequence as provided in SEQ ID NO: 51 and a light chain amino acid sequence as provided in SEQ ID NO: 38. Another embodiment is an isolated antibody having a heavy chain with the amino acid sequence as provided in SEQ ID NO: 52 and a light chain amino acid sequence as provided in SEQ ID NO: 38. Another embodiment is an isolated antibody having a heavy chain with the amino acid sequence as provided in SEQ ID NO: 53 and a light chain amino acid sequence as provided in SEQ ID NO: 38. Another embodiment is an isolated antibody having a heavy chain with the amino acid sequence as provided in SEQ ID NO: 50 and a light chain amino acid sequence as provided in SEQ ID NO:39. Another embodiment is an isolated antibody having a heavy chain with the amino acid sequence as provided in SEQ ID NO: 51 and a light chain amino acid sequence as provided in SEQ ID NO: 39. Another embodiment is an isolated antibody having a heavy chain with the amino acid sequence as provided in SEQ ID NO: 52 and a light chain amino acid sequence as provided in SEQ ID NO: 39. Another embodiment is an isolated antibody having a heavy chain with the amino acid sequence as provided in SEQ ID NO: 53 and a light chain amino acid sequence as provided in SEQ ID NO: 39. Another embodiment is an isolated antibody having a heavy chain with the amino acid sequence as provided in SEQ ID NO: 50 and a light chain amino acid sequence as provided in SEQ ID NO: 40. Another embodiment is an isolated antibody having a heavy chain with the amino acid sequence as provided in SEQ ID NO: 51 and a light chain amino acid sequence as provided in SEQ ID NO: 40. Another embodiment is an isolated antibody having a heavy chain with the amino acid sequence as provided in SEQ ID NO: 52 and a light chain amino acid sequence as provided in SEQ ID NO: 40. Another embodiment is an isolated antibody having a heavy chain with the amino acid sequence as provided in SEQ ID NO: 53 and a light chain amino acid sequence as provided in SEQ ID NO: 40. Another embodiment is an isolated antibody having a heavy chain with the amino acid sequence as provided in SEQ ID NO: 50 and a light chain amino acid sequence as provided in SEQ ID NO: 41. Another embodiment is an isolated antibody having a heavy chain with the amino acid sequence as provided in SEQ ID NO: 51 and a light chain amino acid sequence as provided in SEQ ID NO: 41. Another embodiment is an isolated antibody having a heavy chain with the amino acid sequence as provided in SEQ ID NO: 52 and a light chain amino acid sequence as provided in SEQ ID NO: 41. Another embodiment is an isolated antibody having a heavy chain with the amino acid sequence as provided in SEQ ID NO: 53 and a light chain amino acid sequence as provided in SEQ ID NO: 41.

Another embodiment is an isolated antibody having a heavy chain with the amino acid sequence as provided in SEQ ID NO: 54 and a light chain amino acid sequence as provided in SEQ ID NO: 38. Another embodiment is an isolated antibody having a heavy chain with the amino acid sequence as provided in SEQ ID NO: 55 and a light chain amino acid sequence as provided in SEQ ID NO: 38. Another embodiment is an isolated antibody having a heavy chain with the amino acid sequence as provided in SEQ ID NO: 56 and a light chain amino acid sequence as provided in SEQ ID NO: 38. Another embodiment is an isolated antibody having a heavy chain with the amino acid sequence as provided in SEQ ID NO: 57 and a light chain amino acid sequence as provided in SEQ ID NO: 38. Another embodiment is an isolated antibody having a heavy chain with the amino acid sequence as provided in SEQ ID NO: 54 and a light chain amino acid sequence as provided in SEQ ID NO:39. Another embodiment is an isolated antibody having a heavy chain with the amino acid sequence as provided in SEQ ID NO: 55 and a light chain amino acid sequence as provided in SEQ ID NO: 39. Another embodiment is an isolated antibody having a heavy chain with the amino acid sequence as provided in SEQ ID NO: 56 and a light chain amino acid sequence as provided in SEQ ID NO: 39. Another embodiment is an isolated antibody having a heavy chain with the amino acid sequence as provided in SEQ ID NO: 57 and a light chain amino acid sequence as provided in SEQ ID NO: 39. Another embodiment is an isolated antibody having a heavy chain with the amino acid sequence as provided in SEQ ID NO: 54 and a light chain amino acid sequence as provided in SEQ ID NO: 40. Another embodiment is an isolated antibody having a heavy chain with the amino acid sequence as provided in SEQ ID NO: 55 and a light chain amino acid sequence as provided in SEQ ID NO: 40. Another embodiment is an isolated antibody having a heavy chain with the amino acid sequence as provided in SEQ ID NO: 56 and a light chain amino acid sequence as provided in SEQ ID NO: 40. Another embodiment is an isolated antibody having a heavy chain with the amino acid sequence as provided in SEQ ID NO: 57 and a light chain amino acid sequence as provided in SEQ ID NO: 40. Another embodiment is an isolated antibody having a heavy chain with the amino acid sequence as provided in SEQ ID NO: 54 and a light chain amino acid sequence as provided in SEQ ID NO: 41. Another embodiment is an isolated antibody having a heavy chain with the amino acid sequence as provided in SEQ ID NO: 55 and a light chain amino acid sequence as provided in SEQ ID NO: 41. Another embodiment is an isolated antibody having a heavy chain with the amino acid sequence as provided in SEQ ID NO: 56 and a light chain amino acid sequence as provided in SEQ ID NO: 41. Another embodiment is an isolated antibody having a heavy chain with the amino acid sequence as provided in SEQ ID NO: 57 and a light chain amino acid sequence as provided in SEQ ID NO: 41.

Yet another embodiment is a method for treating a subject with a neurodegenerative or a neuromuscular disease or disorder; an inflammatory or immune disease or disorder; or an autoimmune disease, comprising administering to the subject a therapeutically effective amount of an antibody or antigen binding fragment thereof, disclosed in the present application.

Another embodiment is a method for treating a subject with a an autoimmune disease, selected from the group consisting of systemic lupus erythematous, type-1 diabetes, Myasthenia gravis, psoriasis, Addison's disease, Crohn's disease, uveitis, multiple sclerosis, hemolytic anemia, inflammatory bowel disease, immune thrombocytopenic purpura, Graves' disease, and rheumatoid arthritis, comprising administering to the subject a therapeutically effective amount of an antibody or antigen binding fragment thereof, disclosed in the present application.

Still another embodiment is a method for treating a subject having a neurodegenerative disorder or a neuromuscular disorder selected from the group consisting of Alzheimer's Disease, Parkinson's Disease, Amyotrophic Lateral Sclerosis, Multifocal Motor Neuropathy, Primary Lateral Sclerosis, Spinal Muscular Atrophy, Kennedy's Disease, and Spinocerebellar Ataxia comprising administering to the subject a therapeutically effective amount of an antibody or antigen binding fragment thereof disclosed in the present application.

Yet another embodiment is a method for treating a subject having Amyotrophic Lateral Sclerosis comprising administering to the subject a therapeutically effective amount of an antibody or antigen binding fragment thereof, disclosed in the present application.

Another embodiment is a method for inhibiting an immune response in a subject comprising administering to the subject a therapeutically effective amount of an antibody or antigen binding fragment thereof, disclosed in the present application.

Another embodiment is a method of inhibiting an immune response in a subject comprising administering to the subject a therapeutically effective amount of an antibody or antigen binding fragment thereof, wherein the immune response is graft vs. host disease, or organ transplant rejection.

Yet another embodiment is a method according to any of the methods of the present disclosure, wherein the antibody or antibody fragment is administered in combination with another therapeutic agent. One embodiment is a method according to any of the methods of the present disclosure, wherein the antibody or antibody fragment is administered in combination with a compound that blocks the interaction between CD28 and CD86 or between CD28 and CD80.

Still another embodiment is a method according to any of the methods of the present disclosure, wherein the antibody or antibody fragment is administered in combination with compound that blocks the interaction between CD28 and CD86 or between CD28 and CD80 is a CTLA4-Ig fusion protein.

Yet another embodiment is a method according to any of the methods of the present disclosure, wherein the antibody or antibody fragment is administered in combination with compound that blocks the interaction between CD28 and CD86 or between CD28 and CD80 is abatacept or belatacept or galiximab.

TABLE 1

Sequences

| Description | Sequence | SEQ ID NO: |
|---|---|---|
| Heavy chain 1 (VH1) | EVQLVQSGAEVKKPGASVKVSCKASGYTFTSYYMYWVRQ APGQGLEWMGEINPSNGDTNYAQKFQGRVTMTVDTSTST VYMELSSLRSEDTAVYYCARSDGRNDMDSWGQGTLVTVS S | 1 |
| Heavy chain 2 (VH2) | EVQLVQSGAEVKKPGASVKVSCKASGYIFTSYYMYWVRQ APGQGLEWMGEINPSNGDTNYAEKFKGRVTMTVDTSTST VYMELSSLRSEDTAVYYCTRSDGRNDMDSWGQGTLVTVS S | 2 |
| Heavy chain 3 (VH3) | EVQLVQSGAEVKKPGASVKVSCKASGYIFTSYMMYWVRQ APGQGLEWIGEINPSNGDTNYAEKFKGRATLTVDTSTST VYMELSSLRSEDTAVYYCTRSDGRNDMDSWGQGTLVTVS S | 3 |
| Heavy chain 4 (VH4) | QVQLVQSGAEVKKPGASVKVSCKASGYIFTSYYMYWVRQ APGQGLEWIGEINPSNGDTNFAEKFKGRATLTVDTSTST VYMELSSLRSEDTAVYYCTRSDGRNDMDSWGQGTLVTVS S | 4 |
| Light chain 1 (VL1) | EIVLTQSPATLSLSPGERATLSCRASQRVSSSTYSYMHW YQQKPGQAPRLLIYDASNRATGIPARFSGSGSGTDFTLT ISSLEPEDFAVYYCQHSWEIPPTFGQGTKLEIK | 5 |
| Light chain 2 (VL2) | EIVLTQSPATLSLSPGERATLSCRADERVSSSTYSYMHW YQQKPGQAPRLLIYDASNRATGIPARFSGSGSGTDFTLT ISSLEPEDFAVYYCQHSWEIPPTFGQGTKLEIK | 6 |
| Light chain 3 (VL3) | EIVLTQSPATLSLSPGERATLSCRASQRVSSSTYSYMHW YQQKPGQAPRLLIKYASNRETGIPARFSGSGSGTDFTLT ISSLEPEDFAVYYCQHSWEIPPTFGQGTKLEIK | 7 |
| Light chain 4 (VL4) | EIVLTQSPATLSLSPGERATLSCRADERVSSSTYSYMHW YQQKPGQAPRLLIKYASNRETGIPARFSGSGSGTDFTLT ISSLEPEDFAVYYCQHSWEIPPTFGQGTKLEIK | 8 |

TABLE 1 -continued

Sequences

| Description | Sequence | SEQ ID NO: |
|---|---|---|
| Heavy chain CDR1 | SYYMY | 9 |
| Heavy chain H1 CDR2 | EINPSNGDTNYAQKFQG | 10 |
| Heavy chain H2 CDR2A (CDR2 and flanking region RV) | EINPSNGDTNYAEKFKGRV | 11 |
| Heavy chain H3 CDR2B (CDR2 and flanking region RA) | EINPSNGDTNYAEKFKGRA | 12 |
| Heavy chain H4 CDR2 | EINPSNGDTNFAEKFKG | 13 |
| Heavy chain H2 and H3 CDR2 | EINPSNGDTNYAEKFKG | 14 |
| Heavy Chain CDR3 | SDGRNDMDS | 15 |
| Light Chain CDR1 L1 and L4 | RASQRVSSSTYSYMH | 16 |
| Light Chain CDR1 L2 and L4 | RADERVSSSTYSYMH | 17 |
| Light Chain CDR2 L1 and L2 | DASNRAT | 18 |
| Light Chain CDR2 L3 and L4 | YASNRET | 19 |
| Light Chain CDR3 | QHSWEIPPT | 20 |
| Engineered effectorless IgG1Fc with P238S and N297G mutations (underlined) | EPKSCDKTHTCPPCPAPELLGGSSVFLFPPKPKDTLMISRTP EVTCVVVDVSHEDPEVKFNWYVDGVEVHNAKTKPREEQYGST YRVVSVLTVLHQDWLNGKEYKCKVSNKALPAPIEKTISKAKG QPREPQVYTLPPSRDELTKNQVSLTCLVKGFYPSDIAVEWES NGQPENNYKTTPPVLDSDGSFFLYSKLTVDKSRWQQGNVFSC SVMHEALHNHYTQKSLSLSPGK | 21 |
| Engineered D265A/N297A effectorless IgG1 constant heavy chain | ASTKGPSVFPLAPSSKSTSGGTAALGCLVKDYFPEPVTVSWN SGALTSGVHTFPAVLQSSGLYSLSSVVTVPSSSLGTQTYICN VNHKPSNTKVDKKVEPKSCDKTHTCPPCPAPELLGGPSVFLF PPKPKDTLMISRTPEVTCVVVAVSHEDPEVKFNWYVDGVEVH NAKTKPREEQYASTYRVVSVLTVLHQDWLNGKEYKCKVSNKA LPAPIEKTISKAKGQPREPQVYTLPPSRDELTKNQVSLTCLV KGFYPSDIAVEWESNGQPENNYKTTPPVLDSDGSFFLYSKLT VDKSRWQQGNVFSCSVMHEALHNHYTQKSLSLSPG | 22 |
| Engineered effectorless IgG1/IgG4 hybrid constant heavy chain sequence | ASTKGPSVFPLAPSSKSTSGGTAALGCLVKDYFPEPVTVSWN SGALTSGVHTFPAVLQSSGLYSLSSVVTVPSSSLGTQTYICN VNHKPSNTKVDKKVEPKSCDKTHTCPSCPAPEFLGGPSVFLF PPKPKDTLMISRTPEVTCVVVDVSQEDPEVQFNWYVDGVEVH NAKTKPREEQFNSKYRVVSVLTVLHQDWLNGKEYKCKVSNKG LPSSIEKTISKAKGQPREPQVYTLPPSREEMTKNQVSLSCAV KGFYPSDIAVEWESNGQPENNYKTTPPVLDSDGSFFLVSKLT VDKSRWQQGNVFSCSVMHEALHNHYTQKSLSLSPG | 23 |
| Engineered effectorless IgG4 constant heavy chain sequence | ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFLGGPSVFLFPPK PKDTLMISRTPEVICVVVDVSQEDPEVQFNWYVDGVEVHNAK TKPREEQFNSKYRVVSVLTVLHQDWLNGKEYKCKVSNKGLPS SIEKTISKAKGQPREPQVYTLPPSQEEMTKNQVSLTCLVKGF YPSDIAVEWESNGQPENNYKTTPPVLDSDGSFFLYSRLTVDK SRWQEGNVFSCSVMHEALHNHYTQKSLSLSLG | 24 |
| Constant light chain sequence | RTVAAPSVFIFPPSDEQLKSGTASVVCLLNNFYPREAKVQWK VDNALQSGNSQESVTEQDSKDSTYSLSSTLTLSKADYEKHKV YACEVTHQGLSSPVTKSFNRGEC | 25 |

TABLE 1 -continued

| Description | Sequence | SEQ ID NO: |
|---|---|---|
| Heavy chain 1 (VH1) DNA | GAGGTGCAGCTGGTGCAGTCCGGCGCCGAGGTGAAGAAGCCC GGCGCCTCCGTGAAGGTGTCCTGCAAGGCCTCCGGCTACACC TTCACCTCCTACTACATGTACTGGGTGAGGCAGGCCCCCGGC CAGGGCCTGGAGTGGATGGGCGAGATCAACCCCTCCAACGGC GACACCAACTACGCACAGAAGTTCCAGGGTAGGGTCACCATG ACCGTGGACACGTCCACCTCCACCGTCTACATGGAGCTGTCC TCCCTGAGGTCCGAGGACACCGCCGTGTACTACTGCGCCAGG TCCGACGGCAGGAACGACATGGACTCCTGGGGCCAGGGCACC CTGGTGACCGTGTCCTCC | 26 |
| Heavy chain 2 (VH2) DNA | GAGGTGCAGCTGGTGCAGTCCGGCGccGAGGTGAAGAAGCCC GGCGCCTCCGTGAAGGTGTCCTGCAAGGCCTCCGGCTACACC TTCACCTCCTACTACATGTACTGGGTGAGGCAGGCCCCCGGC CAGGGCCTGGAGTGGATGGGCGAGATCAACCCCTCCAACGGC GACACCAACTACGCAGAGAAGTTCAAGGGTAGGGTCACCATG ACCGTGGACACGTCCACCTCCACCGTCTACATGGAGCTGTCC TCCCTGAGGTCCGAGGACACCGCCGTGTACTACTGCACCAGG TCCGACGGCAGGAACGACATGGACTCCTGGGGCCAGGGCACC CTGGTGACCGTGTCCTCC | 27 |
| Heavy chain 3 (VH3) DNA | GAGGTGCAGCTGGTGCAGTCCGGCGCCGAGGTGAAGAAGCCC GGCGCCTCCGTGAAGGTGTCCTGCAAGGCCTCCGGCTACATC TTCACCTCCTACTACATGTACTGGGTGAGGCAGGCCCCCGGC CAGGGCCTGGAGTGGATCGGCGAGATCAACCCCTCCAACGGC GACACCAACTACGCAGAGAAGTTCAAGGGTAGGGCCACCCTG ACCGTGGACACGTCCACCTCCACCGTCTACATGGAGCTGTCC TCCCTGAGGTCCGAGGACACCGCCGTGTACTACTGCACCAGG TCCGACGGCAGGAACGACATGGACTCCTGGGGCCAGGGCACC CTGGTGACCGTGTCCTCC | 28 |
| Heavy chain 4 (VH4) DNA | CAGGTGCAGCTGGTGCAGTCCGGCGCCGAGGTGAAGAAGCCC GGCGCCTCCGTGAAGGTGTCCTGCAAGGCCTCCGGCTACATC TTCACCTCCTACTACATGTACTGGGTGAGGCAGGCCCCCGGC CAGGGCCTGGAGTGGATCGGCGAGATCAACCCCTCCAACGGC GACACCAACTTCGCAGAGAAGTTCAAGGGTAGGGCCACCCTG ACCGTGGACACGTCCACCTCCACCGTCTACATGGAGCTGTCC TCCCTGAGGTCCGAGGACACCGCCGTGTACTACTGCACCAGG TCCGACGGCAGGAACGACATGGACTCCTGGGGCCAGGGCACC CTGGTGACCGTGTCCTCC | 29 |
| Light chain 1 (VL1) DNA | GAGATCGTGCTGACCCAGTCACCTGCCACCCTGTCCCTGTCA CCTGGAGAGAGAGCCACCCTCTCCTGCAGAGCCTCCCAGAGG GTGTCCTCCTCCACCTACTCCTACATGCACTGGTACCAGCAG AAGCCTGGACAGGCACCTAGGCTGCTGATCTACGACGCCTCC AACAGGGCGACCGGTATACCAGCCAGGTTCTCAGGCTCAGGC TCAGGCACCGACTTCACCCTGACCATCTCCTCCCTGGAGCCA GAGGACTTCGCCGTCTACTACTGCCAGCACTCCTGGGAGATC CCACCTACCTTCGGACAAGGCACCAAGCTGGAAATCAAA | 30 |
| Light chain 2 (VL2) DNA | GAGATCGTGCTGACCCAGTCACCTGCCACCCTGTCCCTGTCA CCTGGAGAGAGAGCCACCCTCTCCTGCAGAGCCGATGAGAGG GTGTCCTCCTCCACCTACTCCTACATGCACTGGTACCAGCAG AAGCCTGGACAGGCACCTAGGCTGCTGATCTACGACGCCTCC AACAGGGCGACCGGTATACCAGCCAGGTTCTCAGGCTCAGGC TCAGGCACCGACTTCACCCTGACCATCTCCTCCCTGGAGCCA GAGGACTTCGCCGTCTACTACTGCCAGCACTCCTGGGAGATC CCACCTACCTTCGGACAAGGCACCAAGCTGGAAATCAAA | 31 |
| Light chain 3 (VL3) DNA | GAGATCGTGCTGACCCAGTCACCTGCCACCCTGTCCCTGTCA CCTGGAGAGAGAGCCACCCTCTCCTGCAGAGCCTCCCAGAGG GTGTCCTCCTCCACCTACTCCTACATGCACTGGTACCAGCAG AAGCCTGGACAGGCACCTAGGCTGCTGATCAAGTACGCCTCC AACAGGGAGACCGGTATACCAGCCAGGTTCTCAGGCTCAGGC TCAGGCACCGACTTCACCCTGACCATCTCCTCCCTGGAGCCA GAGGACTTCGCCGTCTACTACTGCCAGCACTCCTGGGAGATC CCACCTACCTTCGGACAAGGCACCAAGCTGGAAATCAAA | 32 |
| Light chain 4 (VL4) DNA | GAGATCGTGCTGACCCAGTCACCTGCCACCCTGTCCCTGTCA CCTGGAGAGAGAGCCACCCTCTCCTGCAGAGCCGATGAGAGG GTGTCCTCCTCCACCTACTCCTACATGCACTGGTACCAGCAG AAGCCTGGACAGGCACCTAGGCTGCTGATCAAGTACGCCTCC AACAGGGAGACCGGTATACCAGCCAGGTTCTCAGGCTCAGGC TCAGGCACCGACTTCACCCTGACCATCTCCTCCCTGGAGCCA GAGGACTTCGCCGTCTACTACTGCCAGCACTCCTGGGAGATC CCACCTACCTTCGGACAAGGCACCAAGCTGGAAATCAAA | 33 |

TABLE 1 -continued

| | Sequences | |
|---|---|---|
| Description | Sequence | SEQ ID NO: |
| Fc fragment of IgG, high affinity Ia, receptor (CD64) (FCγRIa) | MWFLTTLLLLWVPVDGQVDTTKAVITLQPPWVSVFQEETVTLH CEVLHLPGSSSTQWFLNGTATQTSTPSYRITSASVNDSGEYR CQRGLSGRSDPIQLEIHRGWLLLQVSSRVFTEGEPLALRCHA WKDKLVYNVLYYRNGKAFKFFHWNSNLTILKTNISHNGTYHC SGMGKHRYTSAGISVTVKELFPAPVLNASVTSPLLEGNLVTL SCETKLLLQRPGLQLYFSFYMGSKTLRGRNTSSEYQILTARR EDSGLYWCEAATEDGNVLKRSPELELQVLGLQLPTPVWFHVL FYLAVGIMFLVNTVLWVTIRKELKRKKKWDLEISLDSGHEKK VISSLQEDRHLEEELKCQEQKEEQLQEGVHRKEPQGAT | 34 |
| Low affinity immunoglobulin gamma Fc region acceptor IIa (FCγRIIa) (CD32) | MTMETQMSQNVCPRNLWLLQPLTVLLLLASADSQAAPPKAVL KLEPPWINVLQEDSVTLICQGARSPESDSIQWFHNGNLIPTH TQPSYRFKANNNDSGEYTCQTGQTSLSDPVHLTVLSEWLVLQ TPHLEFQEGETIMLRCHSWKDKPLVKVTFFQNGKSQKFSHLD PTFSIPQANHSHSGDYHCTGNIGYTLFSSKPVTITVQVPSMG 555PMGVIVAVVIATAVAAIVAAVVALIYCRKKRISANSTDP VKAAQFEPPGRQMIAIRKRQLEETNNDYETADGGYMTLNPRA PTDDDKNIYLTLPPNDHVNSNN | 35 |
| low affinity immunoglobulin gamma Fc region receptor IIIa (FCγRIIIA) (CD16a) | MGGGAGERLFTSSCLVGLVPLGLRISLVTCPLQCGIMWQLLL PTALLLLVSAGMRTEDLPKAVVFLEPQWYRVLEKDSVTLKCQ GAYSPEDNSTQWFHNESLISSQASSYFIDAATVDDSGEYRCQ TNLSTLSDPVQLEVHIGWLLLQAPRWVFKEEDPIHLRCHSWK NTALHKVTYLQNGKGRKYFHHNSDFYIPKATLKDSGSYFCRG LVGSKNVSSETVNITITQGLAVSTISSFFPPGYQVSFCLVMV LLFAVDTGLYFSVKTNIRSSTRDWKDHKFKWRKDPQDK | 36 |
| Low affinity immunoglobulin gamma Fc region receptor IIIb (FCγRIIIb) (CD16b)) | MWQLLLPTALLLLVSAGMRTEDLPKAVVFLEPQWYSVLEKDS VTLKCQGAYSPEDNSTQWFHNESLISSQASSYFIDAATVNDS GEYRCQTNLSTLSDPVQLEVHIGWLLLQAPRWVFKEEDPIHL RCHSWKNTALHKVTYLQNGKDRKYFHHNSDFHIPKATLKDSG SYFCRGLVGSKNVSSETVNITITQGLAVSTISSFSPPGYQVS FCLVMVLLFAVDTGLYFSVKTNI | 37 |
| Light chain 1 with constant light chain (VL1-C) | EIVLTQSPAILSLSPGERATLSCRASQRVSSSTYSYMHWYQQ KPGQAPRLLIYDASNRATGIPARFSGSGSGTDFTLTISSLEP EDFAVYYCQHSWEIPPTFGQGTKLEIKRTVAAPSVFIFPPSD EQLKSGTASVVCLLNNFYPREAKVQWKVDNALQSGNSQESVT EQDSKDSTYSLSSTLTLSKADYEKHKVYACEVTHQGLSSPVT KSFNRGEC | 38 |
| Light chain 2 with constant light chain (VL2-C) | EIVLTQSPATLSLSPGERATLSCRADERVSSSTYSYMHW YQQKPGQAPRLLIYDASNRATGIPARFSGSGSGTDFTLT ISSLEPEDFAVYYCQHSWEIPPTFGQGTKLEIKRTVAAP SVFIFPPSDEQLKSGTASVVCLLNNFYPREAKVQNKVDNALQ SGNSQESVTEQDSKDSTYSLSSTLTLSKADYEKHKVYACEVT HQGLSSPVTKSFNRGEC | 39 |
| Light chain 3 with constant light chain (VL3-C) | EIVLTQSPATLSLSPGERATLSCRASQRVSSSTYSYMHW YQQKPGQAPRLLIKYASNRETGIPARFSGSGSGTDFTLT ISSLEPEDFAVYYCQHSWEIPPTFGQGTKLEIKRTVAAP SVFIFPPSDEQLKSGTASVVCLLNNFYPREAKVQNKVDNALQ SGNSQESVTEQDSKDSTYSLSSTLTLSKADYEKHKVYACEVT HQGLSSPVTKSFNRGEC | 40 |
| Light chain 4 with constant light chain (VL4-C) | EIVLTQSPATLSLSPGERATLSCRADERVSSSTYSYMHW YQQKPGQAPRLLIKYASNRETGIPARFSGSGSGTDFTLT ISSLEPEDFAVYYCQHSWEIPPTFGQGTKLEIKRTVAAP SVFIFPPSDEQLKSGTASVVCLLNNFYPREAKVQWKVDNALQ SGNSQESVTEQDSKDSTYSLSSTLTLSKADYEKHKVYACEVT HQGLSSPVTKSFNRGEC | 41 |
| Heavy chain 1-IgG1Fc with P238S and N297G mutations (VH1-Fc-P238/N297) | EPKSCDKTHTCPPCPAPELLGGSSVFLFPPKPKDILMISRTP EVTCVVVDVSHEDPEVKFNWYVDGVEVHNAKTKPREEQYGST YRVVSVLTVLHQDWLNGKEYKCKVSNKALPAPIEKTISKAKG QPREPQVYTLPPSRDELTKNQVSLTCLVKGFYPSDIAVEWES NGQPENNYKTTPPVLDSDGSFFLYSKLTVDKSRWQQGNVFSC SVMHEALHNHYTQKSLSLSPGK | 42 |

TABLE 1 -continued

Sequences

| Description | Sequence | SEQ ID NO: |
|---|---|---|
| Heavy chain 2-IgG1Fc with P238S and N297G mutations (VH2-Fc-P238/N297) | EPKSCDKTHTCPPCPAPELLGGSSVFLFPPKPKDILMISRTP EVTCVVVDVSHEDPEVKFNWYVDGVEVHNAKTKPREEQYGST YRVVSVLTVLHQDWLNGKEYKCKVSNKALPAPIEKTISKAKG QPREPQVYTLPPSRDELTKNQVSLTCLVKGFYPSDIAVEWES NGQPENNYKTTPPVLDSDGSFFLYSKLTVDKSRWQQGNVFSC SVMHEALHNHYTQKSLSLSPGK | 43 |
| Heavy chain 3-IgG1Fc with P238S and N297G mutations (VH3-Fc-P238/N297) | EPKSCDKTHTCPPCPAPELLGGSSVFLFPPKPKDILMISRTP EVTCVVVDVSHEDPEVKFNWYVDGVEVHNAKTKPREEQYGST YRVVSVLTVLHQDWLNGKEYKCKVSNKALPAPIEKTISKAKG QPREPQVYTLPPSRDELTKNQVSLTCLVKGFYPSDIAVEWES NGQPENNYKTTPPVLDSDGSFFLYSKLTVDKSRWQQGNVFSC SVMHEALHNHYTQKSLSLSPGK | 44 |
| Heavy chain 4-IgG1Fc with P238S and N297G mutations (VH4Fc-P238/N297) | EPKSCDKTHTCPPCPAPELLGGSSVFLFPPKPKDILMISRTP EVTCVVVDVSHEDPEVKFNWYVDGVEVHNAKTKPREEQYGST YRVVSVLTVLHQDWLNGKEYKCKVSNKALPAPIEKTISKAKG QPREPQVYTLPPSRDELTKNQVSLTCLVKGFYPSDIAVEWES NGQPENNYKTTPPVLDSDGSFFLYSKLTVDKSRWQQGNVFSC SVMHEALHNHYTQKSLSLSPGK | 45 |
| Heavy chain 1-Fc D265A/N297A effectorless IgG1 (VH1-Fc-D265A/N297A) | EVQLVQSGAEVKKPGASVKVSCKASGYTFTSYYMYWVRQ APGQGLEWMGEINPSNGDTNYAQKFQGRVTMTVDTSTST VYMELSSLRSEDTAVYYCARSDGRNDMDSWGQGTLVTVS SASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPELLGGPSVFL FPPKPKDTLMISRTPEVTCVVVAVSHEDPEVKFNWYVDGVEV HNAKTKPREEQYASTYRVVSVLTVLHQDWLNGKEYKCKVSNK ALPAPIEKTISKAKGQPREPQVYTLPPSRDELTKNQVSLTCL VKGFYPSDIAVEWESNGQPENNYKTTPPVLDSDGSFFLYSKL TVDKSRWQQGNVFSCSVMHEALHNHYTQKSLSLSPG | 46 |
| Heavy chain 2-Fc D265A/N297A effectorless IgG1 (VH2-Fc-D265A/N297A) | EVQLVQSGAEVKKPGASVKVSCKASGYIFTSYYMYWVRQ APGQGLEWMGEINPSNGDTNYAEKFKGRVTMTVDTSTST VYMELSSLRSEDTAVYYCTRSDGRNDMDSWGQGTLVTVS SASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPELLGGPSVFL FPPKPKDTLMISRTPEVTCVVVAVSHEDPEVKFNWYVDGVEV HNAKTKPREEQYASTYRVVSVLTVLHQDWLNGKEYKCKVSNK ALPAPIEKTISKAKGQPREPQVYTLPPSRDELTKNQVSLTCL VKGFYPSDIAVEWESNGQPENNYKTTPPVLDSDGSFFLYSKL TVDKSRWQQGNVFSCSVMHEALHNHYTQKSLSLSPG | 47 |
| Heavy chain 3-Fc D265A/N297A effectorless IgG1 (VH3-Fc-D265A/N297A) | EVQLVQSGAEVKKPGASVKVSCKASGYIFTSYYMYWVRQ APGQGLEWIGEINPSNGDTNYAEKFKGRATLTVDTSTST VYMELSSLRSEDTAVYYCTRSDGRNDMDSWGQGTLVTVS SASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPELLGGPSVFL FPPKPKDTLMISRTPEVTCVVVAVSHEDPEVKFNWYVDGVEV HNAKTKPREEQYASTYRVVSVLTVLHQDWLNGKEYKCKVSNK ALPAPIEKTISKAKGQPREPQVYTLPPSRDELTKNQVSLTCL VKGFYPSDIAVEWESNGQPENNYKTTPPVLDSDGSFFLYSKL TVDKSRWQQGNVFSCSVMHEALHNHYTQKSLSLSPG | 48 |
| Heavy chain 4-Fc D265A/N297A effectorless IgG1 (VH4-Fc-D265A/N297A) | QVQLVQSGAEVKKPGASVKVSCKASGYIFTSYYMYWVRQ APGQGLEWIGEINPSNGDTNFAEKFKGRATLTVDTSTST VYMELSSLRSEDTAVYYCTRSDGRNDMDSWGQGTLVTVS SASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPELLGGPSVFL FPPKPKDTLMISRTPEVTCVVVAVSHEDPEVKFNWYVDGVEV HNAKTKPREEQYASTYRVVSVLTVLHQDWLNGKEYKCKVSNK ALPAPIEKTISKAKGQPREPQVYTLPPSRDELTKNQVSLTCL VKGFYPSDIAVEWESNGQPENNYKTTPPVLDSDGSFFLYSKL TVDKSRWQQGNVFSCSVMHEALHNHYTQKSLSLSPG | 49 |
| Heavy chain 1-Fc effectorless IgG1/IgG4 hybrid (VH1-Fc-IgG1/IgG4 hybrid) | EVQLVQSGAEVKKPGASVKVSCKASGYTFTSYYMYWVRQ APGQGLEWMGEINPSNGDTNYAQKFQGRVTMTVDTSTST VYMELSSLRSEDTAVYYCARSDGRNDMDSWGQGTLVTVS SASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPSCPAPEFLGGPSVFL | 50 |

TABLE 1 -continued

| | Sequences | |
|---|---|---|
| Description | Sequence | SEQ ID NO: |
| | FPPKPKDTLMISRTPEVICVVVDVSQEDPEVQFNWYVDGVEV HNAKTKPREEQFNSKYRVVSVLTVLHQDWLNGKEYKCKVSNK GLPSSIEKTISKAKGQPREPQVYTLPPSREEMTKNQVSLSCA VKGFYPSDIAVEWESNGQPENNYKTTPPVLDSDGSFFLVSKL TVDKSRWQQGNVFSCSVMHEALHNHYTQKSLSLSPG | |
| Heavy chain 2-Fc effectorless IgG1/IgG4 hybrid (VH2-Fc-IgG1/IgG4 hybrid) | EVQLVQSGAEVKKPGASVKVSCKASGYIFTSYYMYWVRQ APGQGLEWMGEINPSNGDTNYAEKFKGRVTMTVDTSTST VYMELSSLRSEDTAVYYCTRSDGRNDMDSWGQGTLVTVS SASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPSCPAPEFLGGPSVFL FPPKPKDTLMISRTPEVICVVVDVSQEDPEVQFNWYVDGVEV HNAKTKPREEQFNSKYRVVSVLTVLHQDWLNGKEYKCKVSNK GLPSSIEKTISKAKGQPREPQVYTLPPSREEMTKNQVSLSCA VKGFYPSDIAVEWESNGQPENNYKTTPPVLDSDGSFFLVSKL TVDKSRWQQGNVFSCSVMHEALHNHYTQKSLSLSPG | 51 |
| Heavy chain 3-Fc effectorless IgG1/IgG4 hybrid (VH3-Fc-IgG1/IgG4 hybrid) | EVQLVQSGAEVKKPGASVKVSCKASGYIFTSYYMYWVRQ APGQGLEWIGEINPSNGDTNYAEKFKGRATLTVDTSTST VYMELSSLRSEDTAVYYCTRSDGRNDMDSWGQGTLVTVS SASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPSCPAPEFLGGPSVFL FPPKPKDTLMISRTPEVICVVVDVSQEDPEVQFNWYVDGVEV HNAKTKPREEQFNSKYRVVSVLTVLHQDWLNGKEYKCKVSNK GLPSSIEKTISKAKGQPREPQVYTLPPSREEMTKNQVSLSCA VKGFYPSDIAVEWESNGQPENNYKTTPPVLDSDGSFFLVSKL TVDKSRWQQGNVFSCSVMHEALHNHYTQKSLSLSPG | 52 |
| Heavy chain 4-Fc effectorless IgG1/IgG4 hybrid (VH4-Fc-IgG1/IgG4 hybrid) | QVQLVQSGAEVKKPGASVKVSCKASGYIFTSYYMYWVRQ APGQGLEWIGEINPSNGDTNFAEKFKGRATLTVDTSTST VYMELSSLRSEDTAVYYCTRSDGRNDMDSWGQGTLVTVS SASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPSCPAPEFLGGPSVFL FPPKPKDTLMISRTPEVICVVVDVSQEDPEVQFNWYVDGVEV HNAKTKPREEQFNSKYRVVSVLTVLHQDWLNGKEYKCKVSNK GLPSSIEKTISKAKGQPREPQVYTLPPSREEMTKNQVSLSCA VKGFYPSDIAVEWESNGQPENNYKTTPPVLDSDGSFFLVSKL TVDKSRWQQGNVFSCSVMHEALHNHYTQKSLSLSPG | 53 |
| Heavy chain 1-Fc effectorless IgG4 constant heavy chain (VH1-Fc-IgG4) | EVQLVQSGAEVKKPGASVKVSCKASGYTFTSYYMYWVRQ APGQGLEWMGEINPSNGDTNYAQKFQGRVTMTVDTSTST VYMELSSLRSEDTAVYYCARSDGRNDMDSWGQGTLVTVS SASTKGPSVFPLAPCSRSTSESTAALGCLVKDYFPEPVTVSW NSGALTSGVHTFPAVLQSSGLYSLSSVVTVPSSSLGTKTYTC NVDHKPSNTKVDKRVESKYGPPCPPCPAPEFLGGPSVFLFPP KPKDILMISRIPEVICVVVDVSQEDPEVQFNWYVDGVEVHNA KTKPREEQFNSKYRVVSVLTVLHQDWLNGKEYKCKVSNKGLP SSIEKTISKAKGQPREPQVYTLPPSQEEMTKNQVSLTCLVKG FYPSDIAVEWESNGQPENNYKTTPPVLDSDGSFFLYSRLTVD KSRWQEGNVFSCSVMHEALHNHYTQKSLSLSLG | 54 |
| Heavy chain 2-Fc effectorless IgG4 constant heavy chain (VH2-Fc-IgG4) | EVQLVQSGAEVKKPGASVKVSCKASGYIFTSYYMYWVRQ APGQGLEWMGEINPSNGDTNYAEKFKGRVTMTVDTSTST VYMELSSLRSEDTAVYYCTRSDGRNDMDSWGQGTLVTVS SASTKGPSVFPLAPCSRSTSESTAALGCLVKDYFPEPVTVSW NSGALTSGVHTFPAVLQSSGLYSLSSVVTVPSSSLGTKTYTC NVDHKPSNTKVDKRVESKYGPPCPPCPAPEFLGGPSVFLFPP KPKDILMISRIPEVICVVVDVSQEDPEVQFNWYVDGVEVHNA KTKPREEQFNSKYRVVSVLTVLHQDWLNGKEYKCKVSNKGLP SSIEKTISKAKGQPREPQVYTLPPSQEEMTKNQVSLTCLVKG FYPSDIAVEWESNGQPENNYKTTPPVLDSDGSFFLYSRLTVD KSRWQEGNVFSCSVMHEALHNHYTQKSLSLSLG | 55 |
| Heavy chain 3-Fc effectorless IgG4 constant heavy chain (VH3-Fc-IgG4) | EVQLVQSGAEVKKPGASVKVSCKASGYIFTSYYMYWVRQ APGQGLEWIGEINPSNGDTNYAEKFKGRATLTVDTSTST VYMELSSLRSEDTAVYYCTRSDGRNDMDSWGQGTLVTVS SASTKGPSVFPLAPCSRSTSESTAALGCLVKDYFPEPVTVSW NSGALTSGVHTFPAVLQSSGLYSLSSVVTVPSSSLGTKTYTC NVDHKPSNTKVDKRVESKYGPPCPPCPAPEFLGGPSVFLFPP KPKDILMISRIPEVICVVVDVSQEDPEVQFNTNYVDGVEVHNA KTKPREEQFNSKYRVVSVLTVLHQDTA7LNGKEYKCKVSNKGLP SSIEKTISKAKGQPREPQVYTLPPSQEEMTKNQVSLTCLVKG | 56 |

TABLE 1 -continued

Sequences

| Description | Sequence | SEQ ID NO: |
|---|---|---|
| | FYPSDIAVETNESNGQPENNYKTTPPVLDSDGSFFLYSRLTVD KSRWQEGNVFSCSVMHEALHNHYTQKSLSLSLG | |
| Heavy chain 4-Fc effectorless IgG4 constant heavy chain (VH4-Fc-IgG4) | QVQLVQSGAEVKKPGASVKVSCKASGYIFTSYYMYWVRQ APGQGLEWIGEINPSNGDTNFAEKFKGRATLTVDTSTST VYMELSSLRSEDTAVYYCTRSDGRNDMDSWGQGTLVTVS SASTKGPSVFPLAPCSRSTSESTAALGCLVKDYFPEPVTVSW NSGALTSGVHTFPAVLQSSGLYSLSSVVTVPSSSLGTKTYTC NVDHKPSNTKVDKRVESKYGPPCPPCPAPEFLGGPSVFLFPP KPKDILMISRIPEVICVVVDVSQEDPEVQFNTNYVDGVEVHNA KTKPREEQFNSKYRVVSVLTVLHQDTA7LNGKEYKCKVSNKGLP SSIEKTISKAKGQPREPQVYTLPPSQEEMTKNQVSLTCLVKG FYPSDIAVETNESNGQPENNYKTTPPVLDSDGSFFLYSRLTVD KSRWQEGNVFSCSVMHEALHNHYTQKSLSLSLG | 57 |

Examples

Example 1 CD40L Binding Assay

In order to make a comparison of CD40L binding of antibodies from all 16 clones versus 5c8 or AT-1501 a binding assay was run using 2 clones with 5c8 and AT-1501 run on the same 96-well assay plate. A three part sandwich ELISA assay was used to determine the level of binding of the antibodies of the present disclosure in comparison to reference antibodies 5c8-19 and AT1501. 96-well polystyrene plates were coated with recombinant human CD40L (BioLegend Cat. #591706) using 2 ug/ml in PBS and 50 ul/well was added to Costar 96-well ½ area high binding assay plates (Corning 3690) and incubated overnight at 4° C. Plates were blocked with (1×) PBS/1.0% BSA (140 ul/well) for 1 hour at room temperature to prevent background binding. Binding curves of 5C8 or AT1501 (from 2 ug/ml out serial 2-fold dilutions) were added (50 ul/well) and incubated for 1 hour at room temperature. Plates are washed and incubated with HRP-(Fab2) donkey anti-human IgG (Fc specific) (Jackson Immuno. 709-036-098) at a 1:10,000 dilution (50 ul/well) for 1 hour at room temperature. Plates were washed and TMB substrate (Surmodics BioFX TMBW-1000-01) was added (50 ul/well). Color development is stopped after 5 minutes at room temperature with 25 ul 2NH$_2$SO$_4$. Plates are read on Molecular Devices SpectraMax M5 plate reader using SoftMax Pro 6.2.2 program to determine absorbance at 450 nm.

TABLE 2

| FIG. No. | Clone | IC50 | LCL | UCL | Rel. Pot. |
|---|---|---|---|---|---|
| 2A | 16-3 | 0.022 | 0.017 | 0.026 | 46 |
| | 5c8 | 0.047 | 0.040 | 0.054 | |
| 2B | 8-3 | 0.036 | 0.028 | 0.043 | 51 |
| | 5c8 | 0.070 | 0.062 | 0.078 | |
| 2C | 12-4 | 0.020 | 0.013 | 0.027 | 47 |
| | 5c8 | 0.042 | 0.038 | 0.046 | |
| 2D | 8-4 | 0.036 | 0.030 | 0.041 | 51 |
| | 5c8 | 0.070 | 0.062 | 0.078 | |
| 2E | 13-2 | 0.020 | 0.013 | 0.027 | 48 |
| | 5c8 | 0.041 | 0.038 | 0.045 | |
| 2F | 4-4 | 0.037 | 0.029 | 0.045 | 51 |
| | 5c8 | 0.072 | 0.064 | 0.081 | |
| 2G | 17-1 | 0.028 | 0.023 | 0.033 | 63 |
| | 5c8 | 0.044 | 0.036 | 0.053 | |
| 2H | AT-1501 | 0.049 | 0.043 | 0.056 | 95 |
| | 5c8 | 0.052 | 0.046 | 0.058 | |
| 2I | 5-3 | 0.055 | 0.047 | 0.063 | 76 |
| | 5c8 | 0.072 | 0.064 | 0.081 | |
| 2J | 6-6 | 0.065 | 0.059 | 0.070 | 106 |
| | 5c8 | 0.061 | 0.054 | 0.068 | |
| 2K | 18-2 | 0.041 | 0.036 | 0.046 | 92 |
| | 5c8 | 0.044 | 0.036 | 0.053 | |
| 2L | 10-4 | 0.075 | 0.065 | 0.086 | 113 |
| | 5c8 | 0.067 | 0.058 | 0.076 | |
| 2M | 10-1 | 0.079 | 0.070 | 0.089 | 119 |
| | 5c8 | 0.067 | 0.058 | 0.076 | |
| 2N | 7-5 | 0.102 | 0.094 | 0.111 | 168 |
| | 5c8 | 0.061 | 0.054 | 0.068 | |
| 2O | 15.4 | 0.063 | 0.056 | 0.069 | 133 |
| | 5c8 | 0.047 | 0.040 | 0.054 | |
| 2P | 11-5 | 0.092 | 0.071 | 0.112 | 177 |
| | 5c8 | 0.052 | 0.046 | 0.058 | |
| 2Q | 15-1 | 0.081 | 0.073 | 0.089 | 163 |
| | 5c8 | 0.050 | 0.046 | 0.053 | |

Figure 1A:
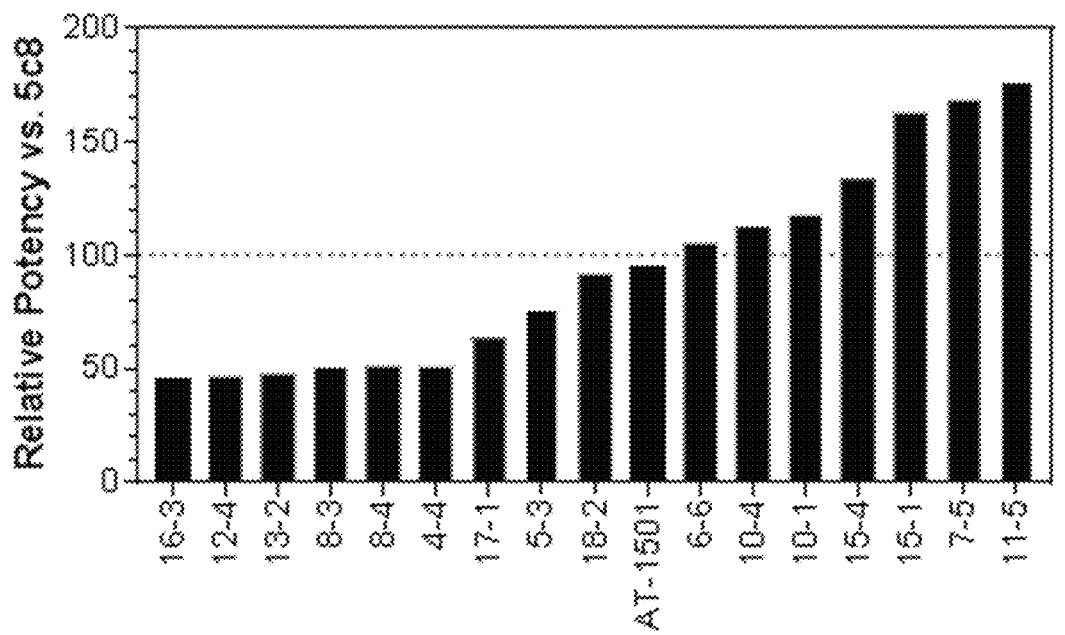
FIG. 1A is a bar graph showing the ranked potency of 16 antibody clones versus the anti-CD40L antibody 5c8. Ranked potency is IC50 clone/IC50 of 5c8×100.
Figure 1B:
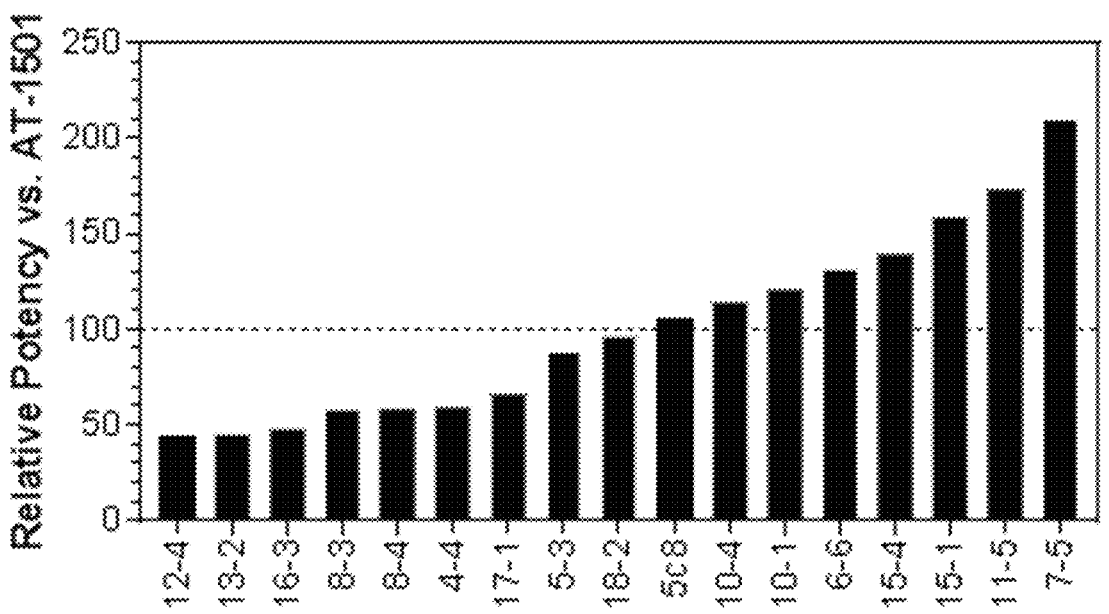
FIG. 1B is a bar graph showing the ranked potency of 16 antibody clones versus the anti-CD40L antibody AT-1501. Ranked potency is IC50 clone/IC50 of AT-1501×100.
Figure 2A:
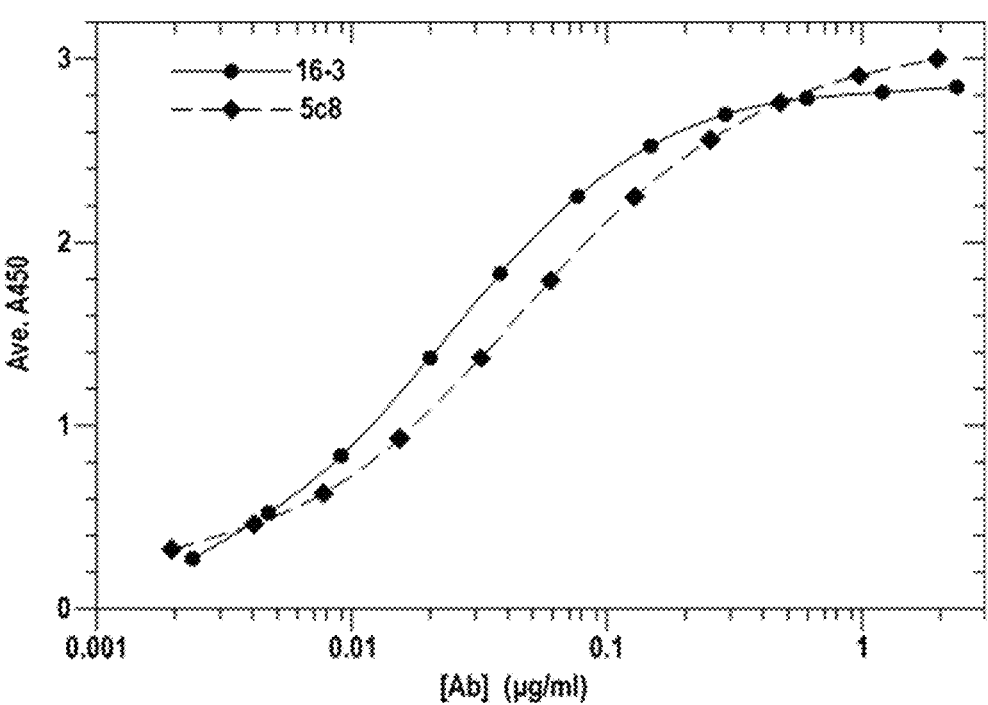
FIGS. 2A-2G and 2I-2Q show the binding curves of the antibodies from each of the clones with the binding curve for 5c8.
Figure 2B:
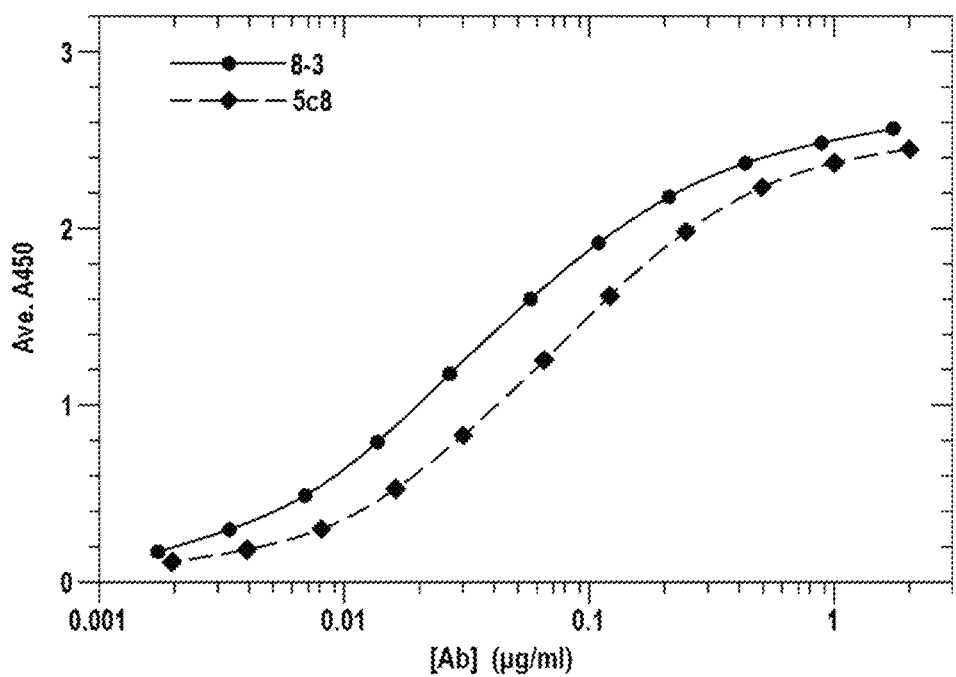
Figure 2C:
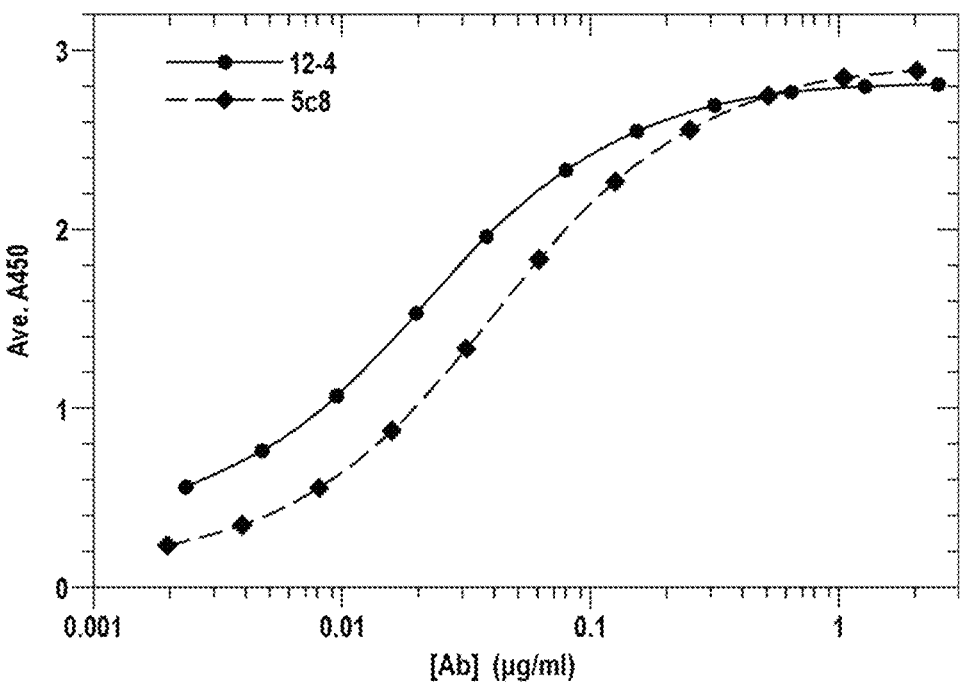
Figure 2D:
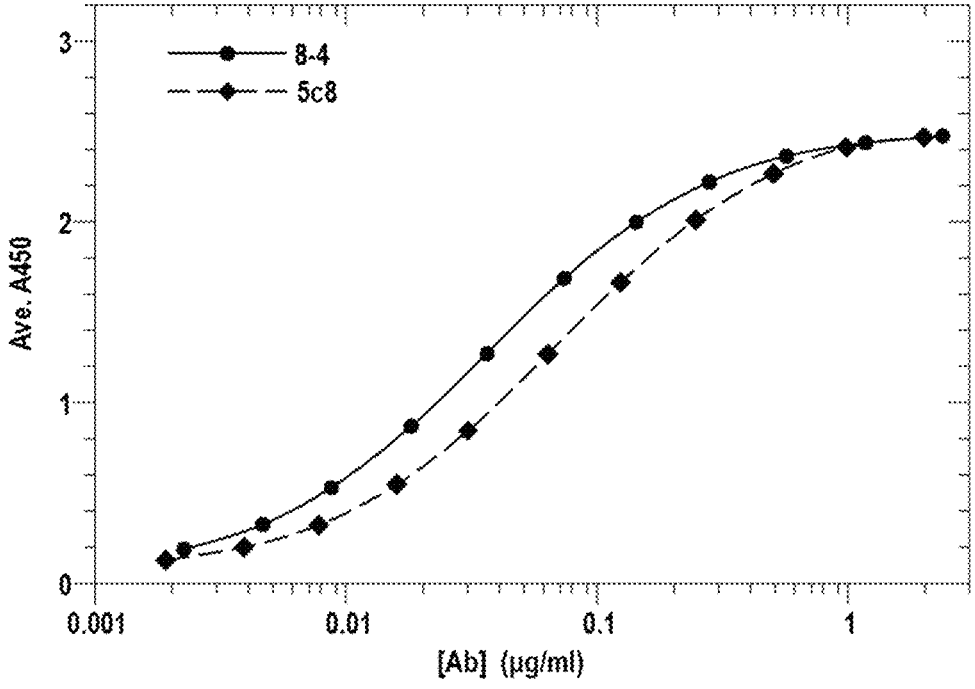
Figure 2E:
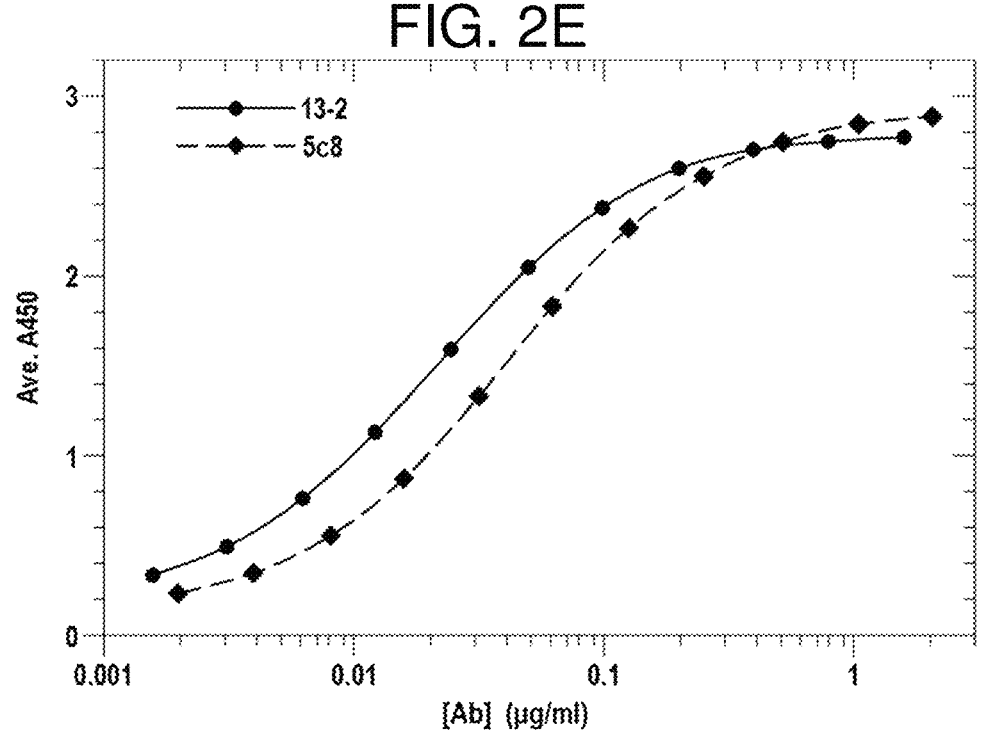
Figure 2F:
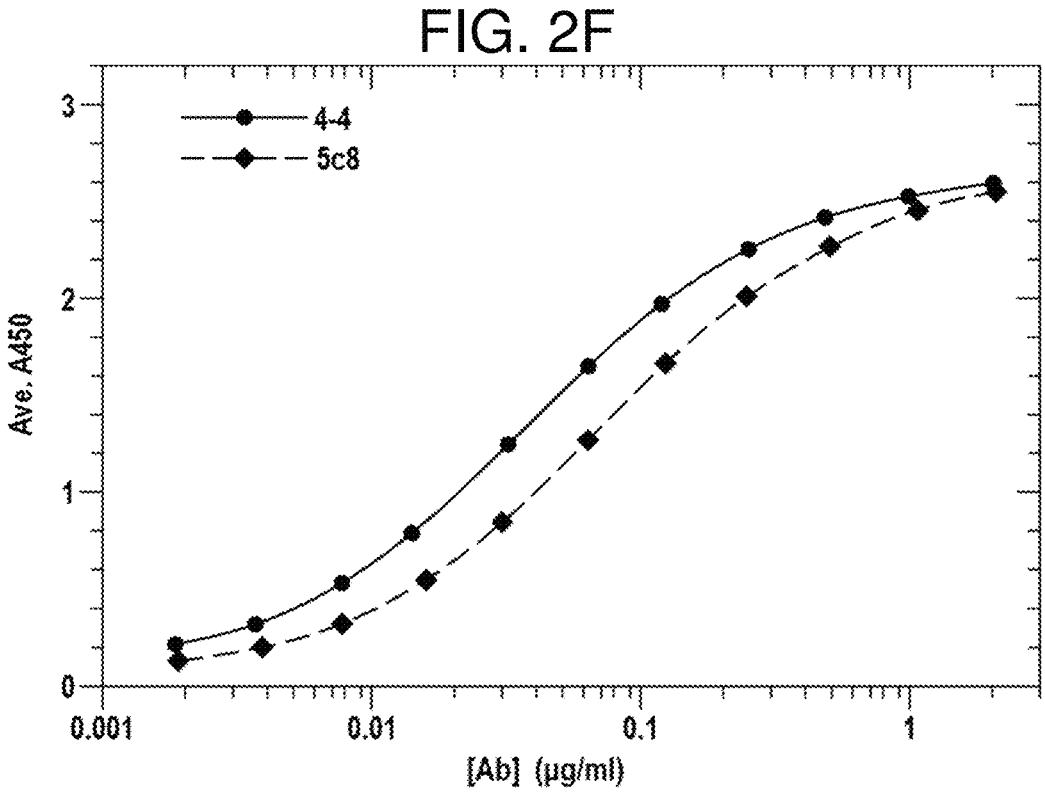
Figure 2G:
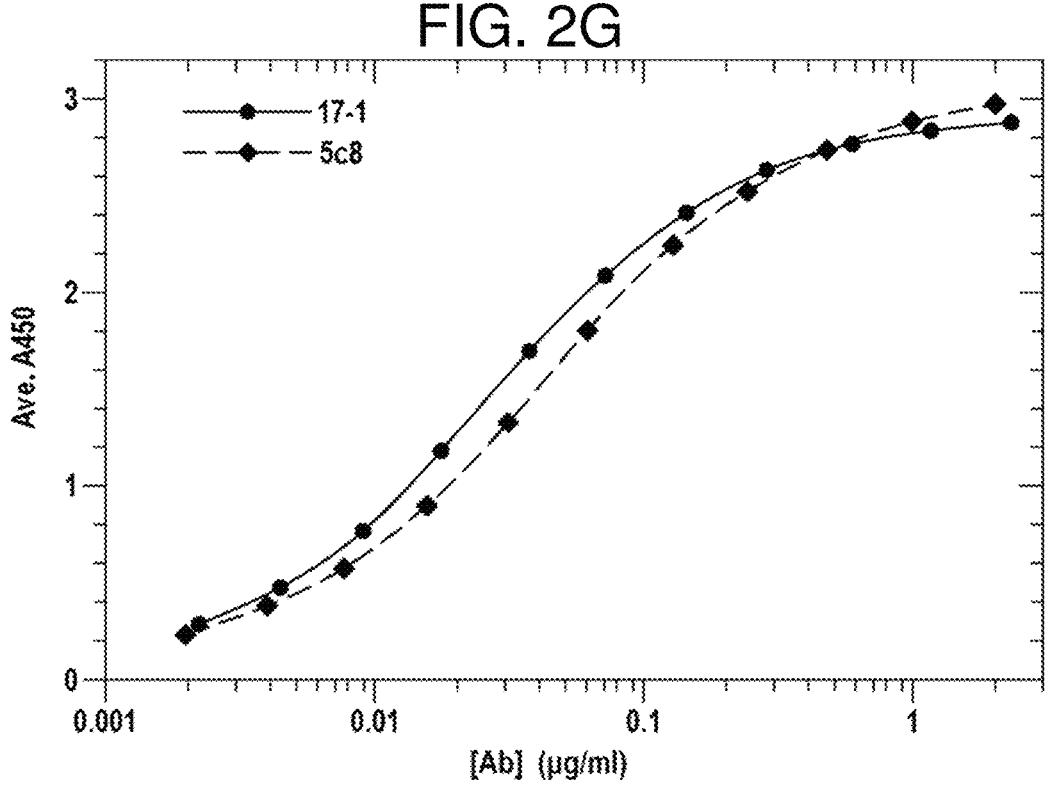
Figure 2H:
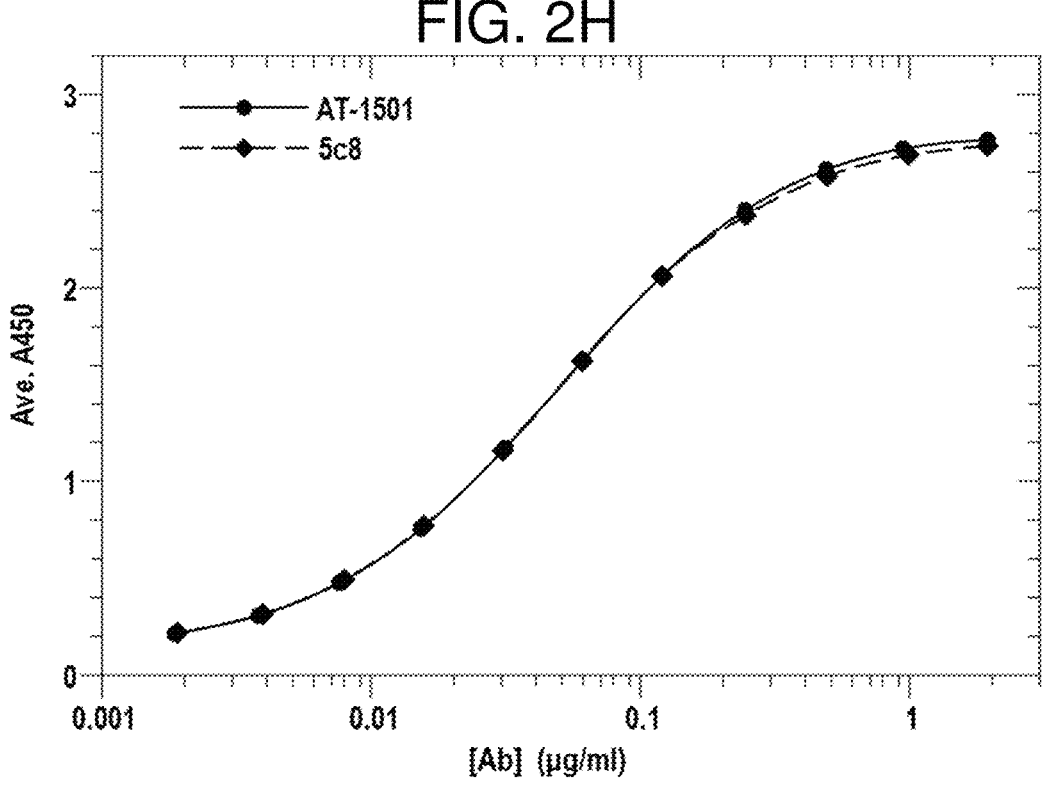
FIG. 2H shows the binding curves of AT-1501 and 5c8.
Figure 2I:
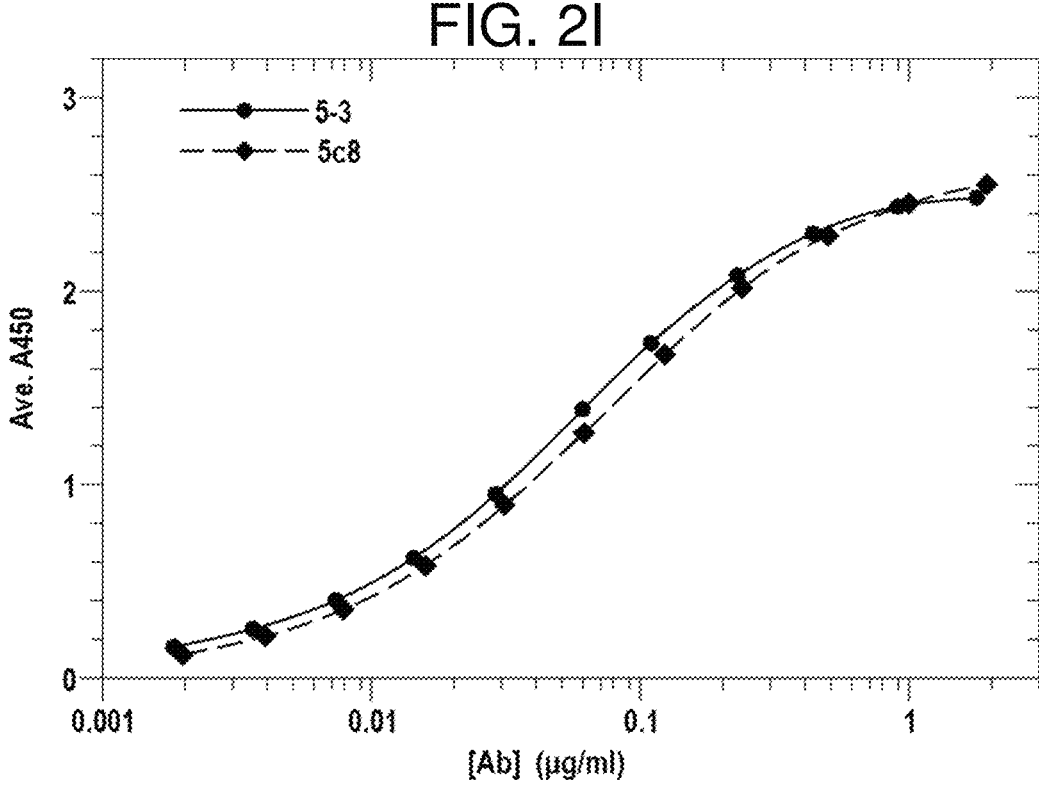
Figure 2J:
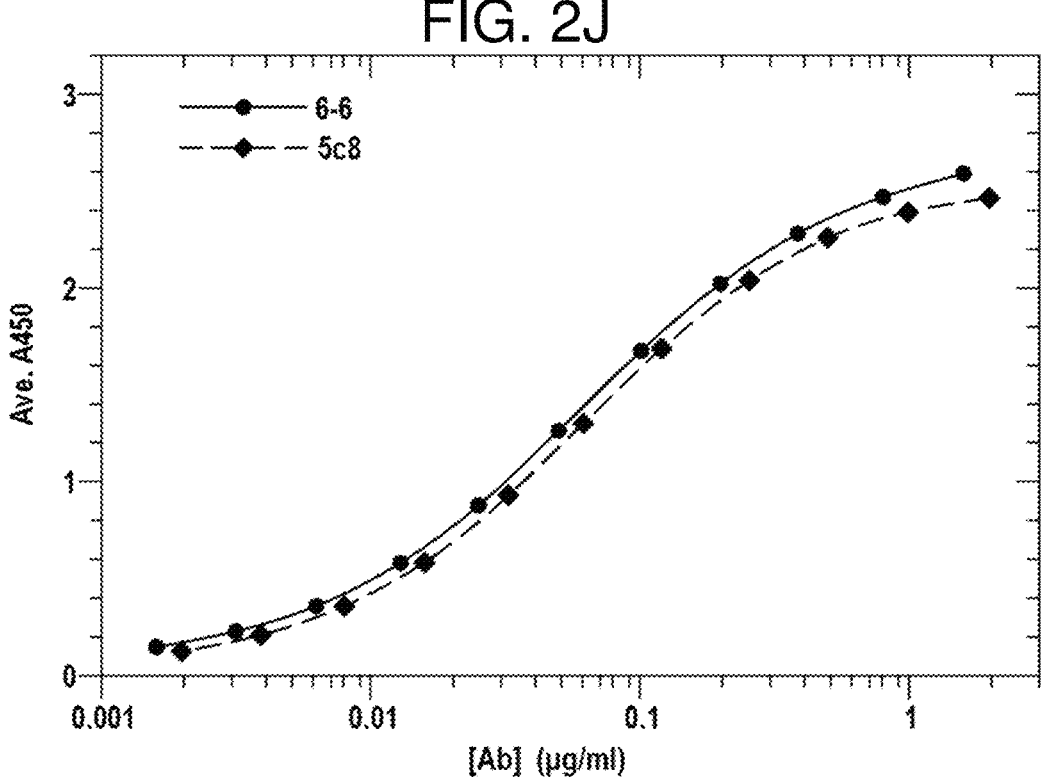
Figure 2K:
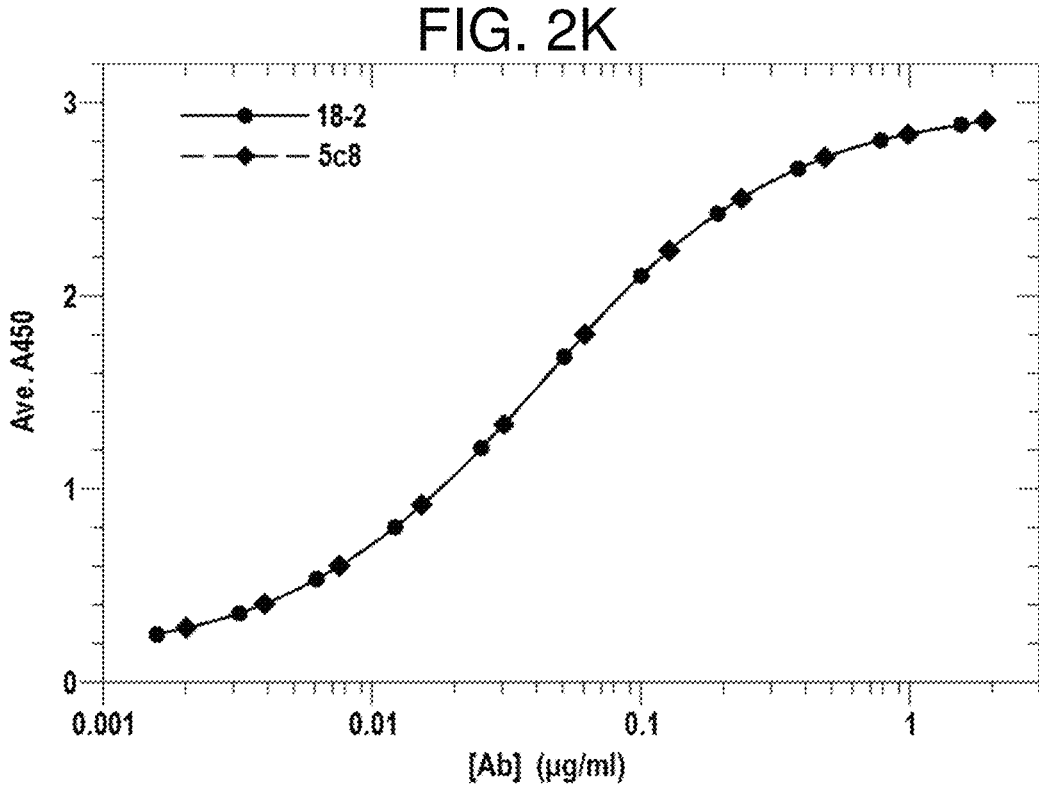
Figure 2L:
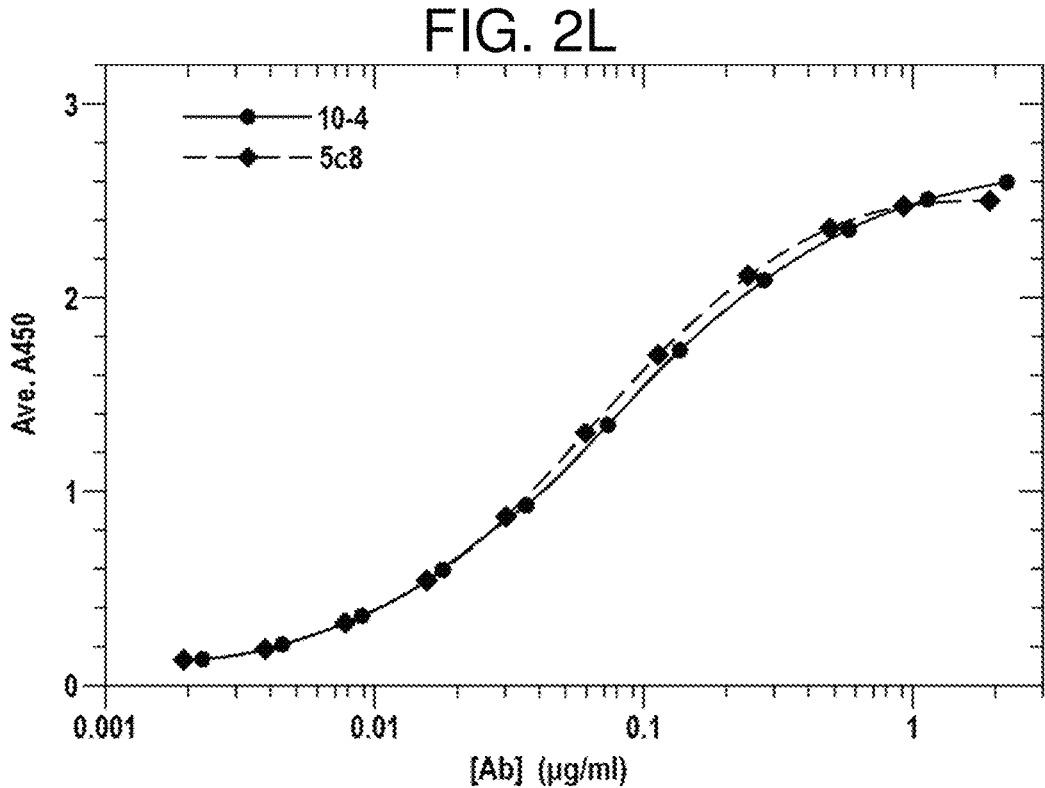
Figure 2M:
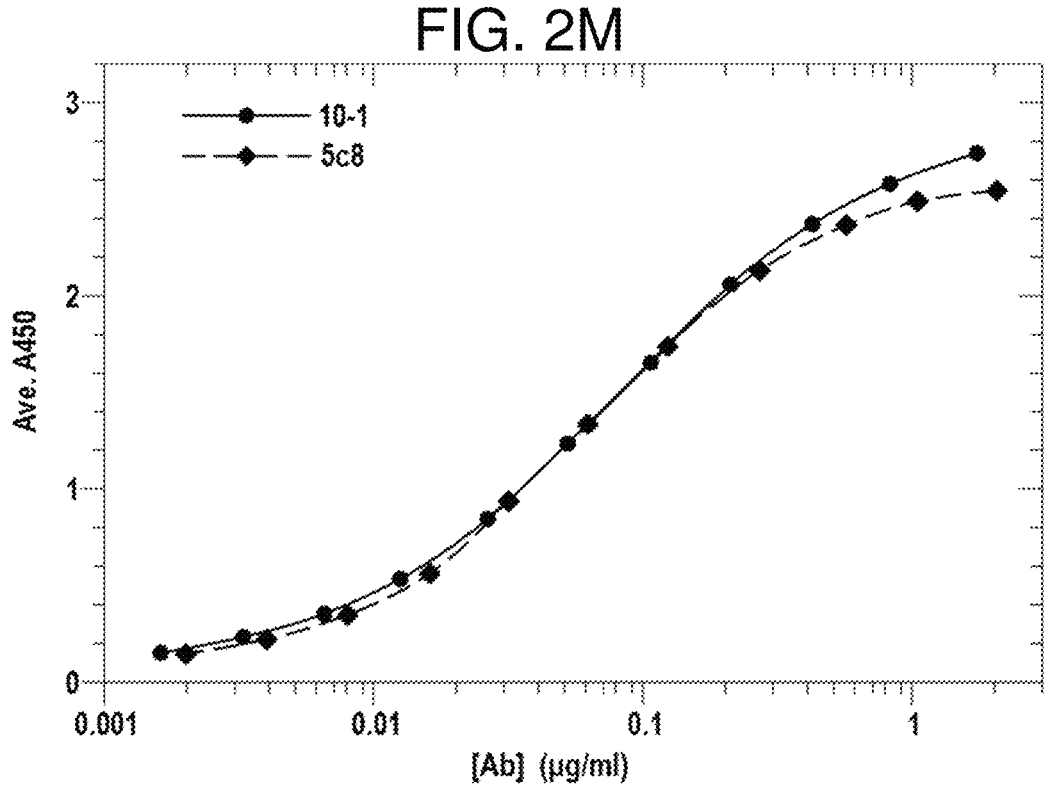
Figure 2N:
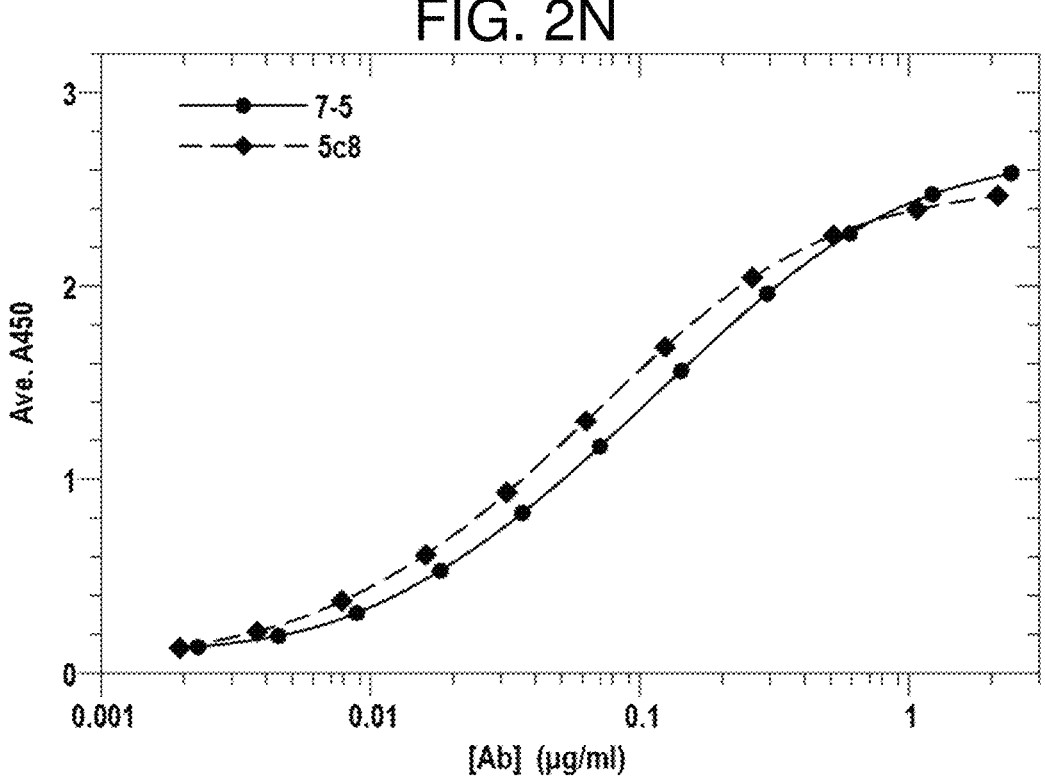
Figure 2O:
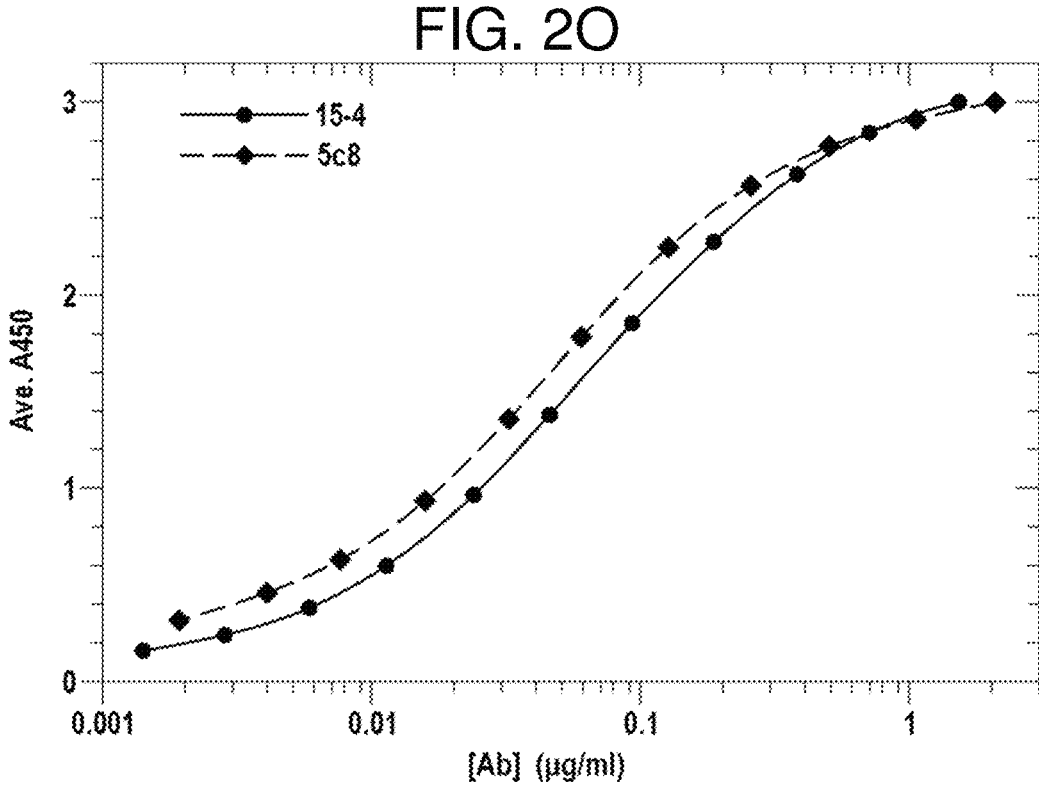
Figure 2P:
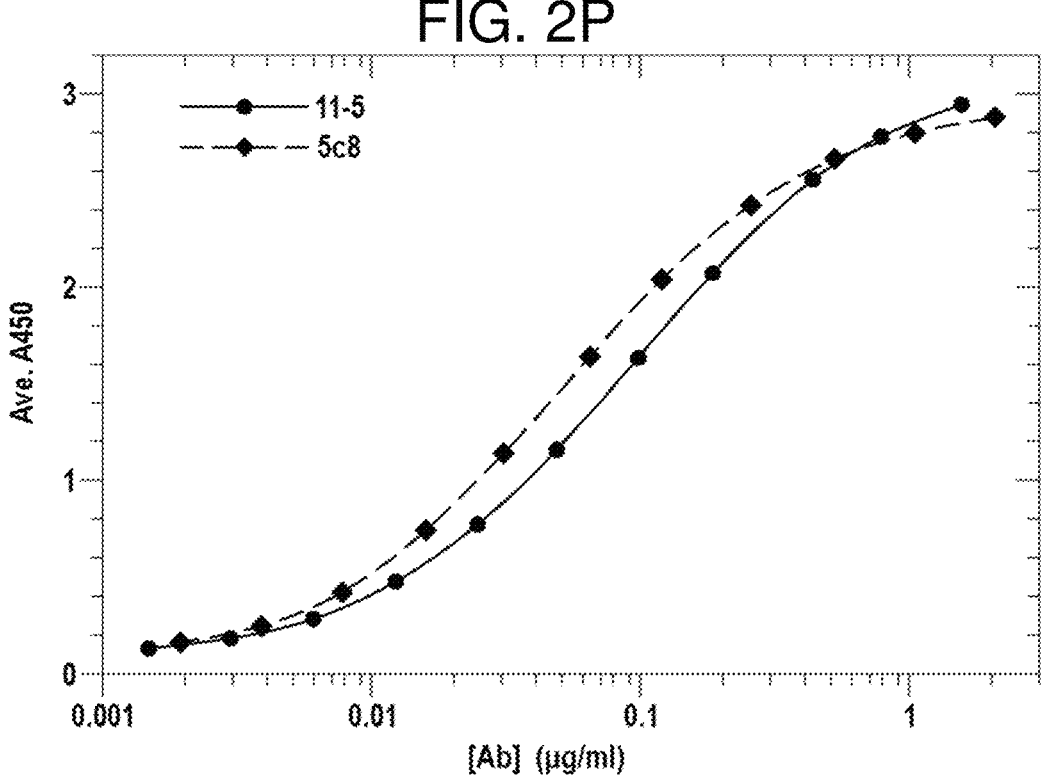
Figure 2Q:
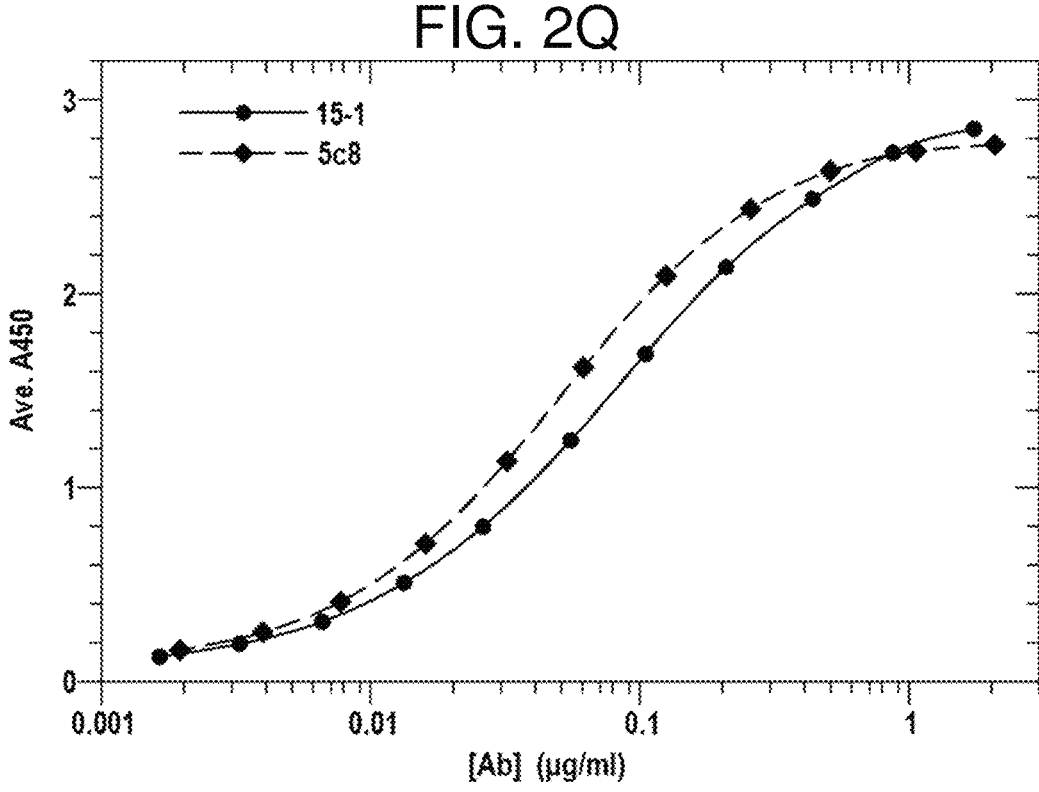
Figure 3A:
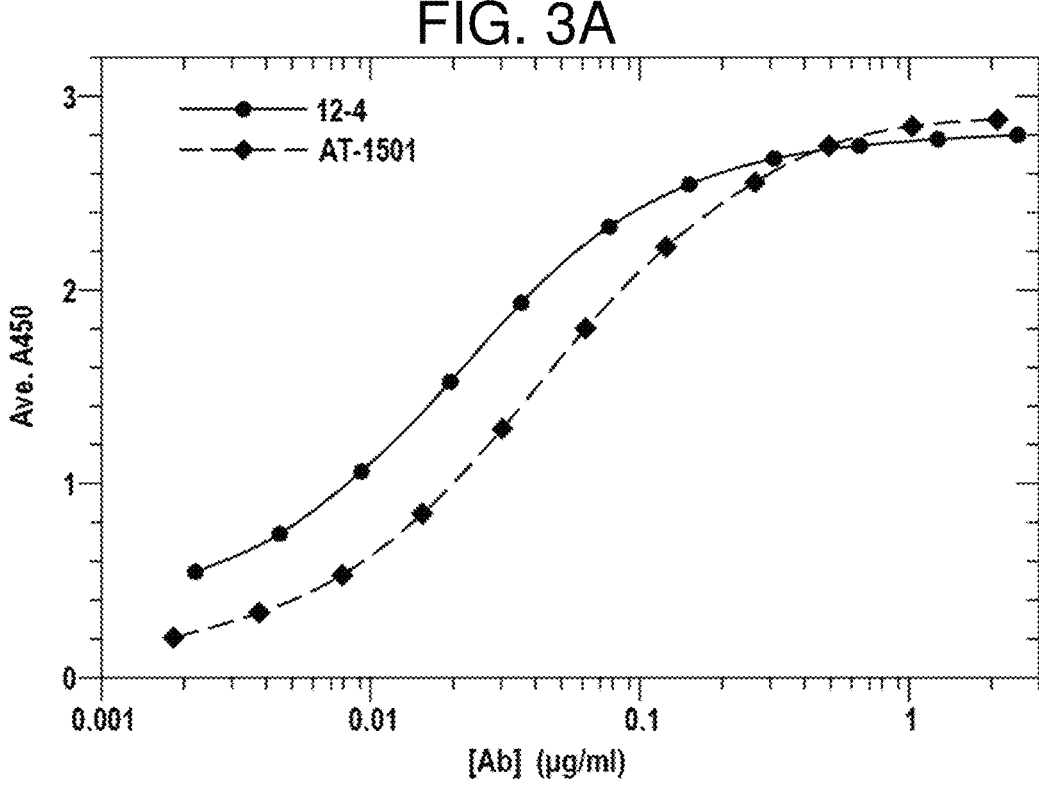
FIGS. 3A-3G and 3I-3Q show the binding curves of the antibodies from each of the clones with the binding curve for AT-1501.
Figure 3B:
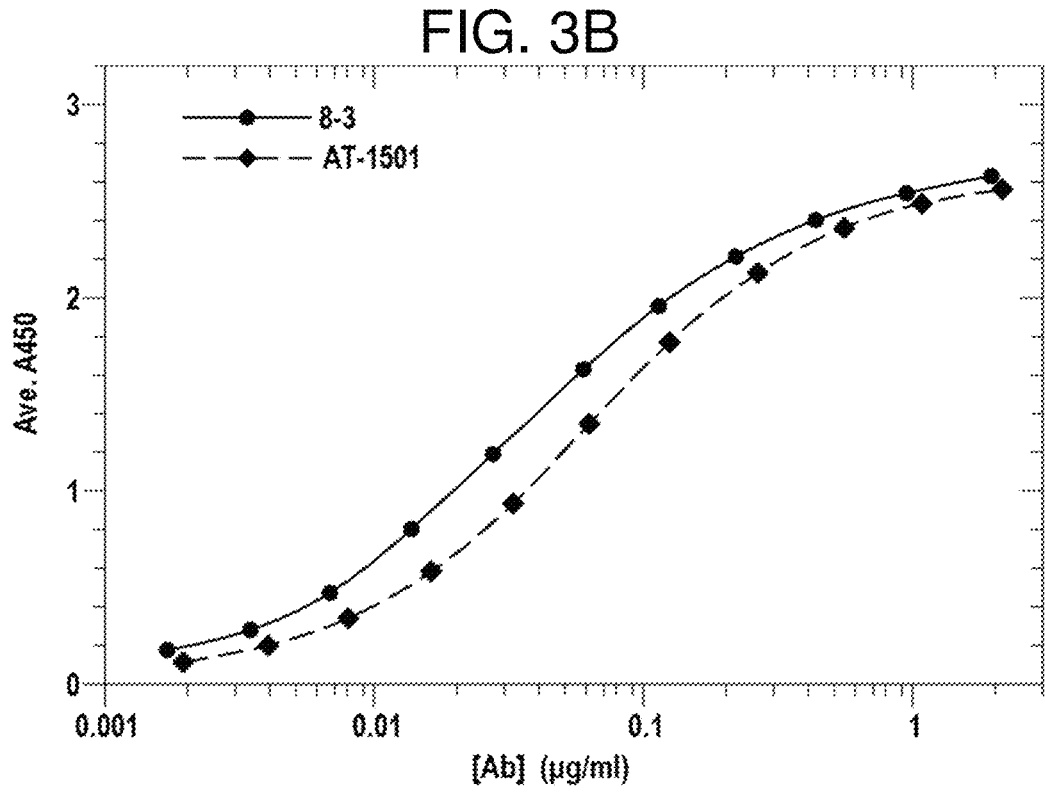
Figure 3C:
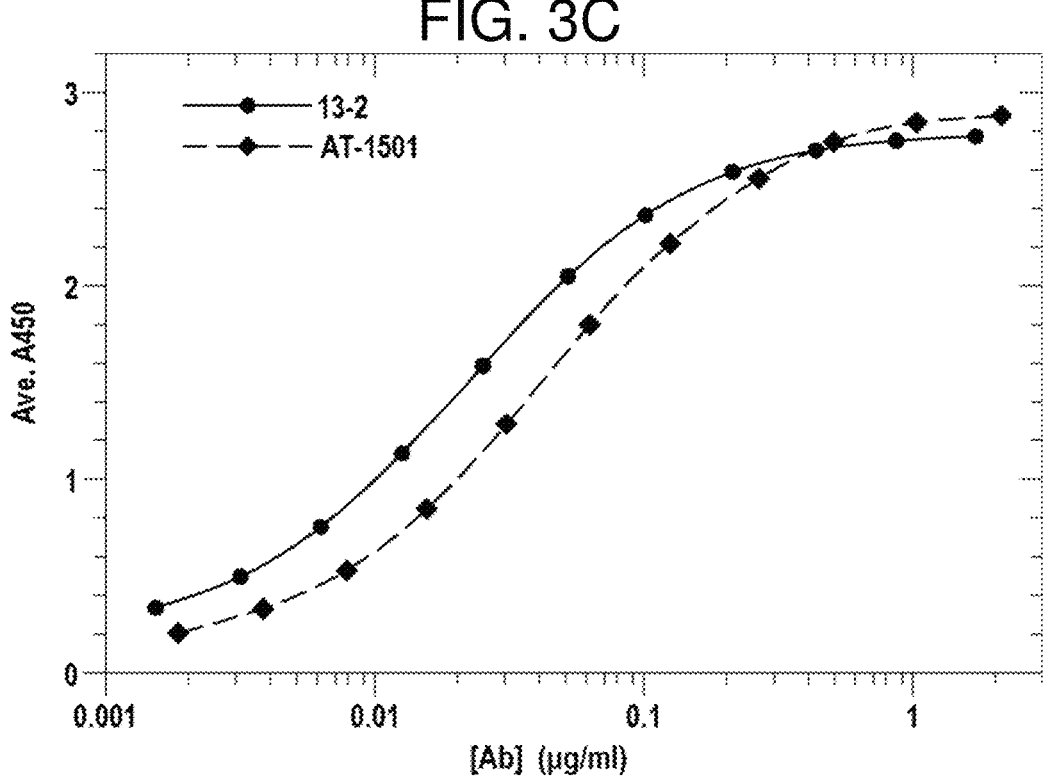
Figure 3D:
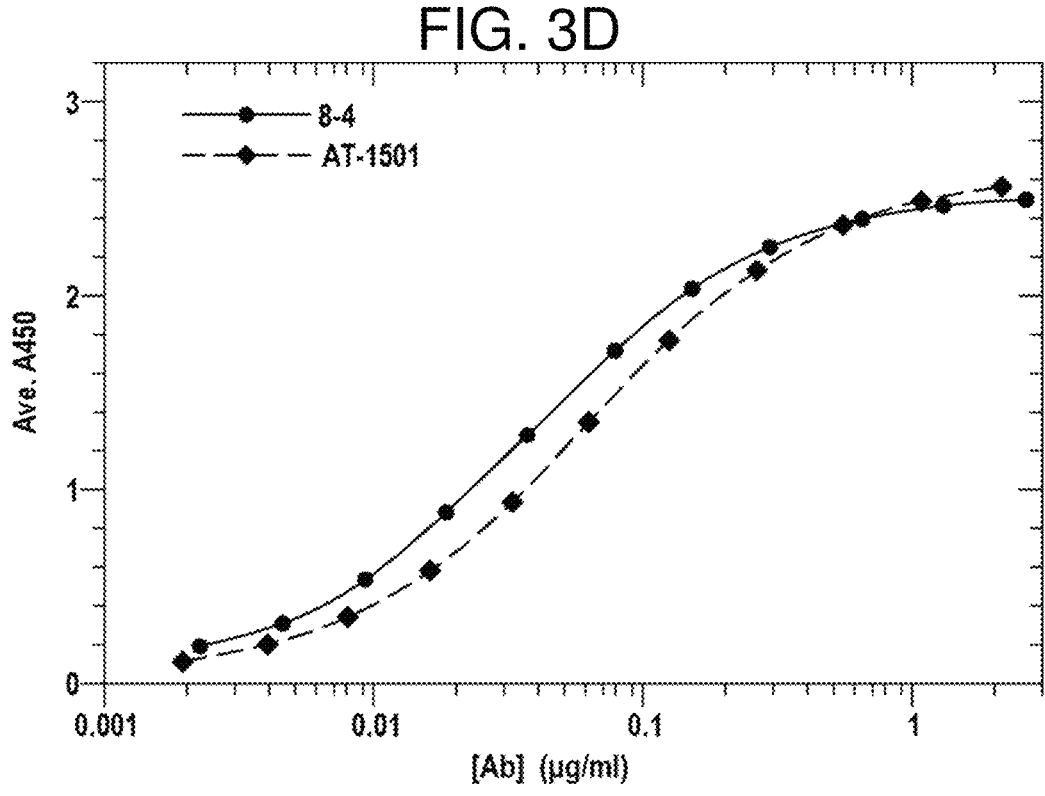
Figure 3E:
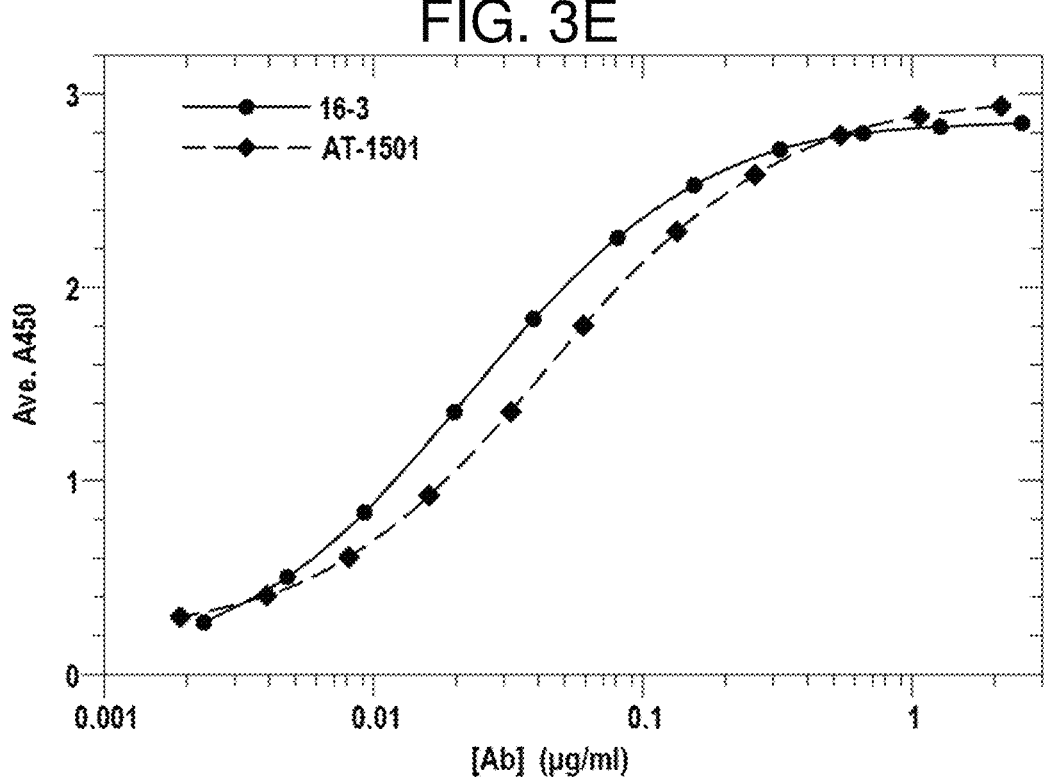
Figure 3F:
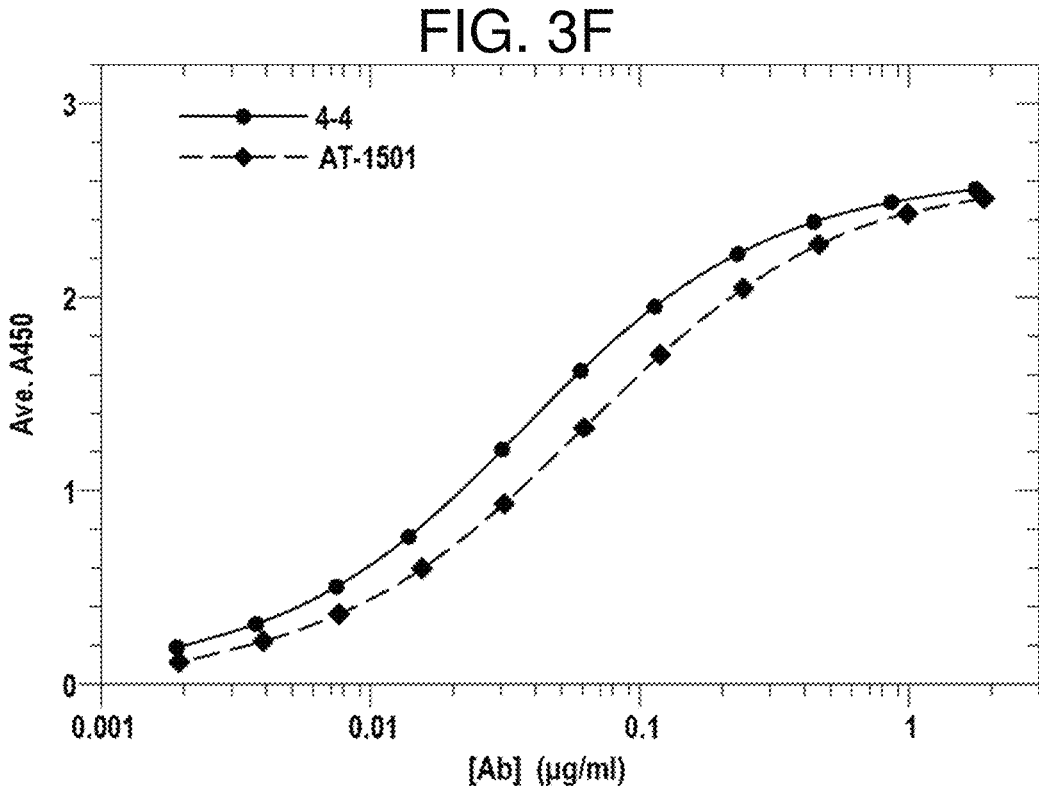
Figure 3G:
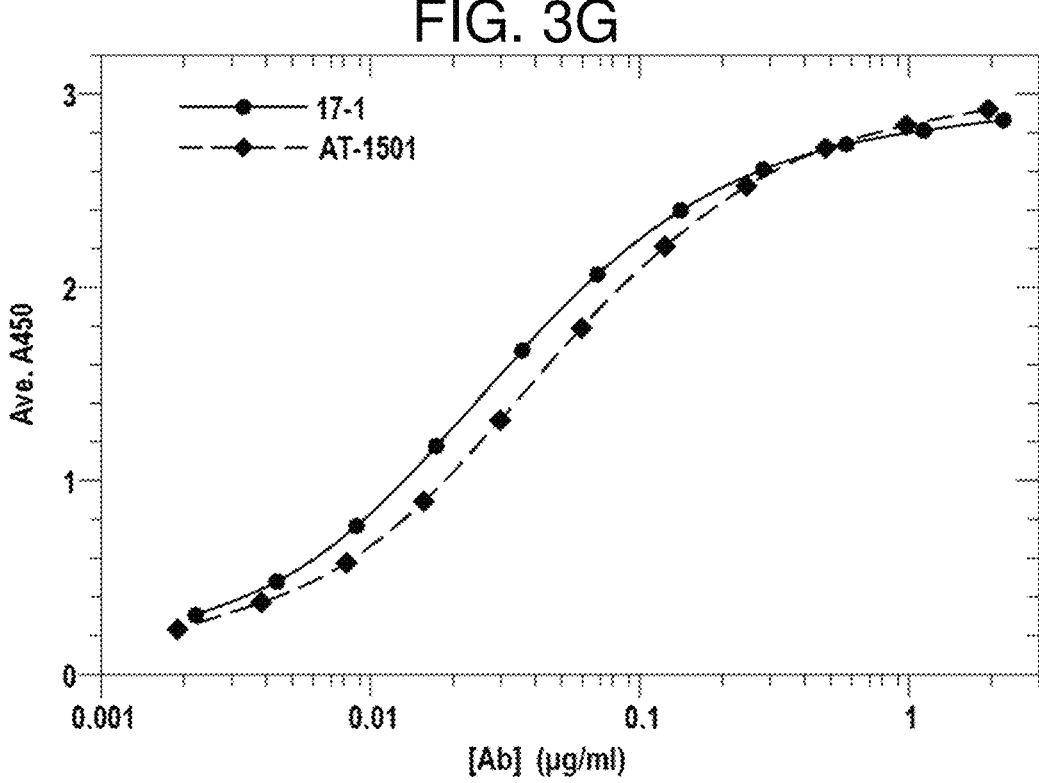
Figure 3H:
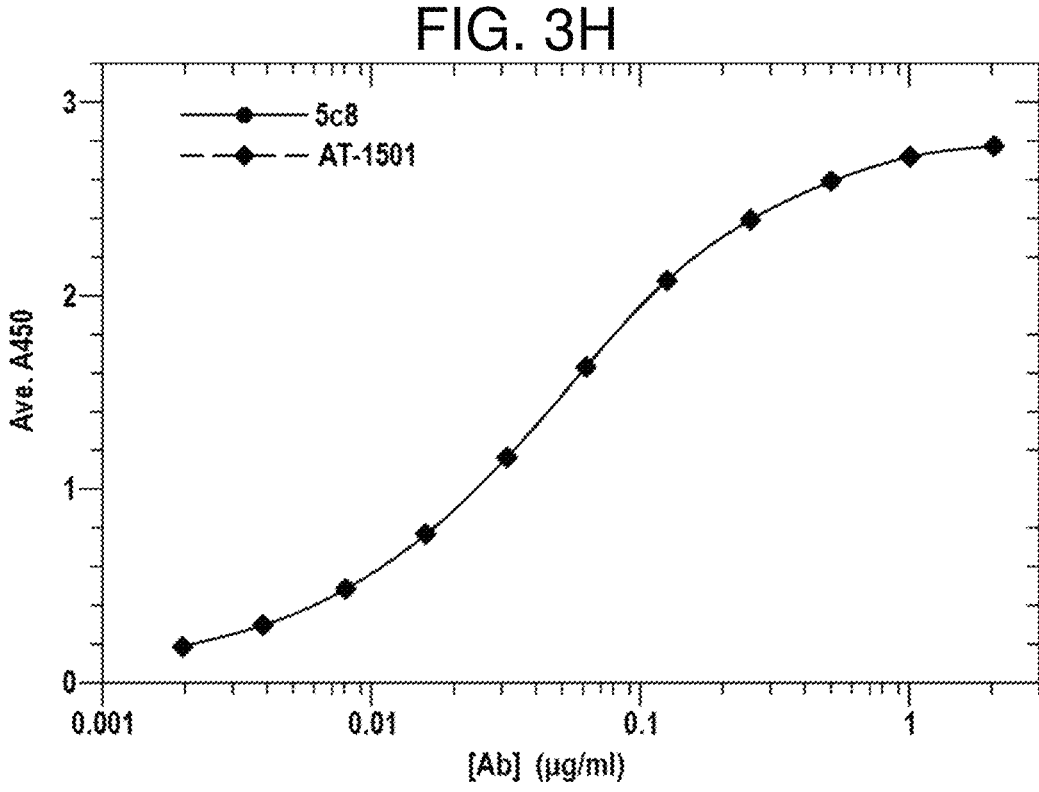
FIG. 3H shows the binding curves of AT-1501 and 5c8.
Figure 3I:
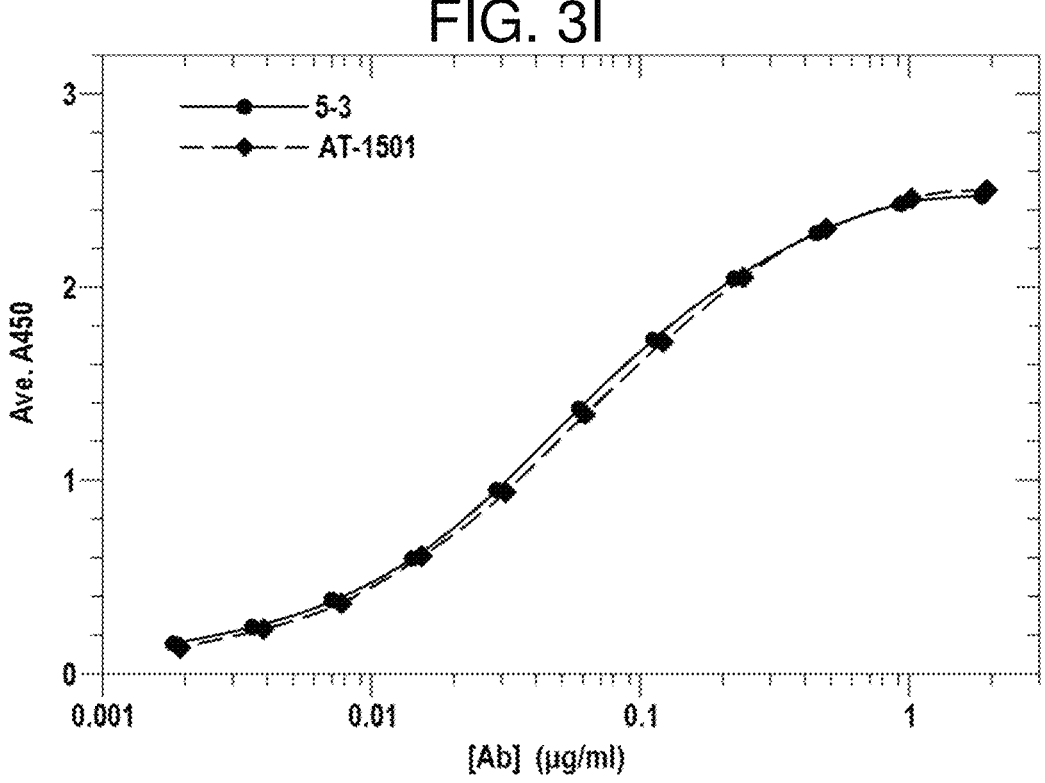
Figure 3J:
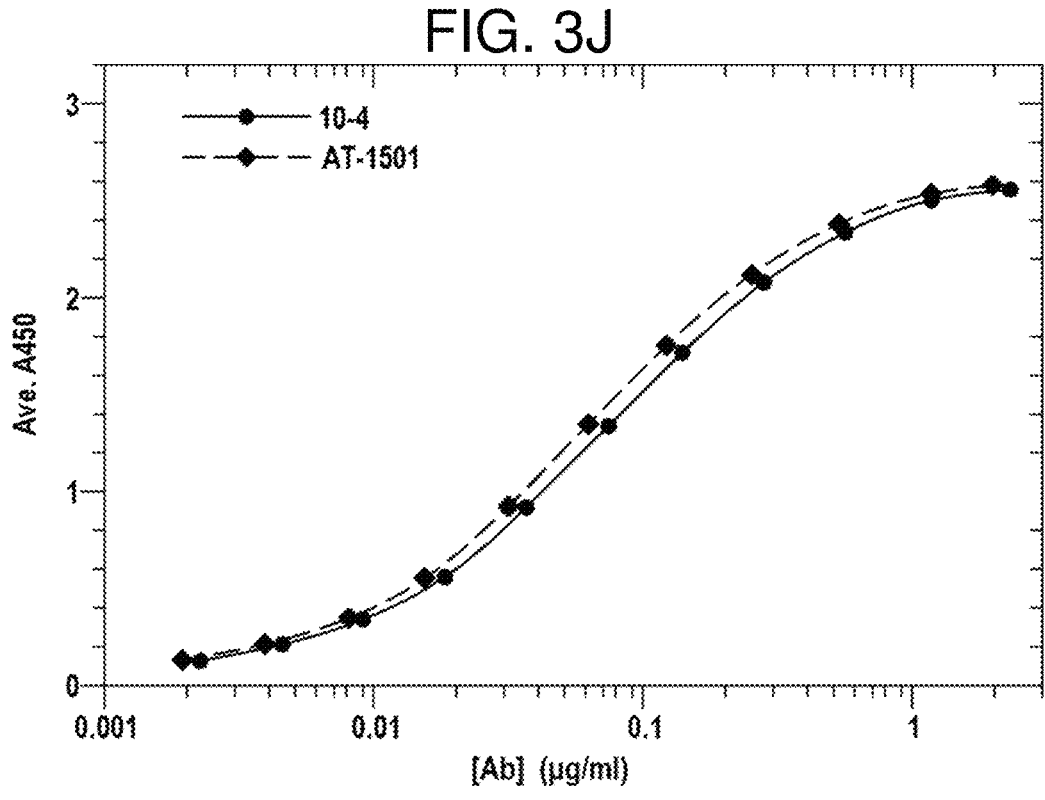
Figure 3K:
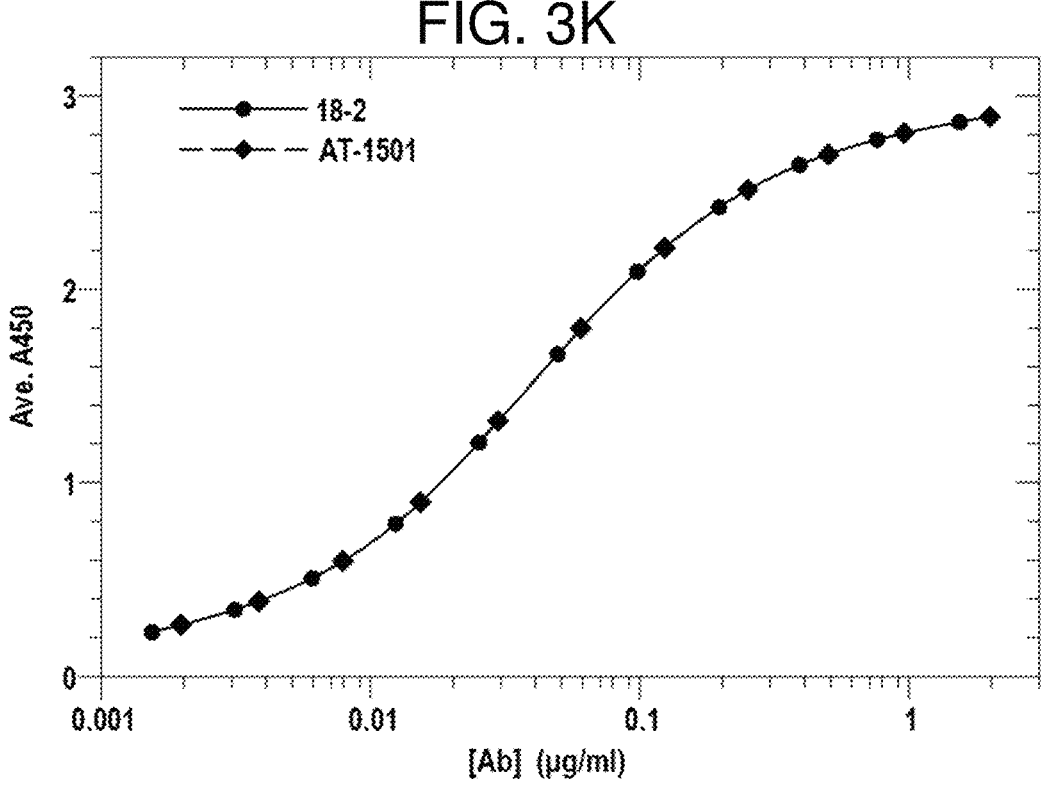
Figure 3L:
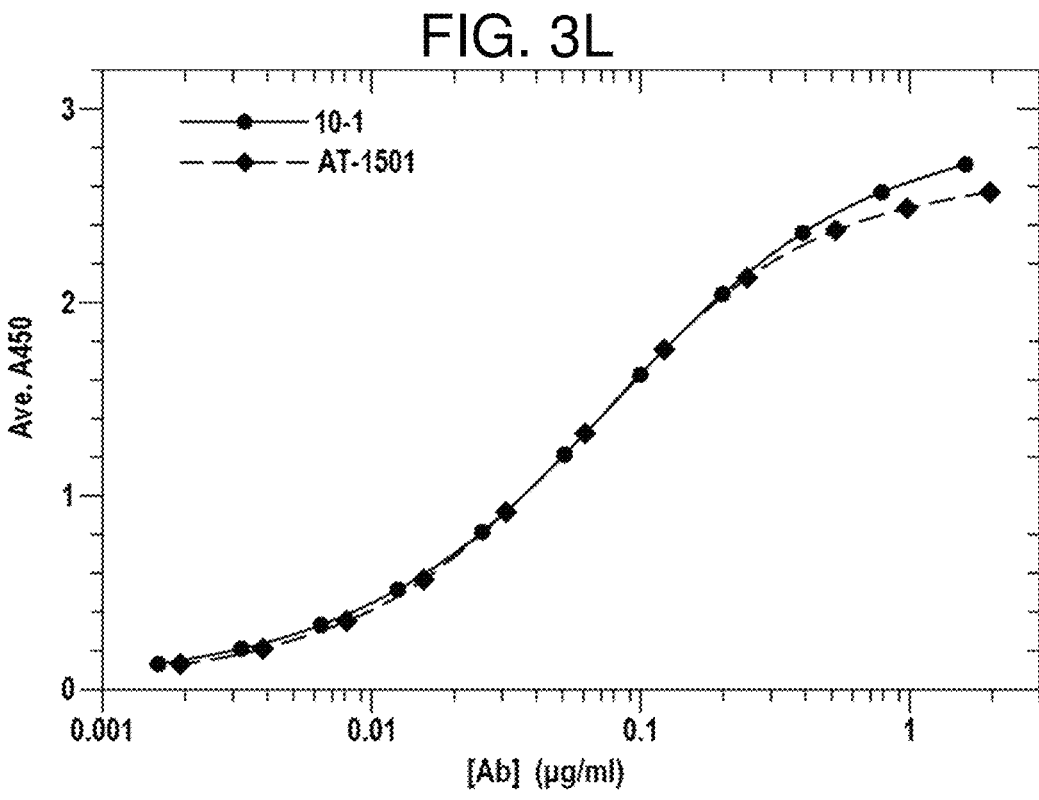
Figure 3M:
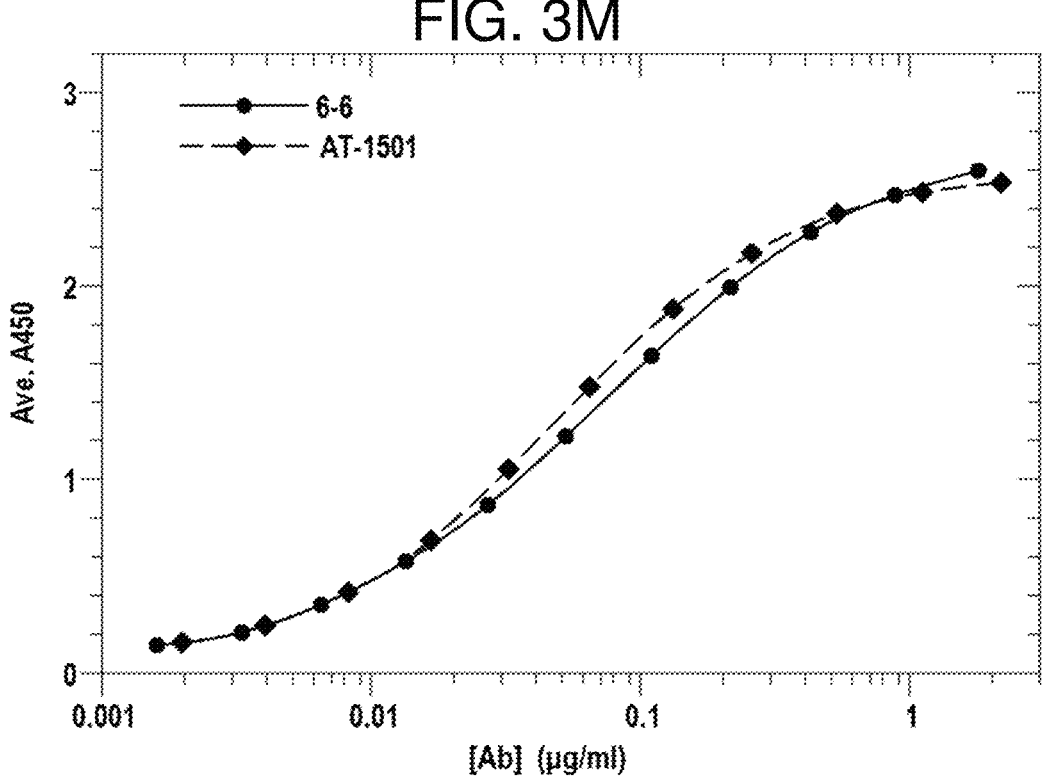
Figure 3N:
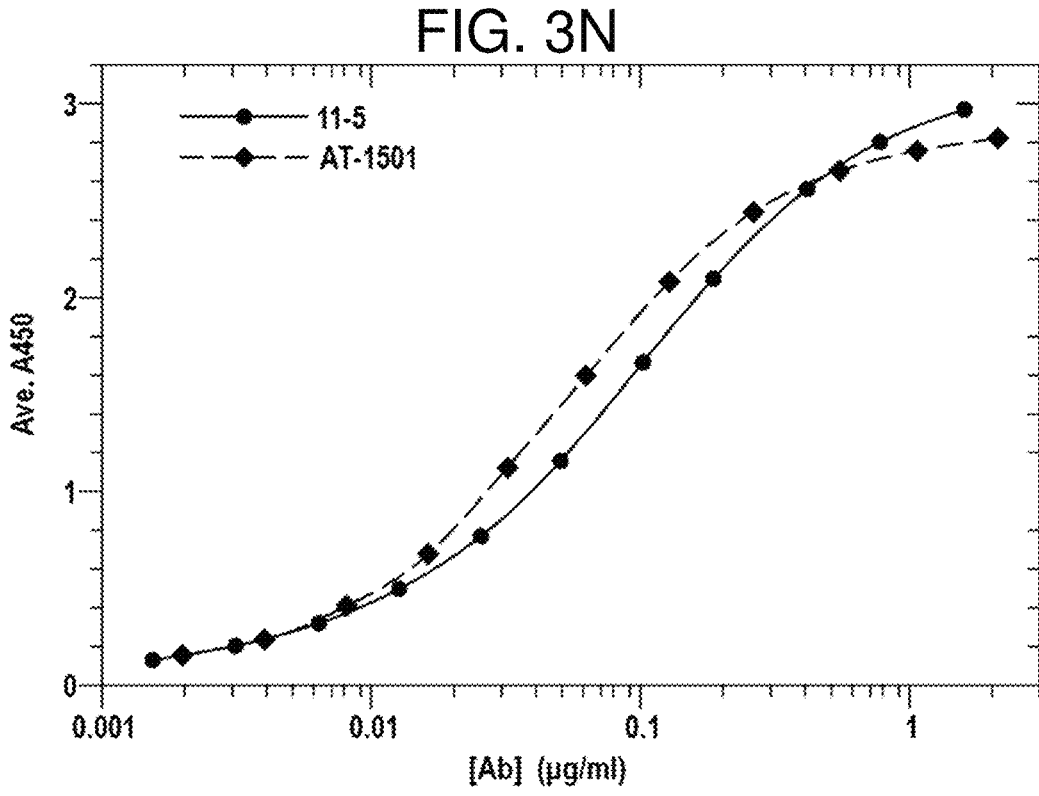
Figure 3O:
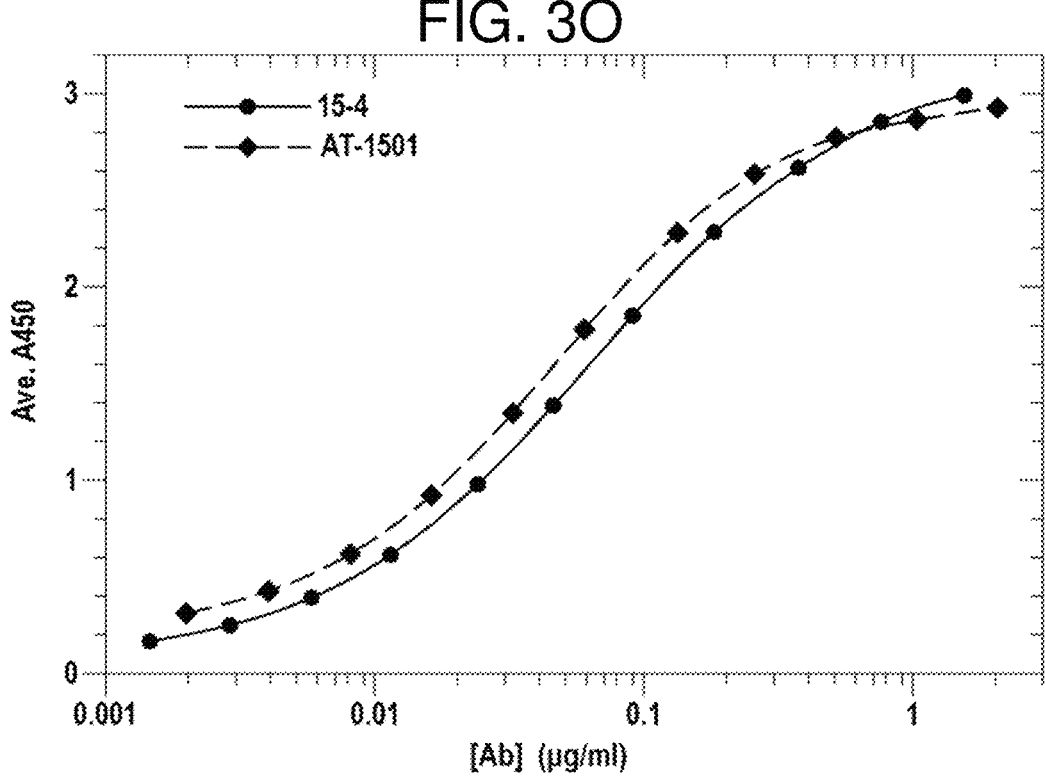
Figure 3P:
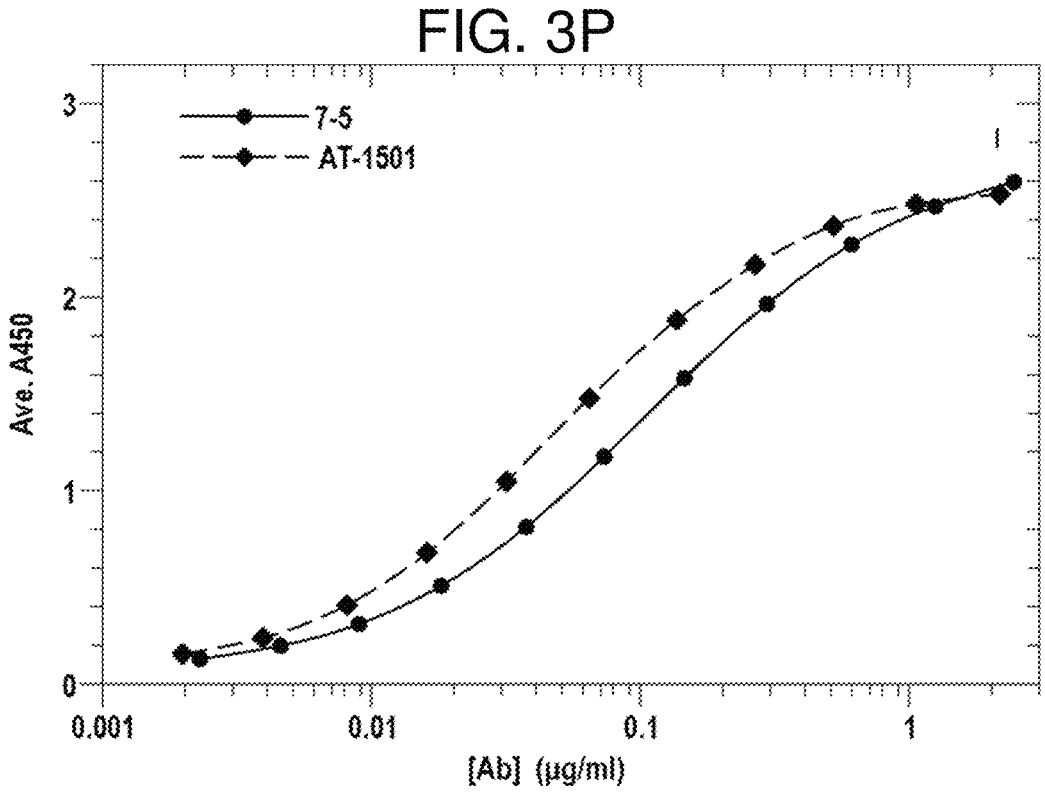
Figure 3Q:
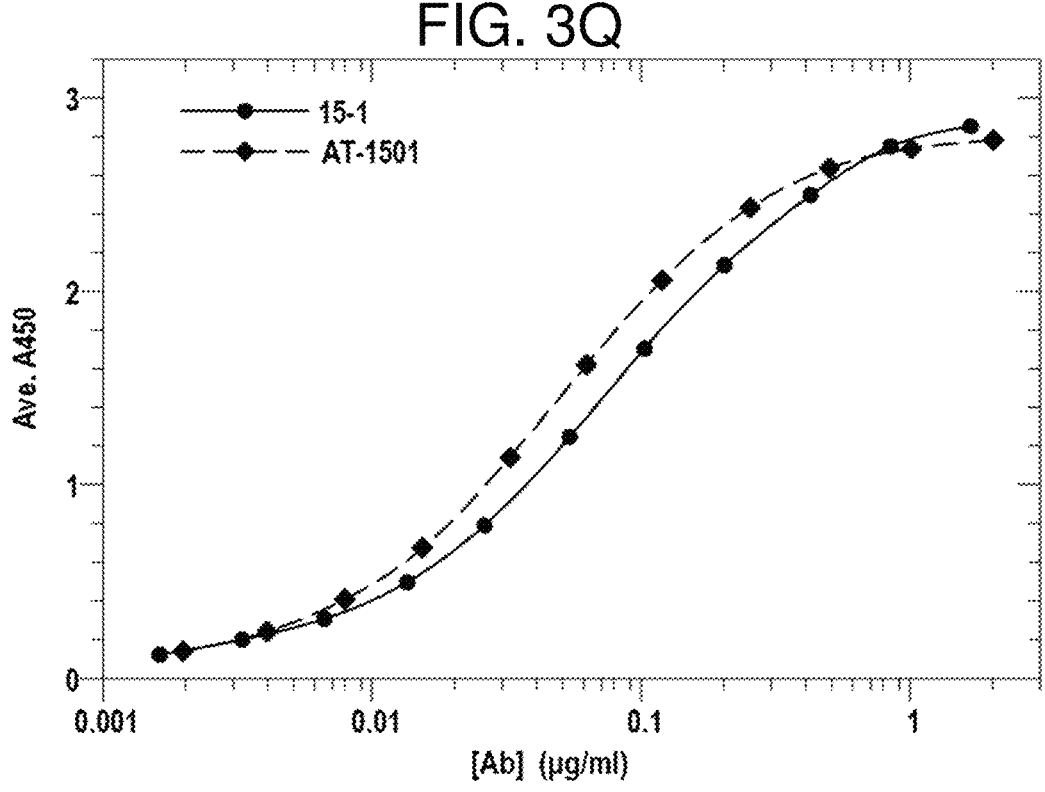

Relative CD40L binding potency was calculated as follows: [IC50 (clone)/IC50 (5c8 or AT-1501)×100%]. The ranked potency of the 16 clones versus 5c8 is shown in FIG. 1A and the ranked potency versus AT-1501 is shown in FIG. 1B. The resulting binding curves are shown in FIGS. 2A-2Q (comparison of 16 clones versus 5c8, FIG. 2H shows the comparison between AT-1501 and 5c8) and FIGS. 3A-3Q (comparison of the 16 clones versus AT-1501, FIG. 3H shows the comparison between AT-1501 and 5c8). The IC50, LCL, UCL and Relative Potency for each clone are shown in Table 2 (comparison with 5c8) and Table 3 (comparison with AT-1501).

TABLE 3

| FIG. No. | Clone | IC50 | LCL | UCL | Rel. Pot. |
|---|---|---|---|---|---|
| 3A | 12-4 | 0.020 | 0.013 | 0.027 | 45 |
| | AT-1501 | 0.044 | 0.039 | 0.049 | |
| 3B | 8-3 | 0.036 | 0.028 | 0.043 | 59 |
| | AT-1501 | 0.060 | 0.053 | 0.068 | |
| 3C | 13-2 | 0.020 | 0.013 | 0.027 | 45 |
| | AT-1501 | 0.044 | 0.038 | 0.049 | |
| 3D | 8-4 | 0.036 | 0.030 | 0.041 | 59 |
| | AT-1501 | 0.060 | 0.053 | 0.068 | |
| 3E | 16-3 | 0.022 | 0.017 | 0.026 | 48 |
| | AT-1501 | 0.045 | 0.039 | 0.051 | |
| 3F | 4-4 | 0.037 | 0.029 | 0.045 | 60 |
| | AT-1501 | 0.062 | 0.054 | 0.070 | |

TABLE 3-continued

| FIG. No. | Clone | IC50 | LCL | UCL | Rel. Pot. |
|---|---|---|---|---|---|
| 3G | 17-1 | 0.028 | 0.023 | 0.033 | 66 |
|  | AT-1501 | 0.042 | 0.035 | 0.050 |  |
| 3H | 5c8 | 0.052 | 0.046 | 0.058 | 105 |
|  | AT-1501 | 0.049 | 0.043 | 0.056 |  |
| 3I | 5-3 | 0.055 | 0.047 | 0.063 | 89 |
|  | AT-1501 | 0.062 | 0.054 | 0.070 |  |
| 3J | 10-4 | 0.075 | 0.065 | 0.086 | 115 |
|  | AT-1501 | 0.066 | 0.056 | 0.076 |  |
| 3K | 18-2 | 0.041 | 0.036 | 0.046 | 96 |
|  | AT-1501 | 0.042 | 0.035 | 0.050 |  |
| 3L | 10-1 | 0.079 | 0.070 | 0.089 | 121 |
|  | AT-1501 | 0.066 | 0.056 | 0.076 |  |
| 3M | 6-6 | 0.065 | 0.059 | 0.070 | 132 |
|  | AT-1501 | 0.049 | 0.047 | 0.051 |  |
| 3N | 11-5 | 0.092 | 0.071 | 0.112 | 174 |
|  | AT-1501 | 0.053 | 0.050 | 0.056 |  |
| 3O | 15-4 | 0.063 | 0.056 | 0.069 | 139 |
|  | AT-1501 | 0.045 | 0.039 | 0.051 |  |
| 3P | 7-5 | 0.102 | 0.094 | 0.111 | 210 |
|  | AT-1501 | 0.049 | 0.047 | 0.051 |  |
| 3Q | 15-1 | 0.081 | 0.073 | 0.089 | 159 |
|  | AT-1501 | 0.051 | 0.046 | 0.055 |  |

Example 2 Binding Activity to Human FcγRI,
FcγRIIa, FcγRIIIa and FcγRIIIb

The 16 VH/VL antibody clones constructed with an IgG1 Fc having two mutations P238S and N297G (SEQ ID NO: 21). These antibody clones were assayed for Fc effector function for binding to human FcγRI, FcγRIIa and FcγRIIIa.

Anti-CD40L antibodies (Abatacept included as negative control) are diluted to 2 ug/ml in (1×) PBS and 50 ul/well was added to Costar 96-well ½ area high binding assay plates (Corning 3690) for overnight incubation at 4° C. Plates were blocked with (1×) PBS/1.0% BSA (140 ul/well) for 1 hour at room temperature to prevent background binding. Binding curves of recombinant human FcγRI, IIa, IIIa and IIIb (from 5 ug/ml out serial 2-fold dilutions) were added (50 ul/well) and incubated for 1 hour at room temperature. Plates were washed and incubated with mouse anti-human CD16 (anti-FcRIII); CD32 (anti-FcRIIa) or CD64 (anti-FcRI) (eBioSciences/Invitrogen 14-0168-82; 16-0329-81; 14-0649-82) at 2 ug/ml (50 ul/well) for 1 hour at room temperature. Plates were washed and incubated with HRP-(Fab2) goat anti-mouse IgG (Fc specific) (Jackson Immuno. 116-036-071) at a 1:10,000 dilution (50 ul/well) for 1 hour at room temperature. Plates were washed and TMB substrate (Surmodics BioFX TMBW-1000-01) was added (50 ul/well). Color development was stopped after 5 mins at room temperature with (25 ul/well) 2NH$_2$SO$_4$.

Plates were read on Molecular Devices SpectraMax M5 plate reader using SoftMax Pro 6.2.2 program to determine absorbance at 450 nm.

Figure 4A:
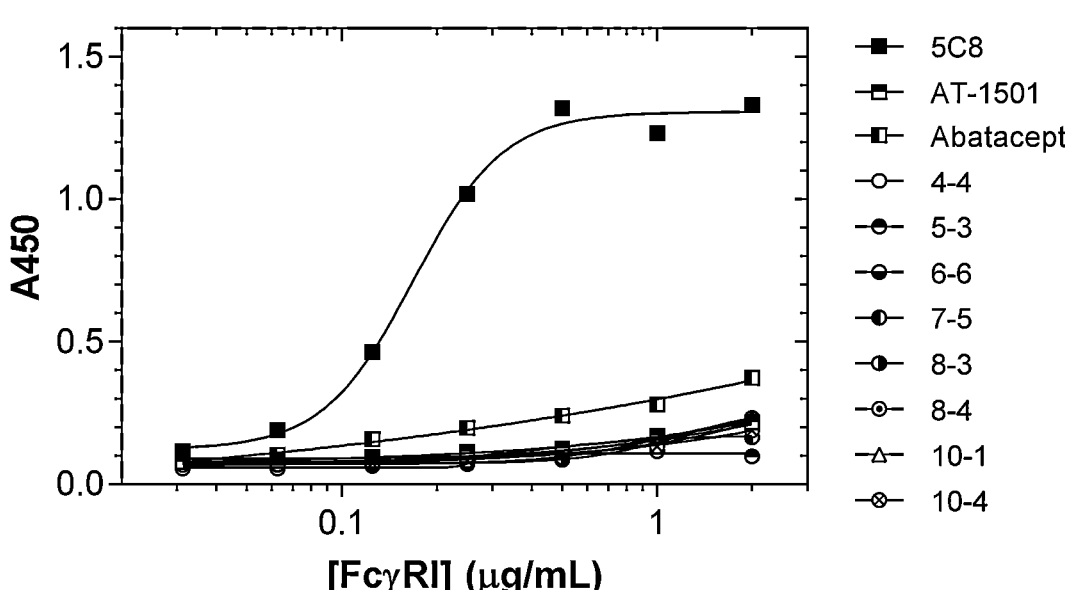
FIGS. 4A and 4B are graphs, each of which shows binding of eight of the antibody clones, 5c8, AT-1501 and abatacept to FcγRI. The only antibody having significant binding is the 5c8 antibody.
Figure 4B:
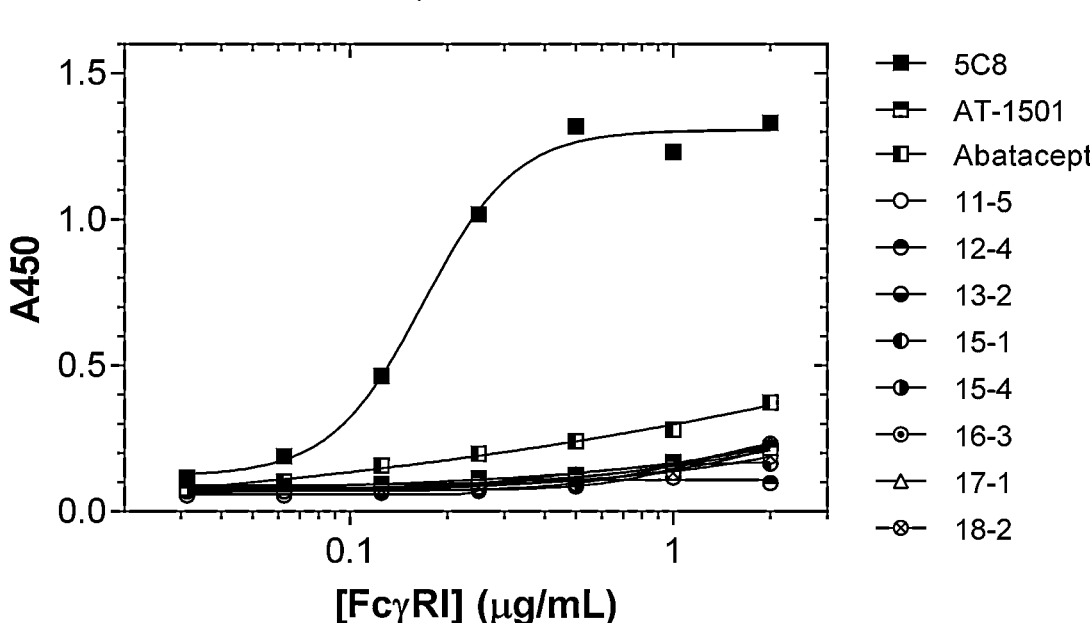
Figure 5A:
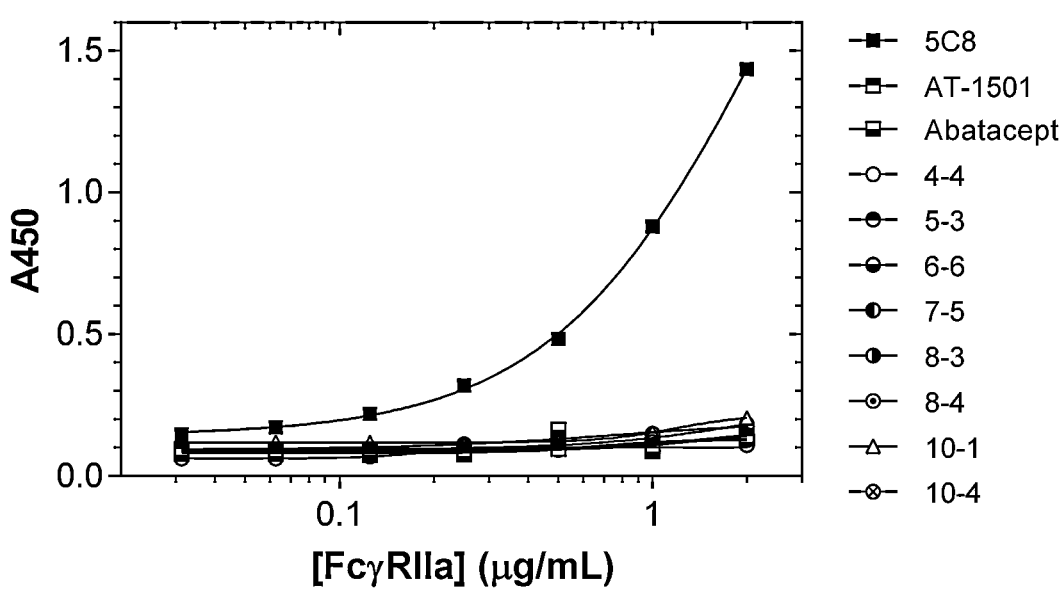
FIGS. 5A and 5B are graphs, each of which shows binding of eight of the antibody clones, 5c8, AT-1501 and abatacept to FcγRIIa. The only antibody having significant binding is the 5c8 antibody.
Figure 5B:
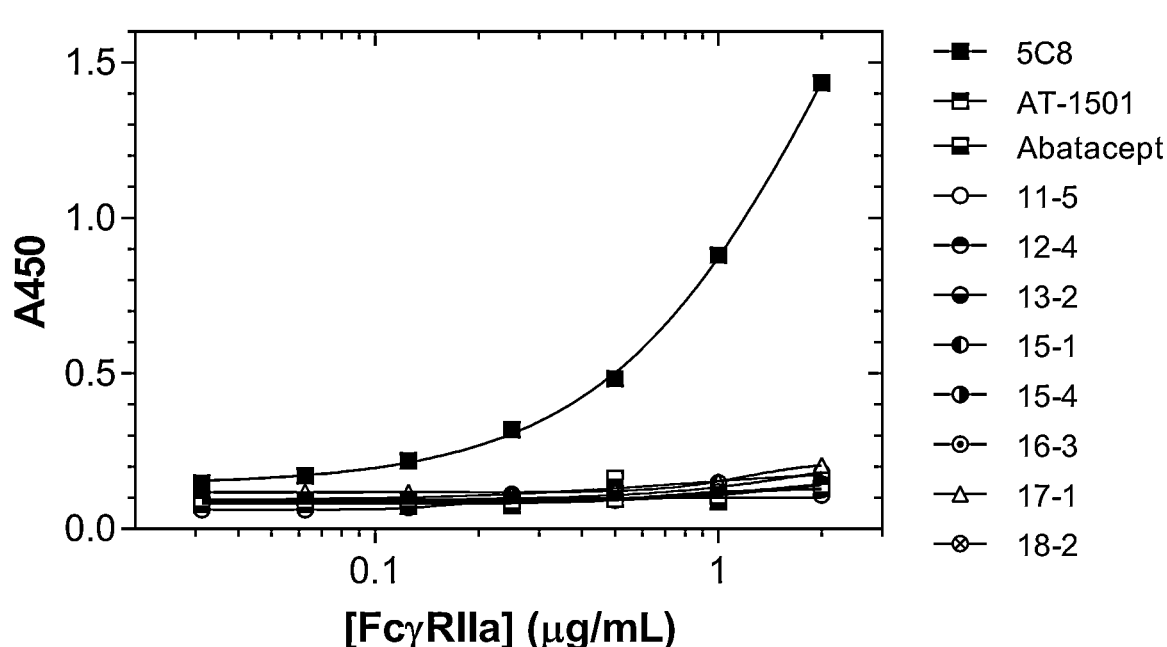

As can be seen in the figures, the clones disclosed in this application were negative for binding to the three Fc receptors while 5c8 bound to FcγRI, FcγRIIa but not to FcγRIIIa or FcγRIIIb. Each of FIGS. 4A and 4B show the binding to FcγRIa for eight antibody clones compared with the binding curves of 5c8, AT-1501 and Abatacept. Each of FIGS. 5A and 5B show the binding to FcγRIIa for eight antibody clones compared with the binding curve of 5c8, AT-1501 and Abatacept. Each of FIGS. 6A and 6B show the binding to FcγRIIIa for eight antibody clones compared with the binding curves of 5c8, AT-1501 and Abatacept. Each of FIGS. 6C and 6D show the binding to FcγRIIIb for eight antibody clones compared with the binding curves of 5c8, AT-1501 and Abatacept. (FIGS. 4A, 5A, 6A and 6A show results from antibody clones 4-4, 5-3,6-6, 7-5, 8-3, 8-4, 10-1 and 10-4, FIGS. 4B, 5B, 6C and 6D show results from antibody clones 11-5, 12-4, 13-2, 15-1, 15-4, 16-3, 17-1 and 18-2).

Example 4 Binding Activity to C1q

Anti-CD40L antibodies (Abatacept included as negative control) were diluted to 2 ug/ml in (1×) PBS and 50 ul/well was added to Costar 96-well ½ area high binding assay plates (Corning 3690) for overnight incubation at 4° C. Plates were blocked with (1×) PBS/1.0% BSA (140 ul/well) for 1 hour at room temperature to prevent background binding. Binding curves of natural human C1q protein (Abcam ab96363) from 10 ug/ml out serial 2-fold dilutions were added (50 ul/well) for 1 hour at room temperature. Plates were washed and HRP-sheep anti-human C1q (Abcam ab46191) is added at a 1:400 dilution (50 ul/well) and incubated for 1 hour at room temperature. Plates were washed and TMB substrate (Surmodics BioFX TMBW-1000-01) is added (50 ul/well). Color development was stopped after 5 minutes at room temperature with (25 ul/well) 2NH$_2$SO$_4$. Plates were read on Molecular Devices SpectraMax M5 plate reader using SoftMax Pro 6.2.2 program to determine absorbance at 450 nm.

As can be seen in the figures, the antibody from all sixteen antibody clones disclosed in this application were negative for binding to C1q while 5c8 showed significant binding. Each of FIGS. 7A and 7B show the binding to C1q for eight antibody clones compared with the binding curves of 5c8, AT-1501 and Abatacept. FIG. 7A shows results from antibody clones 4-4, 5-3, 6-6, 7-5, 8-3, 8-4, 10-1 and 10-4 and 7B shows results from antibody clones 11-5, 12-4, 13-2, 15-1, 15-4, 16-3, 17-1 and 18-2.

What is claimed is:

1. An isolated antibody or antigen-binding fragment thereof, that specifically binds to CD40L, comprising:

(a) a heavy chain variable region (VH) comprising;
   i) a CDRH1 domain comprising the sequence set forth in SEQ ID NO:9;
   ii) a CDRH2 domain comprising the sequence set forth in SEQ ID NO: 10, 11, 12, 13, or 14;
   iii) a CDRH3 domain comprising the sequence set forth in SEQ ID NO: 15; and (b) a light chain variable region (VL) comprising:
   i) a CDRL1 domain comprising the sequence set forth in SEQ ID NO: 16 or 17;
   ii) a CDRL2 domain comprising the sequence set forth in SEQ ID NO: 18 or 19;
   iii) a CDRL3 domain comprising the sequence set forth in SEQ ID NO: 20.

2. The isolated antibody or antigen-binding fragment thereof of claim 1, comprising:

(a) a heavy chain variable region (VH) comprising;
   i) a CDRH1 domain comprising the sequence set forth in SEQ ID NO: 9;
   ii) a CDRH2 domain comprising the sequence set forth in SEQ ID NO: 10;
   iii) a CDRH3 domain comprising the sequence set forth in SEQ ID NO: 15; and (b) a light chain variable region (VL) comprising:
   i) a CDRL1 domain comprising the sequence set forth in SEQ ID NO: 16;
   ii) a CDRL2 domain comprising the sequence set forth in SEQ ID NO: 18;
   iii) a CDRL3 domain comprising the sequence set forth in SEQ ID NO: 20; or (c) a heavy chain variable region (VH) comprising;
   i) a CDRH1 domain comprising the sequence set forth in SEQ ID NO: 9;
   ii) a CDRH2 domain comprising the sequence set forth in SEQ ID NO: 10;
   iii) a CDRH3 domain comprising the sequence set forth in SEQ ID NO: 15; and (d) a light chain variable region (VL) comprising:
   i) a CDRL1 domain comprising the sequence set forth in SEQ ID NO: 17;
   ii) a CDRL2 domain comprising the sequence set forth in SEQ ID NO: 18;
   iii) a CDRL3 domain comprising the sequence set forth in SEQ ID NO: 20; or (e) a heavy chain variable region (VH) comprising;
   i) a CDRH1 domain comprising the sequence set forth in SEQ ID NO: 9;
   ii) a CDRH2 domain comprising the sequence set forth in SEQ ID NO: 10;
   iii) a CDRH3 domain comprising the sequence set forth in SEQ ID NO: 15; and (f) a light chain variable region (VL) comprising:
   i) a CDRL1 domain comprising the sequence set forth in SEQ ID NO: 16;
   ii) a CDRL2 domain comprising the sequence set forth in SEQ ID NO: 19;
   iii) a CDRL3 domain comprising the sequence set forth in SEQ ID NO: 20; or (g) a heavy chain variable region (VH) comprising;
    i) a CDRH1 domain comprising the sequence set forth in SEQ ID NO: 9;
    ii) a CDRH2 domain comprising the sequence set forth in SEQ ID NO: 10;
    iii) a CDRH3 domain comprising the sequence set forth in SEQ ID NO: 15; and
(h) a light chain variable region (VL) comprising:
    i) a CDRL1 domain comprising the sequence set forth in SEQ ID NO: 17;
    ii) a CDRL2 domain comprising the sequence set forth in SEQ ID NO: 19;
    iii) a CDRL3 domain comprising the sequence set forth in SEQ ID NO: 20; or
(i) a heavy chain variable region (VH) comprising;
    i) a CDRH1 domain comprising the sequence set forth in SEQ ID NO: 9;
    ii) a CDRH2 domain comprising the sequence set forth in SEQ ID NO: 11;
    iii) a CDRH3 domain comprising the sequence set forth in SEQ ID NO: 15; and
(j) a light chain variable region (VL) comprising:
    i) a CDRL1 domain comprising the sequence set forth in SEQ ID NO: 16;
    ii) a CDRL2 domain comprising the sequence set forth in SEQ ID NO: 18;
    iii) a CDRL3 domain comprising the sequence set forth in SEQ ID NO: 20; or
(k) a heavy chain variable region (VH) comprising;
    i) a CDRH1 domain comprising the sequence set forth in SEQ ID NO: 9;
    ii) a CDRH2 domain comprising the sequence set forth in SEQ ID NO: 11;
    iii) a CDRH3 domain comprising the sequence set forth in SEQ ID NO: 15; and
(l) a light chain variable region (VL) comprising:
    i) a CDRL1 domain comprising the sequence set forth in SEQ ID NO: 17;
    ii) a CDRL2 domain comprising the sequence set forth in SEQ ID NO: 18;
    iii) a CDRL3 domain comprising the sequence set forth in SEQ ID NO: 20; or
(m) a heavy chain variable region (VH) comprising;
    i) a CDRH1 domain comprising the sequence set forth in SEQ ID NO: 9;
    ii) a CDRH2 domain comprising the sequence set forth in SEQ ID NO: 11;
    iii) a CDRH3 domain comprising the sequence set forth in SEQ ID NO: 15; and
(n) a light chain variable region (VL) comprising:
    i) a CDRL1 domain comprising the sequence set forth in SEQ ID NO: 16;
    ii) a CDRL2 domain comprising the sequence set forth in SEQ ID NO: 19;
    iii) a CDRL3 domain comprising the sequence set forth in SEQ ID NO: 20; or
(o) a heavy chain variable region (VH) comprising;
    i) a CDRH1 domain comprising the sequence set forth in SEQ ID NO: 9;
    ii) a CDRH2 domain comprising the sequence set forth in SEQ ID NO: 11;
    iii) a CDRH3 domain comprising the sequence set forth in SEQ ID NO: 15; and
(p) a light chain variable region (VL) comprising:
    i) a CDRL1 domain comprising the sequence set forth in SEQ ID NO: 17;

ii) a CDRL2 domain comprising the sequence set forth in SEQ ID NO: 19;
    iii) a CDRL3 domain comprising the sequence set forth in SEQ ID NO: 20; or
(q) a heavy chain variable region (VH) comprising;
    i) a CDRH1 domain comprising the sequence set forth in SEQ ID NO: 9;
    ii) a CDRH2 domain comprising the sequence set forth in SEQ ID NO: 12;
    iii) a CDRH3 domain comprising the sequence set forth in SEQ ID NO: 15; and
(r) a light chain variable region (VL) comprising:
    i) a CDRL1 domain comprising the sequence set forth in SEQ ID NO: 16;
    ii) a CDRL2 domain comprising the sequence set forth in SEQ ID NO: 18;
    iii) a CDRL3 domain comprising the sequence set forth in SEQ ID NO: 20; or
(s) a heavy chain variable region (VH) comprising;
    i) a CDRH1 domain comprising the sequence set forth in SEQ ID NO: 9;
    ii) a CDRH2 domain comprising the sequence set forth in SEQ ID NO: 12;
    iii) a CDRH3 domain comprising the sequence set forth in SEQ ID NO: 15; and
(t) a light chain variable region (VL) comprising:
    i) a CDRL1 domain comprising the sequence set forth in SEQ ID NO: 17;
    ii) a CDRL2 domain comprising the sequence set forth in SEQ ID NO: 18;
    iii) a CDRL3 domain comprising the sequence set forth in SEQ ID NO: 20; or
(u) a heavy chain variable region (VH) comprising;
    i) a CDRH1 domain comprising the sequence set forth in SEQ ID NO:9;
    ii) a CDRH2 domain comprising the sequence set forth in SEQ ID NO: 12;
    iii) a CDRH3 domain comprising the sequence set forth in SEQ ID NO: 15; and
(v) a light chain variable region (VL) comprising:
    i) a CDRL1 domain comprising the sequence set forth in SEQ ID NO: 16;
    ii) a CDRL2 domain comprising the sequence set forth in SEQ ID NO: 19;
    iii) a CDRL3 domain comprising the sequence set forth in SEQ ID NO: 20; or
(w) a heavy chain variable region (VH) comprising;
    i) a CDRH1 domain comprising the sequence set forth in SEQ ID NO: 9;
    ii) a CDRH2 domain comprising the sequence set forth in SEQ ID NO: 12;
    iii) a CDRH3 domain comprising the sequence set forth in SEQ ID NO: 15; and
(x) a light chain variable region (VL) comprising:
    i) a CDRL1 domain comprising the sequence set forth in SEQ ID NO: 17;
    ii) a CDRL2 domain comprising the sequence set forth in SEQ ID NO: 19;
    iii) a CDRL3 domain comprising the sequence set forth in SEQ ID NO: 20; or
(y) a heavy chain variable region (VH) comprising;
    i) a CDRH1 domain comprising the sequence set forth in SEQ ID NO: 9;
    ii) a CDRH2 domain comprising the sequence set forth in SEQ ID NO: 13;
    iii) a CDRH3 domain comprising the sequence set forth in SEQ ID NO: 15; and (z) a light chain variable region (VL) comprising:
  i) a CDRL1 domain comprising the sequence set forth in SEQ ID NO: 16;
  ii) a CDRL2 domain comprising the sequence set forth in SEQ ID NO: 18;
  iii) a CDRL3 domain comprising the sequence set forth in SEQ ID NO: 20; or (aa) a heavy chain variable region (VH) comprising;
  i) a CDRH1 domain comprising the sequence set forth in SEQ ID NO:9;
  ii) a CDRH2 domain comprising the sequence set forth in SEQ ID NO: 13;
  iii) a CDRH3 domain comprising the sequence set forth in SEQ ID NO: 15; and (ab) a light chain variable region (VL) comprising:
  i) a CDRL1 domain comprising the sequence set forth in SEQ ID NO: 17;
  ii) a CDRL2 domain comprising the sequence set forth in SEQ ID NO: 18;
  iii) a CDRL3 domain comprising the sequence set forth in SEQ ID NO: 20; or (ad) a heavy chain variable region (VH) comprising;
  i) a CDRH1 domain comprising the sequence set forth in SEQ ID NO: 9;
  ii) a CDRH2 domain comprising the sequence set forth in SEQ ID NO: 13;
  iii) a CDRH3 domain comprising the sequence set forth in SEQ ID NO: 15; and (ae) a light chain variable region (VL) comprising:
  i) a CDRL1 domain comprising the sequence set forth in SEQ ID NO: 16;
  ii) a CDRL2 domain comprising the sequence set forth in SEQ ID NO: 19;
  iii) a CDRL3 domain comprising the sequence set forth in SEQ ID NO: 20; or (af) a heavy chain variable region (VH) comprising;
  i) a CDRH1 domain comprising the sequence set forth in SEQ ID NO: 9;
  ii) a CDRH2 domain comprising the sequence set forth in SEQ ID NO: 13;
  iii) a CDRH3 domain comprising the sequence set forth in SEQ ID NO: 15; and (ag) a light chain variable region (VL) comprising:
  i) a CDRL1 domain comprising the sequence set forth in SEQ ID NO: 17;
  ii) a CDRL2 domain comprising the sequence set forth in SEQ ID NO: 19;
  iii) a CDRL3 domain comprising the sequence set forth in SEQ ID NO: 20; or (ah) a heavy chain variable region (VH) comprising;
  i) a CDRH1 domain comprising the sequence set forth in SEQ ID NO: 9;
  ii) a CDRH2 domain comprising the sequence set forth in SEQ ID NO: 13;
  iii) a CDRH3 domain comprising the sequence set forth in SEQ ID NO: 15; and (ai) a light chain variable region (VL) comprising:
  i) a CDRL1 domain comprising the sequence set forth in SEQ ID NO: 17;
  ii) a CDRL2 domain comprising the sequence set forth in SEQ ID NO: 19;
  iii) a CDRL3 domain comprising the sequence set forth in SEQ ID NO: 20; or (aj) a heavy chain variable region (VH) comprising;
  i) a CDRH1 domain comprising the sequence set forth in SEQ ID NO: 9;

ii) a CDRH2 domain comprising the sequence set forth in SEQ ID NO: 14;
  iii) a CDRH3 domain comprising the sequence set forth in SEQ ID NO: 15; and (ak) a light chain variable region (VL) comprising:
  i) a CDRL1 domain comprising the sequence set forth in SEQ ID NO: 16;
  ii) a CDRL2 domain comprising the sequence set forth in SEQ ID NO: 18;
  iii) a CDRL3 domain comprising the sequence set forth in SEQ ID NO: 20; or (al) a heavy chain variable region (VH) comprising;
  i) a CDRH1 domain comprising the sequence set forth in SEQ ID NO: 9;
  ii) a CDRH2 domain comprising the sequence set forth in SEQ ID NO: 14;
  iii) a CDRH3 domain comprising the sequence set forth in SEQ ID NO: 15; and (am) a light chain variable region (VL) comprising:
  i) a CDRL1 domain comprising the sequence set forth in SEQ ID NO: 17;
  ii) a CDRL2 domain comprising the sequence set forth in SEQ ID NO: 18;
  iii) a CDRL3 domain comprising the sequence set forth in SEQ ID NO: 20; or (an) a heavy chain variable region (VH) comprising;
  i) a CDRH1 domain comprising the sequence set forth in SEQ ID NO: 9;
  ii) a CDRH2 domain comprising the sequence set forth in SEQ ID NO: 14;
  iii) a CDRH3 domain comprising the sequence set forth in SEQ ID NO: 15; and (ao) a light chain variable region (VL) comprising:
  i) a CDRL1 domain comprising the sequence set forth in SEQ ID NO: 16;
  ii) a CDRL2 domain comprising the sequence set forth in SEQ ID NO: 19;
  iii) a CDRL3 domain comprising the sequence set forth in SEQ ID NO: 20; or (ap) a heavy chain variable region (VH) comprising;
  i) a CDRH1 domain comprising the sequence set forth in SEQ ID NO: 9;
  ii) a CDRH2 domain comprising the sequence set forth in SEQ ID NO: 14;
  iii) a CDRH3 domain comprising the sequence set forth in SEQ ID NO: 15; and (aq) a light chain variable region (VL) comprising:
  i) a CDRL1 domain comprising the sequence set forth in SEQ ID NO: 17;
  ii) a CDRL2 domain comprising the sequence set forth in SEQ ID NO: 19;
  iii) a CDRL3 domain comprising the sequence set forth in SEQ ID NO: 20.

3. The isolated antibody or antigen-binding fragment thereof of claim 1, wherein the antibody or antigen binding fragment comprises an Fc region and the Fc region has been engineered to reduce or eliminate one or more Fc effector function.

4. The isolated antibody or antigen-binding fragment thereof of claim 3, wherein the one or more Fc effector function is FcR binding or complement binding.

5. The isolated antibody or antigen-binding fragment thereof of claim 1, wherein the antibody is an IgG1 isotype, and wherein the antibody comprises a heavy chain constant region that comprises the amino acid sequence as set forth in SEQ ID NO: 21.

6. The isolated antibody or antigen-binding fragment thereof of claim 1, further comprising a heavy chain constant region, wherein the heavy chain constant region comprises the amino acid sequence as set forth in SEQ ID NO: 22.

7. The isolated antibody or antigen-binding fragment thereof of claim 1, further comprising a heavy chain constant region, wherein the heavy chain constant region comprises the amino acid sequence as set forth in SEQ ID NO: 23.

8. The isolated antibody or antigen-binding fragment thereof of claim 1, further comprising a heavy chain constant region, wherein the heavy chain constant region comprises the amino acid sequence as set forth in SEQ ID NO: 24.

9. The isolated antibody or antigen-binding fragment thereof of claim 1, wherein the antibody further comprises a light chain constant region, wherein the light chain constant region comprises the amino acid sequence set forth in SEQ ID NO: 25.

10. The isolated antibody or antigen-binding fragment thereof of claim 1, wherein the antibody comprises:

(a) a heavy chain having the amino acid sequence as set forth in SEQ ID NO: 46 and the light chain having the amino acid sequence as set forth in SEQ ID NO: 38; or (b) a heavy chain having the amino acid sequence as set forth in SEQ ID NO: 46 and the light chain having the amino acid sequence as set forth in SEQ ID NO: 39: or (c) a heavy chain having the amino acid sequence as set forth in SEQ ID NO: 46 and the light chain having the amino acid sequence as set forth in SEQ ID NO: 40: or (d) a heavy chain having the amino acid sequence as set forth in SEQ ID NO: 46 and the light chain having the amino acid sequence as set forth in SEQ ID NO: 41; or (e) a heavy chain having the amino acid sequence as set forth in SEQ ID NO: 47 and the light chain having the amino acid sequence as set forth in SEQ ID NO: 38; or (f) a heavy chain having the amino acid sequence as set forth in SEQ ID NO: 47 and the light chain having the amino acid sequence as set forth in SEQ ID NO: 39: or (g) a heavy chain having the amino acid sequence as set forth in SEQ ID NO: 47 and the light chain having the amino acid sequence as set forth in SEQ ID NO: 40: or (h) a heavy chain having the amino acid sequence as set forth in SEQ ID NO: 47 and the light chain having the amino acid sequence as set forth in SEQ ID NO: 41; or (i) a heavy chain having the amino acid sequence as set forth in SEQ ID NO: 48 and the light chain having the amino acid sequence as set forth in SEQ ID NO: 38; or (j) a heavy chain having the amino acid sequence as set forth in SEQ ID NO: 48 and the light chain having the amino acid sequence as set forth in SEQ ID NO: 39: or (k) a heavy chain having the amino acid sequence as set forth in SEQ ID NO: 48 and the light chain having the amino acid sequence as set forth in SEQ ID NO: 40: or (l) a heavy chain having the amino acid sequence as set forth in SEQ ID NO: 48 and the light chain having the amino acid sequence as set forth in SEQ ID NO: 41; or (m) a heavy chain having the amino acid sequence as set forth in SEQ ID NO: 49 and the light chain having the amino acid sequence as set forth in SEQ ID NO: 38; or (n) a heavy chain having the amino acid sequence as set forth in SEQ ID NO: 49 and the light chain having the amino acid sequence as set forth in SEQ ID NO: 39: or (o) a heavy chain having the amino acid sequence as set forth in SEQ ID NO: 49 and the light chain having the amino acid sequence as set forth in SEQ ID NO: 40: or (p) a heavy chain having the amino acid sequence as set forth in SEQ ID NO: 49 and the light chain having the amino acid sequence as set forth in SEQ ID NO: 41.

11. The isolated antibody or antigen-binding fragment thereof of claim 1, wherein the antibody comprises:

(a) a heavy chain having the amino acid sequence as set forth in SEQ ID NO: 50 and the light chain having the amino acid sequence as set forth in SEQ ID NO: 38; or (b) a heavy chain having the amino acid sequence as set forth in SEQ ID NO: 50 and the light chain having the amino acid sequence as set forth in SEQ ID NO: 39: or (c) a heavy chain having the amino acid sequence as set forth in SEQ ID NO: 50 and the light chain having the amino acid sequence as set forth in SEQ ID NO: 40: or (d) a heavy chain having the amino acid sequence as set forth in SEQ ID NO: 50 and the light chain having the amino acid sequence as set forth in SEQ ID NO: 41; or (e) a heavy chain having the amino acid sequence as set forth in SEQ ID NO: 51 and the light chain having the amino acid sequence as set forth in SEQ ID NO: 38; or (f) a heavy chain having the amino acid sequence as set forth in SEQ ID NO: 51 and the light chain having the amino acid sequence as set forth in SEQ ID NO: 39: or (g) a heavy chain having the amino acid sequence as set forth in SEQ ID NO: 51 and the light chain having the amino acid sequence as set forth in SEQ ID NO: 40: or (h) a heavy chain having the amino acid sequence as set forth in SEQ ID NO: 51 and the light chain having the amino acid sequence as set forth in SEQ ID NO: 41; or (i) a heavy chain having the amino acid sequence as set forth in SEQ ID NO: 52 and the light chain having the amino acid sequence as set forth in SEQ ID NO: 38; or (j) a heavy chain having the amino acid sequence as set forth in SEQ ID NO: 52 and the light chain having the amino acid sequence as set forth in SEQ ID NO: 39: or (k) a heavy chain having the amino acid sequence as set forth in SEQ ID NO: 52 and the light chain having the amino acid sequence as set forth in SEQ ID NO: 40: or (l) a heavy chain having the amino acid sequence as set forth in SEQ ID NO: 52 and the light chain having the amino acid sequence as set forth in SEQ ID NO: 41; or (m) a heavy chain having the amino acid sequence as set forth in SEQ ID NO: 53 and the light chain having the amino acid sequence as set forth in SEQ ID NO: 38; or (n) a heavy chain having the amino acid sequence as set forth in SEQ ID NO: 53 and the light chain having the amino acid sequence as set forth in SEQ ID NO: 39: or (o) a heavy chain having the amino acid sequence as set forth in SEQ ID NO: 53 and the light chain having the amino acid sequence as set forth in SEQ ID NO: 40: or (p) a heavy chain having the amino acid sequence as set forth in SEQ ID NO: 53 and the light chain having the amino acid sequence as set forth in SEQ ID NO: 41.

12. The isolated antibody or antigen-binding fragment thereof of claim 1, wherein the antibody comprises:

(a) a heavy chain having the amino acid sequence as set forth in SEQ ID NO: 54 and the light chain having the amino acid sequence as set forth in SEQ ID NO: 38; or (b) a heavy chain having the amino acid sequence as set forth in SEQ ID NO: 54 and the light chain having the amino acid sequence as set forth in SEQ ID NO: 39: or (c) a heavy chain having the amino acid sequence as set forth in SEQ ID NO: 54 and the light chain having the amino acid sequence as set forth in SEQ ID NO: 40: or (d) a heavy chain having the amino acid sequence as set forth in SEQ ID NO: 54 and the light chain having the amino acid sequence as set forth in SEQ ID NO: 41; or (e) a heavy chain having the amino acid sequence as set forth in SEQ ID NO: 55 and the light chain having the amino acid sequence as set forth in SEQ ID NO: 38; or (f) a heavy chain having the amino acid sequence as set forth in SEQ ID NO: 55 and the light chain having the amino acid sequence as set forth in SEQ ID NO: 39: or (g) a heavy chain having the amino acid sequence as set forth in SEQ ID NO: 55 and the light chain having the amino acid sequence as set forth in SEQ ID NO: 40: or (h) a heavy chain having the amino acid sequence as set forth in SEQ ID NO: 55 and the light chain having the amino acid sequence as set forth in SEQ ID NO: 41; or (i) a heavy chain having the amino acid sequence as set forth in SEQ ID NO: 56 and the light chain having the amino acid sequence as set forth in SEQ ID NO: 38; or (j) a heavy chain having the amino acid sequence as set forth in SEQ ID NO: 56 and the light chain having the amino acid sequence as set forth in SEQ ID NO: 39: or (k) a heavy chain having the amino acid sequence as set forth in SEQ ID NO: 56 and the light chain having the amino acid sequence as set forth in SEQ ID NO: 40: or (l) a heavy chain having the amino acid sequence as set forth in SEQ ID NO: 56 and the light chain having the amino acid sequence as set forth in SEQ ID NO: 41; or (m) a heavy chain having the amino acid sequence as set forth in SEQ ID NO: 57 and the light chain having the amino acid sequence as set forth in SEQ ID NO: 38; or (n) a heavy chain having the amino acid sequence as set forth in SEQ ID NO: 57 and the light chain having the amino acid sequence as set forth in SEQ ID NO: 39: or (o) a heavy chain having the amino acid sequence as set forth in SEQ ID NO: 57 and the light chain having the amino acid sequence as set forth in SEQ ID NO: 40: or (p) a heavy chain having the amino acid sequence as set forth in SEQ ID NO: 57 and the light chain having the amino acid sequence as set forth in SEQ ID NO: 41.

13. A method for treating a subject with a neurodegen-erative or a neuromuscular disease or disorder; an inflam-matory or immune disease or disorder; or an autoimmune disease, comprising administering to the subject a therapeu-tically effective amount of an antibody or antigen-binding fragment thereof of claim 1.

14. The method of claim 13, wherein the autoimmune disease is selected from the group consisting of systemic lupus erythematous, type-1 diabetes, Myasthenia gravis, psoriasis, Addison's disease, Crohn's disease, uveitis, mul-tiple sclerosis, hemolytic anemia, inflammatory bowel dis-ease, immune thrombocytopenia purpura, Graves' disease, and rheumatoid arthritis.

15. The method of claim 13, wherein the neurodegenera-tive disorder or a neuromuscular disorder is selected from the group consisting of Alzheimer's Disease, Parkinson's Disease, Amyotrophic Lateral Sclerosis, Multifocal Motor Neuropathy, Primary Lateral Sclerosis, Spinal Muscular Atrophy, Kennedy's Disease, or Spinocerebellar Ataxia.

16. The method of claim 13, wherein the neurodegenera-tive disease or disorder is Amyotrophic Lateral Sclerosis.

17. A method of inhibiting an immune response in a subject comprising administering to the subject a therapeu-tically effective amount of an antibody or antigen-binding fragment thereof of claim 1.

18. The method of claim 17, wherein the immune response is graft vs. host disease, or organ transplant rejec-tion.

19. The method of claim 17, wherein the antibody or antigen-binding fragment thereof is administered in combi-nation with another therapeutic agent.

20. The method of claim 19, wherein the antibody or antigen-binding fragment thereof is administered in combi-nation with a compound that blocks the interaction between CD28 and CD86 or between CD28 and CD80.

21. The method of claim 20, wherein the compound that blocks the interaction between CD28 and CD86 or between CD28 and CD80 is a CTLA4-Ig fusion protein, abatacept, belatacept, or galiximab.

* * * * *